(12) United States Patent
Okuda et al.

(10) Patent No.: US 7,919,509 B2
(45) Date of Patent: Apr. 5, 2011

(54) 2-OXOCHROMENE DERIVATIVES

(75) Inventors: Ayumu Okuda, Tokyo (JP); Takayuki Matsuda, Tokyo (JP); Toru Miura, Tokyo (JP); Hidefumi Ozawa, Tokyo (JP); Ayako Tosaka, Tokyo (JP); Koichi Yamazaki, Tokyo (JP); Yuki Yamaguchi, Tokyo (JP); Sayaka Kurobuchi, Tokyo (JP); Yuichiro Watanabe, Tokyo (JP); Kimiyuki Shibuya, Tokyo (JP)

(73) Assignee: Kowa Company, Ltd., Nagoya-shi, Aichi (JP)

( * ) Notice: Subject to any disclaimer, the term of this patent is extended or adjusted under 35 U.S.C. 154(b) by 0 days.

(21) Appl. No.: 12/394,548

(22) Filed: Feb. 27, 2009

(65) Prior Publication Data

US 2009/0286780 A1    Nov. 19, 2009

Related U.S. Application Data

(60) Provisional application No. 61/032,651, filed on Feb. 29, 2008.

(51) Int. Cl.
| | |
|---|---|
| A61K 31/4166 | (2006.01) |
| A61K 31/427 | (2006.01) |
| A61K 31/45 | (2006.01) |
| A61K 31/422 | (2006.01) |
| A61K 31/4525 | (2006.01) |
| C07D 405/12 | (2006.01) |
| C07D 417/12 | (2006.01) |
| C07D 413/12 | (2006.01) |
| C07D 407/12 | (2006.01) |

(52) U.S. Cl. ........ 514/320; 514/337; 514/348; 514/389; 514/376; 514/422; 548/311.4; 548/483; 548/227; 548/525; 546/296; 546/196; 546/219

(58) Field of Classification Search .................. None
See application file for complete search history.

(56) References Cited

U.S. PATENT DOCUMENTS

2005/0215577 A1    9/2005  Dehmlow et al.

FOREIGN PATENT DOCUMENTS

| EP | 527433 A1 * | 2/1993 |
|---|---|---|
| JP | 2002-539155 A | 11/2002 |
| JP | 2004-509161 A | 3/2004 |
| WO | 00/54759 A2 | 9/2000 |
| WO | 02/24632 A2 | 3/2002 |
| WO | 03/082192 A2 | 10/2003 |
| WO | 2004/024161 A1 | 3/2004 |
| WO | 2004/058717 A1 | 7/2004 |
| WO | 2004/072046 A2 | 8/2004 |
| WO | 2005/023188 A2 | 3/2005 |

OTHER PUBLICATIONS

Byrn et al. Solid-State Chemistry of Drugs, 2d, Chapter 11 Hydrates and Solvates/hydrates, 233-247, (1999).*

Morissette et al. Adv. Drug Delivery Rev. 2004, 56, 275-300.*
Rouhi, Chem. & Eng. News, Feb. 24, 2003, 81(8), 32-35.*
Schafer et al. Drug Discovery Today, 13:913 (2008).*
Horig et al. Journal of Translational Medicine, 2:44 (2004).*
Janowski, Bethany A. et al.; "An oxysterol signalling pathway mediated by the nuclear receptor LXRα"; Nature, Oct. 24, 1996, pp. 728-731,vol. 383.
Lehmann, Jurgen M. et al; "Activation of the Nuclear Receptor LXR by Oxysterols Defines a New Hormone Response Pathway"; The Journal of Biological Chemistry, Feb. 7, 1997, pp. 3137-3140, vol. 272, No. 6.
Fu, Xuan et al.; "27-Hydroxycholesterol is an Endogenous Ligand for Liver X Receptor in Cholesterol-loaded Cells"; The Journal of Biological Chemistry, Oct. 19, 2001, pp. 38378-38387, vol. 276, No. 42.
Auboeuf, Didier et al.; "Tissue Distribution and Quantification of the Expression of mRNAs of Peroxisome Proliferator-Activated Receptors and Liver X Receptor-α in Humans"; Diabetes, Aug. 1997, pp. 1319-1327, vol. 46.
Lu, Timothy T. et al.; "Orphan Nuclear Receptors as eLiXiRs and FiXeRs of Sterol Metabolism"; The Journal of Biological Chemistry, Oct. 12, 2001, pp. 37735-37738, vol. 276, No. 41.
Zelcer, Noam et al.; "Liver X receptors as integrators of metabolic and inflammatory signaling"; The Journal of Clinical Investigation, Mar. 2006, pp. 607-614, vol. 116, No. 3.
Joseph, Sean B. et al.; "Reciprocal regulation of inflammation and lipid metabolism by liver X receptors"; Nature Medicine, Feb. 2003, pp. 213-219, vol. 9, No. 2. Geyeregger, R. et al.; "Liver X receptors in cardiovascular and metabolic disease"; Cellular and Molecular Life Sciences, 2006, pp. 524-539, vol. 63.
Peet, Daniel J. et al.; "Cholesterol and Bile Acid Metabolism Are Impaired in Mice Lacking the Nuclear Oxysterol Receptor LXRα"; Cell, May 29, 1998, pp. 693-704, vol. 93.
Alberti, S. et al.; "Hepatic cholesterol metabolism and resistance to dietary cholesterol in LXRβ-deficient mice"; The Journal of Clinical Investigation, Mar. 2001, pp. 565-573, vol. 107, No. 5.
Tangirala, Rajendra K. et al.; "Identification of macrophage liver X receptors as inhibitors of atherosclerosis"; PNAS, Sep. 3, 2002, pp. 11986-11901, vol. 99, No. 18.

(Continued)

*Primary Examiner* — Yong Chu
*Assistant Examiner* — Michael Barker
(74) *Attorney, Agent, or Firm* — Westerman, Hattori, Daniels & Adrian, LLP

(57) ABSTRACT

To provide a novel LXRβ agonist that is useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.
[Solving Means] A 2-oxochromene derivative represented by the following general formula (1) or salt thereof, or their solvate.

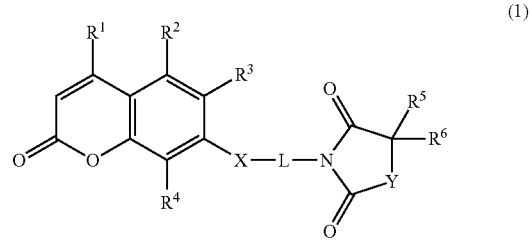

(1)

8 Claims, No Drawings

OTHER PUBLICATIONS

Terasaka, Naoki et al.; "T-0901317, a synthetic liver X receptor ligand, inhibits development of atherosclerosis in LDL receptor-deficient mice"; FEBS Letters, 2003, pp. 6-11, vol. 536.

Cao, Guoqing et al.; "Antidiabetic Action of a Liver X Receptor Agonist Mediated by Inhibition of Hepatic Gluconeogenesis" The Journal of Biological Chemistry, Jan. 10, 2003, pp. 1131-1136, vol. 278, No. 2.

Laffitte, Bryan A. et al.; "Activation of liver X receptor improves glucose tolerance through coordinate regulation of glucose metabolism in liver and adipose tissue"; PNAS, Apr. 29, 2003, pp. 5419-5424, vol. 100, No. 9.

Lala, Deepak S.; "The liver X receptors"; Current Opinion in Investigational Drugs, 2005, pp. 934-943, vol. 6 No. 9.

Groot, Pieter H. E. et al.; "Synthetic LXR agonists increase LDL in CETP species"; Journal of Lipid Research, 2005, pp. 2182-2191, vol. 46.

Schultz, Joshua R. et al.; "Role of LXRs in control of lipogenesis"; Genes & Development, 2000, pp. 2831-2838, vol. 14.

Lund, Erik G. et al.; "Liver X Receptor Agonists as Potential Therapeutic Agents for Dyslipidemia and Atherosclerosis"; Arterioscler Thromb Vasc Biol., 2003, pp. 1169-1177, vol. 23.

Bradley, Michelle N. et al.; "LXR: A nuclear receptor target for cardiovascular disease?"; Drug Discovery Today: Therapeutic Strateges, 2005, pp. 97-103, vol. 2, No. 2.

* cited by examiner

2-OXOCHROMENE DERIVATIVES

TECHNICAL FIELD

The present invention relates to a 2-oxochromene derivative which is a novel LXRβ agonist useful as a preventative and/or therapeutic agent for atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

BACKGROUND ART

Liver X receptor (LXR) is a nuclear receptor that was cloned as an orphan receptor whose ligand and function were both unknown. Subsequent study reported that some oxysterols including 22-(R)-hydroxycholesterol act as a ligand for LXR (non-patent documents 1 to 3). LXR, together with retinoid X receptor (RXR) which is another nuclear receptor, forms a heterodimer, to ligand-dependently control the transcription of a target gene.

As mammal LXR sub-types, two types of LXR genes (α and β) are known to exist. LXRα and LXRβ recognize the same sequence on a DNA and activate the transcription of a neighboring target gene. However, the expression-distributions of the two genes differ greatly. LXRα is specifically expressed on cholesterol metabolism-related tissues such as the liver, small intestines, or adipose tissues, whereas is LXRβ is expressed ubiquitously on almost all tissues that have been examined (non-patent documents 4 and 5).

Many of the group of genes identified as target genes of LXRs are genes (ApoE, CETP, and LPL) related to a reverse cholesterol transport (RCT), including ABC transporters (ABCA1, ABCG1, ABCG5, and ABCG8). Therefore, it is expected that the activation of LXRs elevates the expression of these genes and activates reverse cholesterol transport pathways, thereby increases cholesterol efflux from the periphery and then increases HDL cholesterols and also lowers cholesterol content at an arteriosclerosis-affected region (non-patent document 6).

Further, LXRs are reported to play an important role via NF-κB suppression, in the expression control of inflammatory mediators such as NO-synthase, cyclooxygenase-2 (COX-2), and interleukin-6 (IL-6) (non-patent document 7). It is well known that the inflammation is very important at an arteriosclerosis-affected region, and it is expected that LXR ligands or LXR agonists will prevent arteriosclerosis exacerbation due to the expression of macrophage-inflammatory mediators at the affected region (non-patent documents 6 and 8).

Further, LXRα- and LXRβ-deficient mice fed on high-cholesterol diet have been reported to show symptoms such as fatty liver and elevated LDL-cholesterol level as well as reduced HDL-cholesterol level in the blood as compared to the case of normal mice fed on high-cholesterol diet (non-patent documents 9 and 10). More specifically, it is strongly suggested that LXRs play an important role in cholesterol metabolism. Moreover, by analyzing the symptoms of arteriosclerosis mouse models having normal LXRα and LXRβ functions in the liver, small intestines and the like but lacking LXRα and LXRβ in macrophages, it has been revealed that LXRα and LXRβ activities in macrophages strongly affect the incidence of arteriosclerosis (non-patent document 11). Therefore, the activation of reverse cholesterol transport through the LXR activation especially in macrophages is considered important for the treatment of arteriosclerosis.

As for the applications, LXR regulators or LXR agonists disclosed in the prior art documents are reported to have been applied to diseases such as hypercholesterolemia and atherosclerosis (patent documents 1 and 2). Further, LDL-receptor-deficient mice loaded with high-fat food, and administered with LXR ligand, have been reported to show an elevated HDL cholesterol level, lowered VLDL and LDL cholesterol levels, and reduced area of arteriosclerosis-affected region (non-patent document 12).

Further, LXR ligands or LXR agonists are expected to control sugar metabolism in the liver and adipose tissues, and thus to improve diabetes (non-patent documents 6 and 8). Recently, it has been reported that an administration of LXR agonist improved insulin sensitivity and blood glucose level in diabetes animal models (non-patent documents 13 and 14). Moreover, it is indicated as a potential therapeutic drug for Alzheimer's disease, inflammatory diseases, or skin diseases (non-patent document 15).

LXR agonists, however, are reported to increase LDL cholesterol in animal species having cholesteryl ester transfer proteins (CETP) (non-patent document 16). Further, in animal experiments, it has been observed that LXR activation in the liver by the LXR agonist administration enhances fatty-acid and triglyceride syntheses through the transcriptional activation of enzymes that are important for fatty-acid synthesis, for example, fatty-acid synthase (FAS) or stearyl-CoA fatty-acid desaturase (SCD-1) (non-patent document 17). Meanwhile, nothing is disclosed in the prior art documents on LXR α/β selectivity in relation to the disclosed LXR regulators, LXR ligands, LXR agonists and the like.

Therefore, there have been demands for an ideal synthetic LXR-binding compound without a dyslipidemia-exacerbating effect which acts through an elevated fatty-acid and triglyceride syntheses, while maintaining the agonist activity for reverse cholesterol transport activation by ABC transporters and for increased cholesterol-efflux from macrophages. As one approach to solve the problem, a compound that selectively activates LXRβs is considered to have an ideal profile that is expected to suppress the activation of LXRα highly expressed on the liver, as compared to the LXR regulators disclosed in the prior art documents, and to suppress the concerned side-effects of fatty-acid and triglyceride synthesis elevations (non-patent documents 6, 8, 15, 18, and 19). However, because ligand-binding sites of LXRα and LXRβ are highly homologous, it is considered that the creation of a compound that acts differently on LXRα and LXRβ is not easy.

In fact, compounds having an LXR-agonist effect have been reported, such as a benzofuran-5-acetic acid derivative (patent document 3), 2-aminoquinazoline-4-one derivative (patent document 4), tetrahydroquinoline derivative (patent document 5), tetrahydrocarbazol derivative (patent document 6), isoquinoline derivative (patent document 7), and naphthalene derivative (patent document 8), GW3965 that is an aromatic aminoalcohol derivative (Example 16 described in patent document 9), and T0901317 that is a benzenesulfonamide derivative (Example 12 described in patent document 10), but no agonist with high LXRβ selectivity has been reported to date and therefore an LXRβ selective compound has been awaited.

[Patent Document 1] Published Japanese translation of PCT international publication No. 2002-539155
[Patent Document 2] Published Japanese translation of PCT international publication No. 2004-509161
[Patent Document 3] WO2003/82192
[Patent Document 4] WO2004/24161
[Patent Document 5] WO2004/72046

[Patent Document 6] U.S Patent publication No. 2005/215577
[Patent Document 7] WO2004/58717
[Patent Document 8] WO2005/23188
[Patent Document 9] WO2002/24632
[Patent Document 10] WO2000/54759
[Non-patent Document 1] Janowski et al., Nature, 383, pp. 728-731, 1996
[Non-patent Document 2] Lehmann et al., J. Biol. Chem., 272, pp. 3137-3140, 1997
[Non-patent Document 3] Fu et al., J. Biol. Chem., 276, pp. 38378-38387, 2001
[Non-patent Document 4] Auboeuf et al., Diabetes, 46, pp. 1319-1327, 1997
[Non-patent Document 5] Lu et al., J. Biol. Chem., 276, pp. 37735-37738, 2001
[Non-patent Document 6] Zelcer et al., J. Clin. Invest., 116, pp. 607-614, 2006
[Non-patent Document 7] Joseph et al., Nat. Med., 9, pp. 213-219, 2003
[Non-patent Document 8] Geyeregger et al., Cell. Mol. Life. Sci. 63, pp. 524-539, 2006
[Non-patent Document 9] Peet et al., Cell, 93, pp. 693-704, 1998
[Non-patent Document 10] Alberti et al., J. Clin. Invest., 107, pp. 565-573, 2001
[Non-patent Document 11] Tangirala et al., Proc. Natl. Acad. Sci. USA, 99, pp. 11896-11901, 2002
[Non-patent Document 12] Terasaka et al., FEBS Lett., 536, pp. 6-11, 2003
[Non-patent Document 13] Cao et al., J. Biol. Chem., 278, pp. 1131-1136, 2003
[Non-patent Document 14] Laffitte et al., Proc. Natl. Acad. Sci. USA, 100, pp. 5419-5424, 2003
[Non-patent Document 15] Lala et al., Curr. Opin. Investig. Drugs, 6, pp. 934-943, 2005
[Non-patent Document 16] Groot et al., J. Lipid Res., 46, pp. 2182-2191, 2005
[Non-patent Document 17] Schultz et al., Genes Dev., 14, pp. 2831-2838, 2000
[Non-patent Document 18] Lund et al., Arterioscler. Thromb. Vasc. Biol., 23, pp. 1169-1177, 2003
[Non-patent Document 19] Bradley et al., Drug Discov. Today Ther. Strateg. 2, pp. 97-103, 2005

DISCLOSURE OF THE INVENTION

Problem to be Solved by the Invention

Thus, the object of the present invention is to prepare a novel compound that exhibits an agonist activity with high LXRβ selectivity.

Means to Solve the Problem

The present inventors made a keen study to achieve the above object and consequently, found that a 2-oxochromene derivative represented by general formula (1) described hereinbelow has an agonist activity with high LXRβ selectivity, and thus completed the present invention.

More specifically, the present invention relates to
[1] a 2-oxochromene derivative represented by the following general formula (1) or salt thereof, or their solvate:

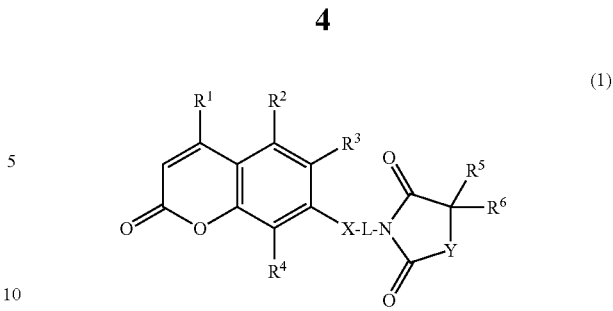

(1)

(wherein $R^1$ represents a halo $C_{1-8}$ alkyl group; $R^2$, $R^3$, and $R^4$ are either same or different and represent a hydrogen atom, halogen atom, $C_{1-8}$ alkyl group, halo $C_{1-8}$ alkyl group, $C_{2-8}$ alkenyl group, $C_{2-8}$ alkynyl group, $C_{1-8}$ alkoxy group, $C_{1-8}$ acyl group, nitro group, cyano group, carboxyl group, carbamoyl group, or $C_{6-10}$ aryl $C_{1-8}$ alkyl group, wherein the $C_{6-10}$ aryl may have 1 to 3 substituents selected from the following group A; $R^5$ and $R^6$ are either same or different and represent a hydrogen atom, $C_{1-8}$ alkyl group, $C_{3-8}$ cycloalkyl group, halo $C_{1-8}$ alkyl group, $C_{6-10}$ aryl group or 5- to 11-membered heterocyclic group, wherein the $C_{6-10}$ aryl group and 5- to 11-membered heterocyclic group may have 1 to 3 substituents selected from the following group A, and $R^5$ and $R^6$ may together form a $C_{3-8}$ cycloalkyl ring; L represents a $C_{2-10}$ alkyl chain, $C_{2-10}$ alkenyl chain, or $C_{2-6}$ alkyl-O—$C_{2-6}$ alkyl chain; X represents —O— or —N($R^7$)—; $R^7$ represents a hydrogen atom or $C_{1-8}$ alkyl group; Y represents an O, S, —CH($R^8$)—, —CH$_2$CH($R^9$)—, —CH$_2$O—, or —N($R^{10}$)—; $R^8$ and $R^9$ are either same or different and represent a hydrogen atom or $C_{1-8}$ alkyl group; $R^{10}$ represents a hydrogen atom, $C_{1-8}$ alkyl group that may be substituted with a $C_{1-8}$ alkoxycarbonyl group, halo $C_{1-8}$ alkyl group, $C_{6-10}$ aryl group, or 5- to 11-membered heterocyclic group, wherein the $C_{6-10}$ aryl group and 5- to 11-membered heterocyclic group may have 1 to 3 substituents selected from the following group A),

[Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, $C_{1-8}$ alkoxy group, halo $C_{1-8}$ alkoxy group, $C_{1-8}$ acyl group, nitro group, amino group, mono $C_{1-6}$ alkylamino group, di $C_{1-6}$ alkylamino group, cyano group, hydroxy group, carboxyl group, $C_{1-8}$ alkoxycarbonyl group, carbamoyl group, $C_{6-10}$ aryl group, 5- to 11-membered heterocyclic group, $C_{1-6}$ alkylthio group, $C_{1-6}$ alkylsulfonyl group, $C_{6-10}$ arylthio group, $C_{6-10}$ arylsulfonyl group, tetrahydropyranyloxy group, and $C_{1-6}$ alkylenedioxy group];

[2] a medicine containing the 2-oxochromene derivative or salt thereof, or their solvate according to [1] as an active ingredient;

[3] the medicine according to [2], which is a preventative and/or therapeutic agent for atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease;

[4] an LXR regulator containing the 2-oxochromene derivative or salt thereof, or their solvate according to [1] as an active ingredient;

[5] a pharmaceutical composition consisting of the 2-oxochromene derivative or salt thereof, or their solvate according to [1] and a pharmaceutically acceptable carrier;

[6] a method for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease, which method comprises administering an effective amount of the 2-oxochromene derivative or salt thereof, or their solvate according to [1] to a patient in need of the treatment;

[7] use of the 2-oxochromene derivative or salt thereof, or their solvate according to [1] for a production of a formulation for preventing and/or treating atherosclerosis, arteriosclerosis resulting from diabetes, dyslipidemia, hypercholesterolemia, lipid-related diseases, inflammatory diseases that are caused by inflammatory cytokines, skin diseases, diabetes, or Alzheimer's disease.

EFFECT OF THE INVENTION

The 2-oxochromene derivative represented by general formula (1) of the present invention has an LXRβ agonist effect and is useful as a preventative and/or therapeutic agent for atherosclerosis, arteriosclerosis such as those resulting from diabetes; dyslipidemia; hypercholesterolemia; lipid-related diseases; inflammatory diseases caused by inflammatory cytokines, such as rheumatoid arthritis, osteoarthritis, allergic diseases, asthma, sepsis, psoriasis, and osteoporosis; autoimmune diseases such as systemic erythematosus, ulcerative colitis, and Crohn's disease; cardiovascular diseases such as ischemic cardiac disease and heart failure; cerebrovascular diseases; kidney diseases; diabetes; diabetes complications such as retinopathy, nephropathy, nerve disease, and coronary arterial disease; skin diseases such as allergic skin disease; obesity; nephritis; hepatitis; cancer; or Alzheimer's disease, and more preferably, as a preventative and/or therapeutic agent for atherosclerosis, arteriosclerosis such as those resulting from diabetes, dyslipidemia, hypercholesterolemia, lipid-related diseases, inflammatory diseases that are caused by inflammatory cytokines, skin diseases such as allergic skin diseases, diabetes, or Alzheimer's disease.

DETAILED DESCRIPTION OF THE INVENTION

The terms in the present invention are defined as follows.

In the present invention, examples of a "halogen" atom in the halogen atom, halo $C_{1-8}$ alkyl group, or halo $C_{1-8}$ alkoxy group include a fluorine atom, chlorine atom, bromine atom, and iodine atom.

In the present invention, a "$C_{1-8}$ alkyl group" means a straight-chained or branched-chained alkyl group with 1 to 8 carbons, and the examples include a methyl group, ethyl group, n-propyl group, isopropyl group, n-butyl group, isobutyl group, t-butyl group, n-pentyl group, isopentyl group, neopentyl group, 2-methylbutyl group, 2,2-dimethylpropyl group, n-hexyl group, isohexyl group, n-heptyl group, and n-octyl group.

In the present invention, a "halo $C_{1-8}$ alkyl group" means a $C_{1-8}$ alkyl group to which, preferably 1 to 9 halogen atoms are bound, and the examples include trifluoromethyl group, 2-fluoroethyl group, 2-chloroethyl group, 2-bromoethyl group, 3-fluoropropyl group, 3-chloropropyl group, 4-fluorobutyl group, 4-chlorobutyl group, 2,2,2-trifluoroethyl group, 3,3,3-trifluoropropyl group, pentafluoroethyl group, and 2,2,2-trifluoro-1-trifluoromethylethyl group.

In the present invention, a "$C_{2-8}$ alkenyl group" means a straight-chained or branched-chained alkenyl group with 2 to 8 carbons, having a carbon-carbon double bond at any one or more sites on the alkyl chain. The examples include an ethenyl group, prop-1-en-1-yl group, prop-2-en-1-yl group, prop-1-en-2-yl group, but-1-en-1-yl group, but-2-en-1-yl group, but-3-en-1-yl group, but-1-en-2-yl group, but-3-en-2-yl group, pent-1-en-1-yl group, pent-4-en-1-yl group, pent-1-en-2-yl group, pent-4-en-2-yl group, 3-methyl-but-1-en-1-yl group, hex-1-en-1-yl group, hex-5-en-1-yl group, hept-1-en-1-yl group, hept-6-en-1-yl group, oct-1-en-1-yl group, and oct-7-en-1-yl group.

In the present invention, a "$C_{2-8}$ alkynyl group" means a straight-chained or branched-chained alkynyl group with 2 to 8 carbons, having a carbon-carbon triple bond at any one or more sites on the alkyl chain. The examples include an ethynyl group, prop-1-yn-1-yl group, prop-2-yn-1-yl group, but-1-yn-1-yl group, but-3-yn-1-yl group, 1-methyl-prop-2-yn-1-yl group, pent-1-yn-1-yl group, pent-4-yn-1-yl group, hex-1-yn-1-yl group, and hex-5-yn-1-yl group.

Specific examples of a "$C_{1-8}$ alkoxy group" in the present invention include a methoxy group, ethoxy group, n-propoxy group, isopropoxy group, n-butoxy group, isobutoxy group, sec-butoxy group, tert-butoxy group, n-pentoxy group, isopentoxy group, neopentoxy group, 1-methylbutoxy group, 1-ethylpropoxy group, n-hexyloxy group, isohexyloxy group, 4-methylpentoxy group, 3-methylpentoxy group, 2-methylpentoxy group, 1-methylpentoxy group, 3,3-dimethylbutoxy group, 2,2-dimethylbutoxy group, 1,1-dimethylbutoxy group, 1,2-dimethylbutoxy group, 1,3-dimethylbutoxy group, 2,3-dimethylbutoxy group, 1-ethylbutoxy group, and 2-ethylbutoxy group.

In the present invention, a "halo $C_{1-8}$ alkoxy group" means a group wherein the aforementioned halo $C_{1-8}$ alkyl group is bound to an oxygen atom, and the examples include a trifluoromethoxy group, 2-fluoroethoxy group, 2-chloroethoxy group, 2-bromoethoxy group, 3-fluoropropoxy group, 3-chloropropoxy group, 4-fluorobutoxy group, 4-chlorobutoxy group, 2,2,2-trifluoroethoxy group, 3,3,3-trifluoropropoxy group, pentafluoroethoxy group, and 2,2,2-trifluoro-1-(trifluoromethyl)ethoxy group.

In the present invention, examples of a "$C_{1-8}$ acyl group" include a formyl group, acetyl group, propionyl group, butyryl group, isobutyryl group, valeryl group, isovaleryl group, and pivaloyl group.

In the present invention, a "$C_{6-10}$ aryl $C_{1-8}$ alkyl group" means a group wherein the $C_{6-10}$ aryl group mentioned hereinbelow and the abovementioned $C_{1-8}$ alkyl group are bound. The examples include a benzyl group, phenethyl group, 3-phenyl-n-propyl group, 4-phenyl-n-butyl group, 5-phenyl-n-pentyl group, 8-phenyl-n-octyl group, and naphthylmethyl group.

In the present invention, a "$C_{3-8}$ cycloalkyl group," and a "$C_{3-8}$ cycloalkyl" in a $C_{3-8}$ cycloalkyl ring mean an alkyl group with 3 to 8-carbons having a cyclic moiety. The examples include a cyclopropyl group, cyclobutyl group, cyclopentyl group, cyclohexyl group, cycloheptyl group, cyclooctyl group, cyclopropylmethyl group, and cyclohexylmethyl group, and preferably a "$C_{3-6}$ cycloalkyl group" with 3 to 6 carbons.

In the present invention, a "$C_{6-10}$ aryl group," and a "$C_{6-10}$ aryl" in a $C_{6-10}$ aryl $C_{1-8}$ alkyl group mean a monocyclic or polycyclic aryl group with 6 to 10 carbons. Here, a polycyclic aryl group encompasses partially saturated groups in addition to fully unsaturated groups. The examples include a phenyl group, naphthyl group, azulenyl group, indenyl group, indanyl group, and tetralinyl group.

In the present invention, a "5- to 11-membered heterocyclic group" means a 5- to 11-membered aromatic heterocycle, saturated heterocycle, unsaturated heterocycle or a condensed heterocycle made by a condensation of the above heterocycles and a benzene ring, wherein the above heterocycles contain 1 to 3 heteroatoms selected from a nitrogen atom, oxygen atom and sulfur atom in addition to a carbon atom as atoms constituting the ring. The examples include a 2-furyl group, 3-furyl group, 2-thienyl group, 3-thienyl group, pyrrol-1-yl group, pyrrol-2-yl group, pyrrol-3-yl group, pyridin-2-yl group, pyridin-3-yl group, pyridin-4-yl group, pyrazin-2-yl group, pyrazin-3-yl group, pyrimidin-2-yl group, pyrimidin-4-yl group, pyrimidin-5-yl group, pyrimidin-6-yl group, pyridazin-3-yl group, pyridazin-4-yl group, 1,3-benzodioxol-4-yl group, 1,3-benzodioxol-5-yl group, 1,4-benzodioxan-5-yl group, 1,4-benzodioxan-6-yl group, 3,4-dihydro-2H-1,5-benzodioxepin-6-yl group, 3,4-dihydro-2H-1,5-benzodioxepin-7-yl group, 2,3-dihydrobenzofuran-4-yl group, 2,3-dihydrobenzofuran-5-yl group, 2,3-dihydrobenzofuran-6-yl group, 2,3-dihydrobenzofuran-7-yl group, benzofuran-2-yl group, benzofuran-3-yl group, benzofuran-4-yl group, benzofuran-5-yl group, benzofuran-6-yl group, benzofuran-7-yl group, benzothiophen-2-yl group, benzothiophen-3-yl group, benzothiophen-4-yl group, benzothiophen-5-yl group, benzothiophen-6-yl group, benzothiophen-7-yl group, quinoxalin-2-yl group, quinoxalin-5-yl group, quinoxalin-6-yl group, indol-1-yl group, indol-2-yl group, indol-3-yl group, indol-4-yl group, indol-5-yl group, indol-6-yl group, indol-7-yl group, isoindol-1-yl group, isoindol-2-yl group, isoindol-4-yl group, isoindol-5-yl group, isoindol-6-yl group, isoindol-7-yl group, isobenzofuran-1-yl group, isobenzofuran-4-yl group, isobenzofuran-5-yl group, isobenzofuran-6-yl group, isobenzofuran-7-yl group, chromen-2-yl group, chromen-3-yl group, chromen-4-yl group, chromen-5-yl group, chromen-6-yl group, chromen-7-yl group, chromene-8-yl group, imidazol-1-yl group, imidazol-2-yl group, imidazol-4-yl group, imidazol-5-yl group, pyrazol-1-yl group, pyrazol-3-yl group, pyrazol-4-yl group, pyrazol-5-yl group, thiazol-2-yl group, thiazol-4-yl group, thiazol-5-yl group, oxazol-2-yl group, oxazol-4-yl group, oxazol-5-yl group, isoxazol-3-yl group, isoxazol-4-yl group, isoxazol-5-yl group, pyrrolidin-2-yl group, pyrrolidin-3-yl group, benzoimidazol-1-yl group, benzoimidazol-2-yl group, benzoimidazol-4-yl group, benzoimidazol-5-yl group, benzothiazol-2-yl group, benzothiazol-4-yl group, benzothiazol-5-yl group, benzoxazol-2-yl group, benzoxazol-4-yl group, benzoxazol-5-yl group, quinolin-2-yl group, quinolin-3-yl group, quinolin-4-yl group, quinolin-5-yl group, quinolin-6-yl group, quinolin-7-yl group, quinolin-8-yl group, isoquinolin-1-yl group, isoquinolin-3-yl group, isoquinolin-4-yl group, isoquinolin-5-yl group, isoquinolin-6-yl group, isoquinolin-7-yl group, isoquinolin-8-yl group, 1,3,4-thiadiazol-2-yl group, morpholino group, 1,2,3-triazol-1-yl group, 1,2,3-triazol-4-yl group, 1,2,3-triazol-5-yl group, 1,2,4-triazol-1-yl group, 1,2,4-triazol-3-yl group, 1,2,4-triazol-5-yl group, tetrazol-1-yl group, tetrazol-2-yl group, indolin-4-yl group, indolin-5-yl group, indolin-6-yl group, indolin-7-yl group, 1,2,3,4-tetrahydroquinolin-5-yl group, 1,2,3,4-tetrahydroquinolin-6-yl group, 1,2,3,4-tetrahydroquinolin-7-yl group, 1,2,3,4-tetrahydroquinolin-8-yl group, 1,2,3,4-tetrahydroisoquinolin-5-yl group, 1,2,3,4-tetrahydroisoquinolin-6-yl group, 1,2,3,4-tetrahydroisoquinolin-7-yl group, and 1,2,3,4-tetrahydroisoquinolin-8-yl group.

Specific examples of a "mono $C_{1-6}$ alkylamino group" of the present invention include a methylamino group, ethylamino group, n-propylamino group, isopropylamino group, n-butylamino group, sec-butylamino group, tert-butylamino group, n-pentylamino group, isopentylamino group, neopentylamino group, 1-methylbutylamino group, 1-ethylpropylamino group, n-hexylamino group, isohexylamino group, 4-methylpentylamino group, 3-methylpentylamino group, 2-methylpentylamino group, 1-methylpentylamino group, 3,3-dimethylbutylamino group, 2,2-dimethylbutylamino group, 1,1-dimethylbutylamino group, 1,2-dimethylbutylamino group, 1,3-dimethylbutylamino group, 2,3-dimethylbutylamino group, 1-ethylbutylamino group, and 2-ethylbutylamino group.

Specific examples of a "di $C_{1-6}$ alkylamino group" of the present invention include a dimethylamino group, methylethylamino group, diethylamino group, methyl-n-propylamino group, ethyl-n-propylamino group, di-n-propylamino group, methyl isopropylamino group, ethyl isopropylamino group, diisopropylamino group, methyl-n-butylamino group, ethyl-n-butylamino group, n-propyl-n-butylamino group, di-n-butylamino group, di-sec-butylamino group, di-tert-butylamino group, dipentylamino group, and dihexylamino group.

Specific examples of a "$C_{1-6}$ alkylthio group" of the present invention include a methylthio group, ethylthio group, n-propylthio group, isopropylthio group, n-butylthio group, isobutylthio group, sec-butylthio group, tert-butylthio group, n-pentylthio group, isopentylthio group, neopentylthio group, 1-methylbutylthio group, 1-ethylpropylthio group, n-hexylthio group, isohexylthio group, 4-methylpentylthio group, 3-methylpentylthio group, 2-methylpentylthio group, 1-methylpentylthio group, 3,3-dimethylbutylthio group, 2,2-dimethylbutylthio group, 1,1-dimethylbutylthio group, 1,2-dimethylbutylthio group, 1,3-dimethylbutylthio group, 2,3-dimethylbutylthio group, 1-ethylbutylthio group, and 2-ethylbutylthio group.

Specific examples of a "$C_{1-16}$ alkylsulfonyl group" of the present invention include a methylsulfonyl group, ethylsulfonyl group, n-propylsulfonyl group, isopropylsulfonyl group, n-butylsulfonyl group, isobutylsulfonyl group, sec-butylsulfonyl group, tert-butylsulfonyl group, n-pentylsulfonyl group, isopentylsulfonyl group, neopentylsulfonyl group, 1-methylbutylsulfonyl group, 1-ethylpropylsulfonyl group, n-hexylsulfonyl group, isohexylsulfonyl group, 4-methylpentylsulfonyl group, 3-methylpentylsulfonyl group, 2-methylpentylsulfonyl group, 1-methylpentylsulfonyl group, 3,3-dimethylbutylsulfonyl group, 2,2-dimethylbutylsulfonyl group, 1,1-dimethylbutylsulfonyl group, 1,2-dimethylbutylsulfonyl group, 1,3-dimethylbutylsulfonyl group, 2,3-dimethylbutylsulfonyl group, 1-ethylbutylsulfonyl group, and 2-ethylbutylsulfonyl group.

Specific examples of a "$C_{6-10}$ arylthio group" of the present invention include a phenylthio group, naphthylthio group, and azulenylthio group.

Specific examples of a "$C_{6-10}$ arylsulfonyl group" of the present invention include a benzenesulfonyl group, p-toluenesulfonyl group, p-chlorobenzenesulfonyl group, naphthalen-1-yl-sulfonyl group, and naphthalen-2-yl-sulfonyl group.

Specific examples of a "$C_{1-6}$ alkylenedioxy group" of the present invention include a methylenedioxy group, ethylenedioxy group, trimethylenedioxy group, tetramethylenedioxy group, pentamethylenedioxy group, and hexamethylenedioxy group.

Specific examples of a "$C_{1-8}$ alkoxycarbonyl group" of the present invention include a methoxycarbonyl group, ethoxycarbonyl group, n-propoxycarbonyl group, isopropoxycarbonyl group, n-butoxycarbonyl group, isobutoxycarbonyl group, sec-butoxycarbonyl group, tert-butoxycarbonyl group, n-pentoxycarbonyl group, isopentoxycarbonyl group, neopentoxycarbonyl group, 1-methylbutoxycarbonyl group, 1-ethylpropoxycarbonyl group, n-hexyloxycarbonyl group, isohexyloxycarbonyl group, 4-methylpentoxycarbonyl group, 3-methylpentoxycarbonyl group, 2-methylpentoxycarbonyl group, 1-methylpentoxycarbonyl group, 3,3-dimethylbutoxycarbonyl group, 2,2-dimethylbutoxycarbonyl group, 1,1-dimethylbutoxycarbonyl group, 1,2-dimethylbutoxycarbonyl group, 1,3-dimethylbutoxycarbonyl group, 2,3- dimethylbutoxycarbonyl group, 1-ethylbutoxycarbonyl group, and 2-ethylbutoxycarbonyl group.

In the present invention, a "$C_{2-10}$ alkyl chain" means a divalent hydrocarbon chain with 2 to 10 carbons having a straight-chain or a branch, and the examples include an ethylene chain, trimethylene chain, methylethylene chain, tetramethylene chain, 1,2-dimethylethylene chain, pentamethylene chain, 1-methyltetramethylene chain, 2-methyltetramethylene chain, hexamethylene chain, heptamethylene chain, octamethylene chain, nonamethylene chain, and decamethylene chain.

In the present invention, a "$C_{2-10}$ alkenyl chain" means a straight-chained or branched-chained divalent hydrocarbon chain with 2 to 10 carbons having a carbon-carbon double bond at any one or more sites on the above "$C_{2-10}$ alkyl chain," and the examples include a vinylene chain, propenylene chain, methylvinylene chain, butenylene chain (for example, 1-butenylene chain, 2-butenylene chain or the like), 1,2-dimethylvinylene chain, pentenylene chain, 1-methylbutenylene chain, 2-methylbutenylene chain, hexenylene chain, heptenylene chain, octenylene chain, nonenylene chain, decenylene chain, and isoplenylene chain.

In the present invention, a $C_{2-6}$ alkyl-O—$C_{2-6}$ alkyl chain means a chain wherein the above "$C_{2-6}$ alkyl chains" are bound via an oxygen atom. The examples include an ethylene-O-ethylene chain, ethylene-O-trimethylene chain, trimethylene-O-ethylene chain, and trimethylene-O-trimethylene chain.

Other groups that are not defined herein follow common definitions.

Followings are examples of the preferred modes of the present invention.

In general formula (1), the halo $C_{1-8}$ alkyl group of $R^1$ is more preferably a 2,2,2-trifluoroethyl group or trifluoromethyl group and particularly preferably a trifluoromethyl group.

In general formula (1), $R^2$ is preferably a hydrogen atom.

In general formula (1), $R^3$ is preferably a hydrogen atom, halogen atom, $C_{1-8}$ alkyl group, halo $C_{1-8}$ alkyl group, or $C_{6-10}$ aryl $C_{1-8}$ alkyl group, and more preferably a hydrogen atom or $C_{1-8}$ alkyl group.

In general formula (1), the halogen atom of $R^3$ is preferably a chlorine atom.

In general formula (1), the $C_{1-8}$ alkyl group of $R^3$ is preferably a straight-chained $C_{1-8}$ alkyl group such as a methyl group, ethyl group, n-propyl group, or n-butyl group, and particularly preferably an n-propyl group.

In general formula (1), the halo $C_{1-8}$ alkyl group of $R^3$ is preferably a straight-chained halo $C_{1-8}$ alkyl group wherein a plurality of fluorine atoms have been substituted, such as a trifluoromethyl group or 2,2,2-trifluoroethyl group.

In general formula (1), the $C_{6-10}$ aryl $C_{1-8}$ alkyl group of $R^3$ is preferably a benzyl group.

In general formula (1), $R^4$ is preferably a hydrogen atom, $C_{1-8}$ alkyl group, halo $C_{1-8}$ alkyl group, or $C_{2-8}$ alkenyl group, and more preferably a $C_{1-8}$ alkyl group.

In general formula (1), the $C_{1-8}$ alkyl group of $R^4$ is preferably a straight-chained $C_{1-8}$ alkyl group such as an ethyl group, n-propyl group, or n-butyl group, and particularly preferably an ethyl group or n-propyl group.

In general formula (1), the halo $C_{1-8}$ alkyl group of $R^4$ is preferably a straight-chained halo $C_{1-8}$ alkyl group wherein a plurality of fluorine atoms have been substituted, such as 2,2,2-trifluoromethyl group.

In general formula (1), the $C_{2-8}$ alkenyl group of $R^4$ is preferably a straight-chained $C_{2-8}$ alkenyl group such as a prop-1-en-1-yl group.

In general formula (1), $R^5$ and $R^6$ are preferably a hydrogen atom, $C_{1-8}$ alkyl group, halo $C_{1-8}$ alkyl group, $C_{3-8}$ cycloalkyl group, $C_{6-10}$ aryl group, or 5- to 11-membered heterocyclic group, and more preferably a $C_{1-8}$ alkyl group or $C_{6-10}$ aryl group. It is particularly preferable that either or both of $R^5$ and $R^6$ are a $C_{1-8}$ alkyl group.

In general formula (1), the $C_{1-8}$ alkyl group of $R^5$ and $R^6$ is preferably a methyl group, ethyl group, n-propyl group, n-butyl group, or t-butyl group, and particularly preferably a methyl group.

In general formula (1), the halo $C_{1-8}$ alkyl group of $R^5$ and $R^6$ is preferably a trifluoromethyl group.

In general formula (1), the $C_{3-8}$ cycloalkyl group of $R^5$ and is preferably a cyclopropyl group or cyclobutyl group.

In general formula (1), the $C_{6-10}$ aryl group of $R^5$ and $R^6$ is more preferably a phenyl group or naphthyl group. A substituent for the $C_{6-10}$ aryl group is preferably a "halogen atom" such as a fluorine atom, chlorine atom, and bromine atom; a "$C_{1-8}$ alkyl group" such as a methyl group, ethyl group, isopropyl group, t-butyl group, and sec-butyl group; a "halo $C_{1-8}$ alkyl group" such as a trifluoromethyl group; a "$C_{1-8}$ alkoxy group" such as a methoxy group, ethoxy group, n-propoxy group, isopropoxy group, and n-butoxy group; a "$C_{6-10}$ aryl group" such as a phenyl group; a "di $C_{1-6}$ alkylamino group" such as a dimethylamino group and diethylamino group; a "$C_{1-6}$ alkoxycarbonyl group" such as a t-butoxycarbonyl group; a "$C_{1-6}$ alkylenedioxy group" such as a methylenedioxy group and ethylenedioxy group; a nitro group, hydroxyl group, cyano group, carboxyl group, or tetrahydropyranyloxy group, and particularly preferably a "halogen atom" such as a fluorine atom and bromine atom; a "$C_{1-8}$ alkyl group" such as an ethyl group and isopropyl group; a "$C_{1-8}$ alkoxy group" such as a methoxy group and ethoxy group; or a "$C_{1-6}$ alkylenedioxy group" such as a methylenedioxy group and ethylenedioxy group.

In general formula (1), the 5- to 11-membered heterocyclic group of $R^5$ and $R^6$ is preferably a monocyclic 5- to 6-membered heterocyclic group such as a thienyl group, furyl group, and pyridyl group.

In general formula (1), a cyclopentyl ring is preferred when $R^5$ and $R^6$ together form a $C_{3-8}$ cycloalkyl ring.

In general formula (1), the "$C_{2-10}$ alkyl chain" of L is preferably a "$C_{2-6}$ alkyl chain" and particularly preferably a tetramethylene chain, pentamethylene chain, or hexamethylene chain.

In general formula (1), the "$C_{2-10}$ alkenyl chain" of L is preferably a "$C_{2-6}$ alkenyl chain" and particularly preferably a 2-butenyl chain.

In general formula (1), the "$C_{2-6}$ alkyl-O—$C_{2-6}$ alkyl chain" of L is preferably an ethylene-O-ethylene chain.

In general formula (1), X is preferably a —O—.

In general formula (1), the "$C_{1-8}$ alkyl group" of $R^7$ is preferably an n-butyl group.

In general formula (1), Y is preferably a —N($R^{10}$)—.

In general formula (1), the "$C_{1-8}$ alkyl group" of $R^8$ is preferably a methyl group.

In general formula (1), the "$C_{1-8}$ alkyl group" of $R^9$ is preferably a methyl group.

In general formula (1), $R^{10}$ is preferably a hydrogen atom or $C_{1-8}$ alkyl group.

In general formula (1), the "$C_{1-8}$ alkyl group that may be substituted with a $C_{1-6}$alkoxycarbonyl group" of $R^{10}$ is preferably, for example, a methyl group, ethyl group, n-propyl group, isopropyl group, 2-methoxycarbonylethyl group, 3-methoxycarbonylpropan-1-yl group, or 4-methoxycarbonylbutan-1-yl group, and particularly preferably a methyl group or ethyl group.

In general formula (1), the "halo $C_{1-8}$ alkyl group" of $R^{10}$ is preferably a 2,2,2-trifluoroethyl group.

In general formula (1), the "$C_{6-10}$ aryl group" of $R^{10}$ is preferably a phenyl group. Further, a substitutent for the $C_{6-10}$ aryl group is preferably a "halogen atom" such as a fluorine atom and chlorine atom; a "$C_{1-8}$ alkyl group" such as a methyl group and t-butyl group; a "halo $C_{1-8}$ alkyl group" such as a trifluoromethyl group; a "$C_{1-8}$ acyl group" such as an acetyl group; or a "$C_{1-6}$ alkylenedioxy group" such as a methylenedioxy group and ethylenedioxy group.

In general formula (1), the "5- to 11-membered heterocyclic group" of $R^{10}$ is preferably a "5 to 6-membered heterocyclic group" such as a 2-pyrazinyl group, 5-pyrimidinyl group and 2-pyridinyl group.

Examples of an addition salt of a 2-oxochromene derivative represented by general formula (1) include alkali metal salts such as sodium salt and potassium salt; alkaline earth metal salts such as calcium salt and magnesium salt; organic base salts such as ammonium salt and trialkylamine salt; mineral acid salts such as hydrochloride salt and sulfate; and organic acid salts such as acetate. Among these, sodium salt is preferred, but there is no particular limitation as long as it is a pharmaceutically acceptable salt.

Examples of a solvate of a 2-oxochromene derivative represented by general formula (1) include a hydrate.

When there is a geometric isomer or optical isomer of a compound of the present invention, such isomers are included in the scope of the present invention.

Compound (I) can be produced by various known methods without particular limitation, and for example, can be produced according to the following reaction process.

More specifically, by reacting a 7-substituted-2-oxochromene derivative shown by general formula (II) with a dihalide (III), a derivative shown by general formula (IV) is obtained. By reacting the obtained compound shown by general formula (IV) with an imide compound shown by general formula (V), a compound (I) can be produced. This reaction path shown by a chemical reaction formula is as follows:

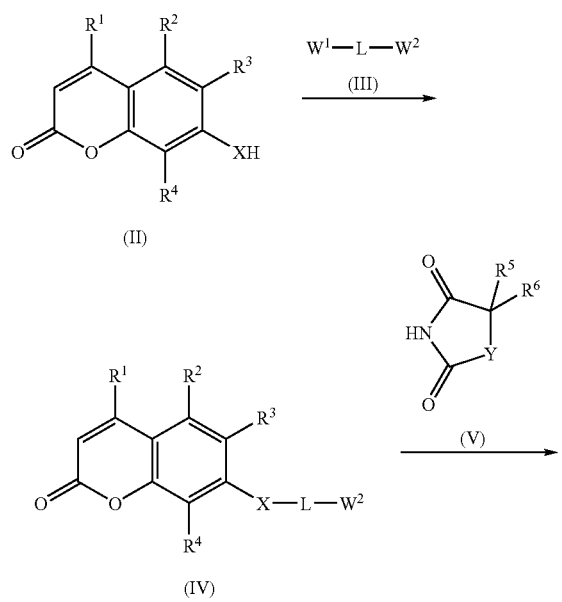

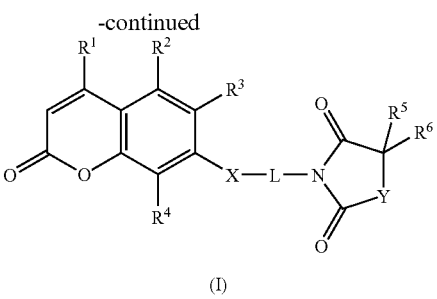

(wherein $R^1$ to $R^6$, X, and L have the same meaning as above and $W^1$ and $W^2$ show a halogen atom).

If an imide compound shown by general formula (V) has a reactive substituent, a compound of interest can be obtained by an addition of a protective group by a commonly used method (Protective Groups in Organic Synthesis Third Edition: John Wiley & Sons, Inc.; 1999) followed by a deprotection at an appropriate time.

By reacting a 7-substituted-2-oxochromene derivative shown by general formula (II) with excessive amounts of dihalide (III) in a solvent in the presence or absence of a base, a derivative of general formula (IV) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethylketone, water or the like. Further, a dihalide (III) can be used as a solvent. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; or organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium. A derivative of general formula (IV) which is a substance of interest can be obtained by conducting a reaction under the reaction conditions of −80 to 150° C., preferably of 0 to 100° C., for 1 minute to 5 days, preferably for 1 hour to 3 days.

By reacting the halide derivative (IV) obtained from the above reaction with an imide compound (V) in a solvent in the presence or absence of a base, a substance of interest (I) can be produced. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water or the like. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; or organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium. A substance of interest can be obtained by conducting a reaction under the reaction conditions of −80 to 150° C., preferably of 0 to 100° C., for 1 minute to 5 days, preferably for 1 hour to 3 days.

Further, a compound (I) can also be produced by reacting an imide compound shown by the above general formula (V) with a reagent shown by general formula (VI) to obtain an intermediate (VII), and then by further reacting with a 7-substituted-2-oxochromene derivative (II). This reaction path shown by a chemical reaction formula is as follows:

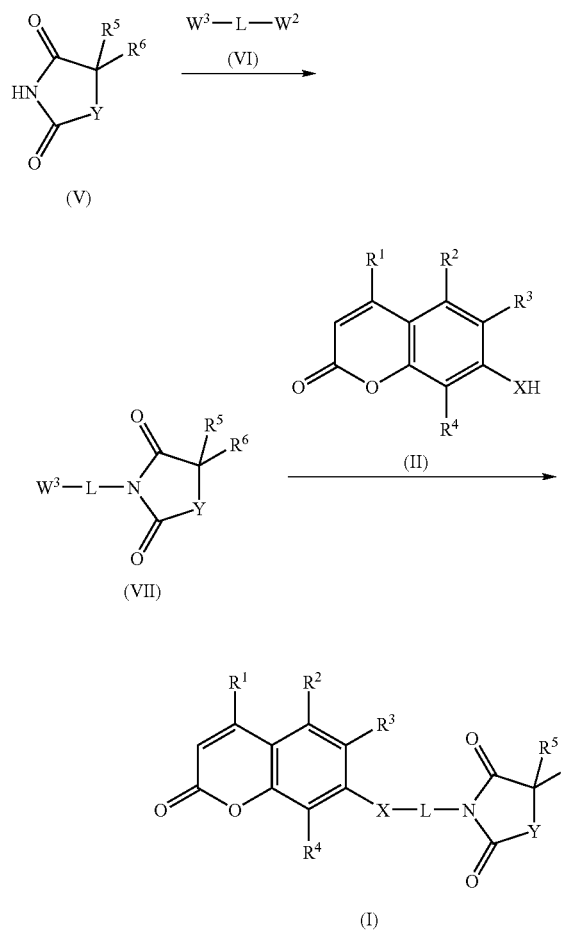

(wherein $R^1$ to $R^6$, X, and L have the same meaning as above, $W^2$ shows a halogen atom, and $W^3$ shows a halogen atom, aldehyde, aldehyde equivalent, or ketone).

The term an "aldehyde equivalent" refers to an aldehyde added with a protective group or to a substance that can be transformed into an aldehyde by a commonly used method (Comprehensive Organic Transformations Second Edition: John Wiley & Sons, Inc.; 1999). A commonly used method (Protective Groups in Organic Synthesis Third Edition: John Wiley & Sons, Inc.; 1999) can be used to add the protective group.

If an imide compound shown by general formula (V) has a reactive substituent, a compound of interest can be obtained by an addition of a protective group by a commonly used method (Protective Groups in Organic Synthesis Third Edition: John Wiley & Sons, Inc.; 1999), followed by a deprotection at an appropriate time.

By reacting an imide compound shown by general formula (V) with a reagent shown by general formula (VI) in a solvent in the presence or absence of a base, a derivative of general formula (VII) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, water or the like. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; or organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium. A derivative of general formula (VII) which is the substance of interest can be obtained by conducting a reaction under the reaction conditions of −80 to 150° C., preferably of 0 to 100° C., for 1 minute to 5 days, preferably for 1 hour to 3 days.

When $W^3$ is a halogen atom, a compound (I) can be produced by the same alkylation reaction as mentioned above.

Further, when X shows a —N($R^7$)—, a compound (I) can be produced using a reductive alkylation reaction with the use of a reagent shown by general formula (VII) in which $W^3$ is an aldehyde group. A reductive alkylation reaction can be conducted by a commonly used method (Comprehensive Organic Transformations Second Edition: John Wiley & Sons, Inc.; 1999).

A known method (Organic Reactions vol. 7, pp 1: John Wiley & Sons, Inc; 1953., Chem. Rev., 36. pp 1-62, 1945) can be referred to for a common method for producing a 2-oxochromene derivative.

A 7-substituted-2-oxochromene derivative shown by general formula (II) can be produced by various methods that are not particularly limited, and for example, can be produced by Pechmann condensation. This reaction path shown by a chemical reaction formula is as follows:

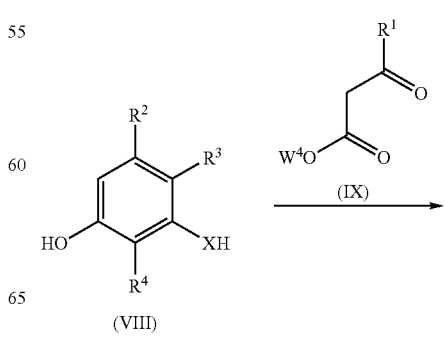

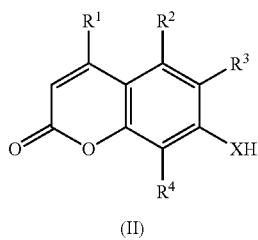

(II)

(wherein $R^1$ to $R^4$ and X have the same meaning as above and $W^4$ shows a hydrogen atom or lower alkyl group).

By reacting a derivative shown by general formula (VIII) with a β-ketoester or carboxylic acid (IX) in or without a solvent in the presence or absence of an acid, a substance of interest (II) can be produced. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, acetone or the like. The acid is not particularly limited, and for example, the followings can be used: sulfuric acid, hydrochloric acid, diphosphorus pentoxide, phosphorus oxychloride, polyphosphoric acid, or Lewis acids such as zinc chloride, aluminum chloride, titanium tetrachloride, and tin tetrachloride. A substance of interest can be obtained by conducting a reaction under the reaction conditions of −80 to 150° C., preferably of 0 to 100° C., for 1 minute to 5 days, preferably for 1 hour to 3 days.

Further, a 7-substituted-2-oxochromene derivative shown by general formula (II) can be produced by a functional-group transformation by a commonly used method (Comprehensive Organic Transformations Second Edition: John Wiley & Sons, Inc.; 1999).

For example, after halogenating a 2-oxochromene derivative shown by general formula (X), a substituent can be introduced by Suzuki-Miyaura coupling. This reaction path shown by a chemical reaction formula is as follows:

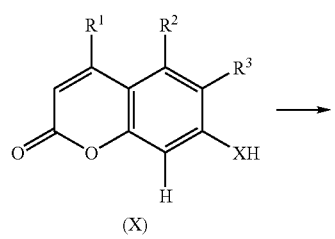

(X)

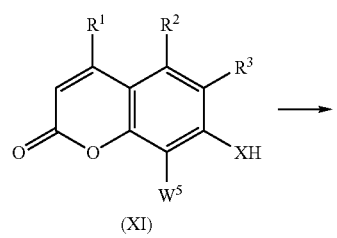

(XI)

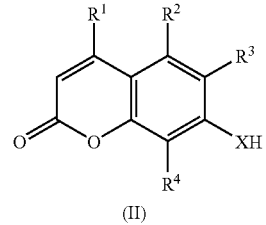

(II)

(wherein $R^1$ to $R^4$ and X have the same meaning as above and $W^5$ shows a halogen atom).

By reacting a 2-oxochromene derivative shown by general formula (X) with a halogenating agent in a solvent in the presence or absence of a base, a derivative of general formula (XI) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, methanol, ethanol, isopropanol, water or the like. Further, a halide agent or organic base can be used as a solvent. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium; or organic base compounds such as pyridine, triethylamine, 2,6-lutidine, and picoline. The halogenating agent is not particularly limited, and for example, chlorine, bromine, iodine, tetrabutylammonium chloride, tetrabutylammonium bromide, tetrabutylammonium iodide, N-chlorosuccinimide, N-bromosuccinimide, N-iodosuccinimide, carbon tetrabromide or the like can be used. Further, a halide salt such as potassium bromide, potassium iodide, sodium bromide, and sodium iodide can be oxidized with an oxidant such as a hydrogen peroxide solution or an aqueous solution of sodium hypochlorite to produce a halogenating agent in the system, which is to be used in the reaction. A derivative of general formula (XI), the substance of interest, can be obtained by conducting a reaction under the reaction conditions of −80 to 150° C., preferably of 0 to 100° C., for 1 minute to 5 days, preferably for 1 hour to 3 days.

By reacting a 2-oxochromene derivative shown by general formula (XI) with an organic metal compound in a solvent in the presence or absence of a base and in the presence of a catalyst, a derivative of general formula (II) which is a substance of interest can be obtained. The solvent is not particularly limited, and for example, the followings can be used independently or in combination: tetrahydrofuran, toluene, dioxane, N,N-dimethylformamide, N-methylpyrrolidone, dimethylsulfoxide, acetonitrile, propionitrile, acetone, methylethyl ketone, methanol, ethanol, isopropanol, water or the like. The base is not particularly limited, and for example, the followings can be used: alkali metal hydrides such as lithium hydride, sodium hydride, and potassium hydride; alkali metal hydroxides such as lithium hydroxide, sodium hydroxide, and potassium hydroxide; alkali metal carbonates such as lithium carbonate, sodium carbonate, potassium carbonate, and cesium carbonate; alcohol metallic salts such as sodium methoxide, potassium methoxide, sodium ethoxide, potassium ethoxide, sodium t-butoxide, and potassium t-butoxide; organic metals such as lithium diisopropylamide, sodium diisopropylamide, potassium diisopropylamide, lithium hexamethyldisilazide, sodium hexamethyldisilazide, potassium hexamethyldisilazide, n-butyllithium, s-butyllithium, and t-butyllithium; or fluoride salts such as tetraethylammonium fluoride, tetrabutylammonium fluoride, lithium fluoride, sodium fluoride, potassium fluoride, and cesium fluoride. The catalyst is not particularly limited, and for example, the followings can be used: a palladium reagent or the like such as [1,1'-bis(diphenylphosphino)ferrocene]dichloropalladium (II), bis(triphenylphosphine)palladium(II)diacetate, bis(triphenylphosphine)dichloropalladium(II), palladium(II)diacetate, and tetrakis(triphenylphosphine)palladium(O). The organic metal compound is not particularly limited, and an organic boron compound, organic zinc compound, organic tin compound or the like having $R^4$ can be used. Further, a halogenated metal such as copper bromide(I), copper iodide(I) or the like can be added to conduct a transmetalation and then used for the reaction. A derivative of general formula (II), the substance of interest, can be obtained by conducting a reaction under the reaction conditions of −80 to 150° C., preferably of 0 to 100° C., for 1 minute to 5 days, preferably for 1 hour to 3 days.

Further, after halogenating the 6-position of an 8-substituted-2-oxochromene derivative shown by general formula (XII), a substituent can be introduced. This reaction path shown by a chemical reaction formula is as follows:

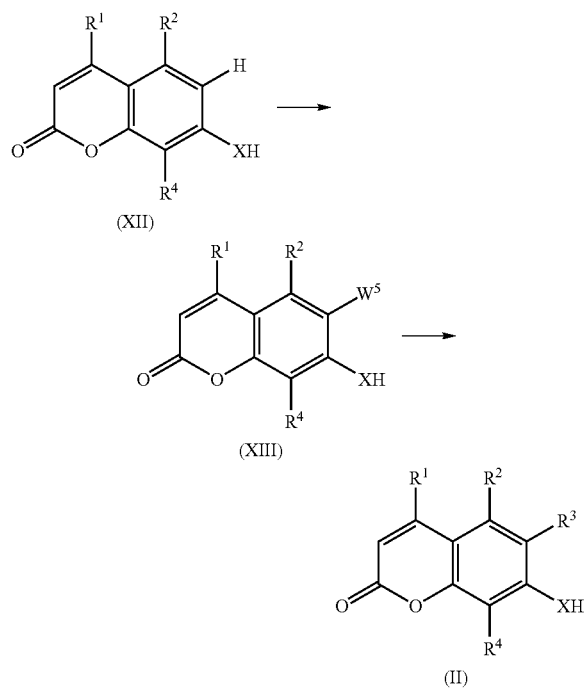

(wherein $R^1$ to $R^4$ and X have the same meaning as above and $W^5$ shows a halogen atom).

A derivative shown by general formula (VIII) can be produced using a known method (J. Med. Chem., 32, pp 807-826, 1989., J. Med. Chem., 38, pp 4411-4432, 1995, J. Med. Chem., 48, pp 2262-2265, 2005, WO2001/060807).

A 2-oxochromene derivative represented by general formula (1) of the present invention can be obtained by the above-mentioned methods, and further and optionally, can be purified using an ordinary purifying method such as recrystallization method and column chromatography. Moreover, the above derivative can optionally be processed into an above-mentioned desired salt or solvate by a usual method.

So obtained 2-oxochromene derivative represented by general formula (1) or salt thereof, or their solvate (hereinafter, sometimes collectively described as "compounds represented by general formula (1)") shows a superior LXRβ agonist effect as shown in test examples described hereinbelow, and is useful as an active ingredient of a preventative and/or therapeutic agent for diseases of animal including humans, resulting from abnormal cholesterol metabolism, for example, atherosclerosis; arteriosclerosis such as those resulting from diabetes; dyslipidemia; hypercholesterolemia; lipid-related diseases; inflammatory diseases that are caused by inflammatory cytokines; skin diseases such as allergic skin diseases; diabetes; or Alzheimer's disease.

The pharmaceutical composition of the present invention contains a 2-oxochromene derivative represented by general formula (1) or salt thereof, or their solvate. The pharmaceutical composition can be used independently, but generally, is used by formulating with a pharmaceutically acceptable carrier, additive and the like. The administration form of the pharmaceutical composition is not particularly limited, and can be selected as desired according to the therapeutic purpose. For example, the administration form can be any of oral preparation, injection, suppository, ointment, inhalation, eyedrops, nasal preparation, adhesive patch and the like. The pharmaceutical composition suitable for these administration forms can be produced according to a known method of drug formulation.

When prepared into a solid oral formulation, a compound represented by general formula (1) can be added with an excipient and optionally, further with a binder, disintegrant, lubricant, coloring agent, flavoring agent, odor improving agent or the like, and then processed into a tablet, coated tablet, granules, powder, capsule or the like by a usual method. The additive may be those commonly used in this field. Examples of the excipient include lactose, sucrose, sodium chloride, glucose, starch, calcium carbonate, Kaolin, microcrystalline cellulose, and silicate. Examples of the binder include water, ethanol, propanol, simple syrup, dextrose solution, starch solution, gelatin solution, carboxymethylcellulose, hydroxypropylcellulose, hydroxypropyl starch, methylcellulose, ethylcellulose, shellack, calcium phosphate, and polyvinylpyrrolidone. Examples of the disintegrant include dry starch, sodium alginate, powdered agar, sodium hydrogen carbonate, calcium carbonate, sodium lauryl sulfate, monoglyceride stearate, and lactose. Examples of the lubricant include purified talc, stearate, borax, polyethyleneglycol and the like. Examples of the flavoring agent include sucrose, orange peel, citric acid, and tartaric acid.

When prepared into a liquid oral formulation, a compound represented by general formula (1) can be added with a flavoring agent, buffer, stabilizer, odor improving agent or the like, and then processed into an internal liquid formulation, syrup, elixir or the like. The flavoring agent may be those mentioned above, and examples of the buffer include sodium citrate, and examples of the stabilizer include tragacanth, gum Arabic, and gelatin.

When prepared into an injection, a compound represented by general formula (1) can be added with a pH adjuster, buffer, stabilizer, isotonic agent, local anesthetic or the like, and then processed into a subcutaneous, intramuscular, and intravenous injection by a usual method. Examples of the pH adjuster and buffer include sodium citrate, sodium acetate, and sodium phosphate. Examples of the stabilizer include sodium pyrosulfite, EDTA, thioglycolic acid, and thiolactic acid. Examples of the local anesthetic include procaine hydrochloride and lidocaine hydrochloride. Examples of the isotonic agent include sodium chloride and glucose.

When prepared into a suppository, a compound represented by general formula (1) can be added with a known carrier for suppository, for example, with polyethyleneglycol, lanolin, cacao butter, fatty acid triglyceride and the like, and optionally, further with a surfactant such as Tween®, and then processed into a suppository by a usual method.

When prepared into an ointment, a compound represented by general formula (1) can be optionally formulated with a commonly used base, stabilizer, moisturizer, preservative or the like, and then mixed and formulated by a usual method. Examples of the base include liquid paraffin, white petrolatum, white beeswax, octyldodecyl alcohol, and paraffin. Examples of the preservative include methyl p-hydroxybenzoate, ethyl p-hydroxybenzoate, and propyl p-hydroxybenzoate.

In addition to the above, an inhalation, eye-drops, or nasal preparation can be produced by a usual method.

The dose of a compound represented by general formula (1) varies depending on the age, weight, symptom, administration form, the number of doses and the like, but generally, it is preferable to administer 2-oxochromene derivative represented by general formula (1) to an adult in an amount of 1 to 1000 mg per day as a single or several separate doses either orally or parenterally.

The present invention will be described further with reference to the following examples, while the scope of the present invention will not be limited to these examples.

Example 1

Preparation of 5-(2,3-dihydrobenzo[b][1,4]dioxin-6-yl)-5-methyl-3-[4-[2-oxo-8-propyl-4-(trifluoromethyl)-2H-chromen-7-yloxy]butyl]imidazolidine-2,4-dione a) Preparation of 7-hydroxy-8-propyl-4-(trifluoromethyl)-2H-chromen-2-one

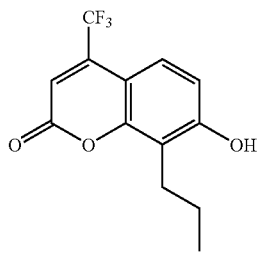

2-propylbenzene-1,3-diol (J. Med. Chem., 38, pp 4411-4432, 1995) (3.65 g, 24.0 mmol), zinc chloride (3.60 g, 26.4 mmol), and ethyl 4,4,4-trifluoroacetoacetate (4.86 g, 26.4 mmol) were stirred overnight at 110° C. The reaction solution was added with water and extracted with ethyl acetate. Subsequently, the organic layer was washed with saturated saline, dried using anhydrous sodium sulfate, and concentrated under vacuum. The obtained residue was purified using silica-gel chromatography (chloroform) and then recrystallized with chloroform, and 5.01 g of the title compound (yield 77%) was obtained as pale-brown crystalline powder.

$^1$H-NMR (CDCl$_3$) δ: 1.00 (3H, t, J=7.4 Hz), 1.65 (2H, sixtet, J=7.5 Hz), 2.84 (2H, t, J=7.8 Hz), 5.95 (1H, s), 6.63 (1H, s), 6.85 (1H, d, J=8.6 Hz), 7.48 (1H, dd, J=8.6 Hz).

b) Preparation of 7-(4-bromobutoxy)-8-propyl-4-(trifluoromethyl)-2H-chromen-2-one

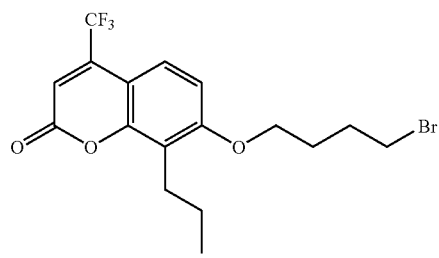

An N,N-dimethylformamide (5 mL) solution of 7-hydroxy-8-propyl-4-(trifluoromethyl)-2H-chromen-2-one (500 mg, 1.84 mmol), 1,4-dibromobutane (2.19 mL, 18.36 mmol), and potassium carbonate (375 mg, 2.76 mmol) was stirred overnight at room temperature. The reaction solution was added with water and extracted with ethyl acetate. Subsequently, the organic layer was washed with saturated saline, dried using anhydrous sodium sulfate, and concentrated under vacuum. The obtained residue was purified using silica-gel chromatography (hexane:ethyl acetate=10:1), and the title compound (0.79 g) was obtained as yellow oil.

$^1$H-NMR (CDCl$_3$) δ: 0.98 (3H, t, J=7.4 Hz), 1.59 (2H, sextet, J=7.4 Hz), 1.98-2.16 (4H, m), 2.83 (2H, t, J=7.6 Jz), 3.53 (2H, t, J=6.2 Hz), 4.14 (2H, t, J=5.7 Hz), 6.59 (1H, s), 6.90 (1H, d, J=9.5 Hz), 7.54 (1H, m).

c) Preparation of 5-(2,3-dihydrobenzo[b][1,4]dioxin-6-yl)-5-methyl-3-[4-[2-oxo-8-propyl-4-(trifluoromethyl)-2H-chromen-7-yloxy]butyl]imidazolidine-2,4-dione

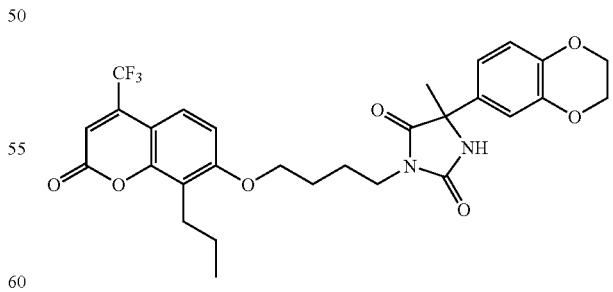

An N,N-dimethylformamide (2 mL) solution of 7-(4-bromobutoxy)-8-propyl-4-(trifluoromethyl)-2H-chromen-2-one (30 mg, 0.074 mmol) was added with potassium carbonate (20.4 mg, 0.148 mmol) and 5-(2,3-dihydrobenzo[b][1,4]dioxin-6-yl)-5-methylimidazolidine-2,4-dione (27.4 mg, 0.111 mmol) and then stirred overnight. The reaction solution was added with water and extracted with ethyl acetate. Subsequently, the organic layer was washed with saturated saline, dried using anhydrous sodium sulfate, and concentrated under vacuum. The obtained residue was purified using thin-layer silica-gel chromatography (hexane:ethyl acetate=5:2), and the title compound (40.2 mg, 95%) was obtained as colorless oil.

$^1$H-NMR (CDCl$_3$) δ: 0.92 (3H, t, J=7.5 Hz), 1.51-1.62 (2H, m), 1.83-1.85 (7H, m), 2.80 (2H, t, J=7.6 Hz), 3.60 (2H, t, J=6.2 Hz), 4.07-4.08 (2H, m), 4.24 (4H, s), 6.20 (1H, s), 6.60 (1H, s), 6.80 (2H, d, J=8.8 Hz), 6.93 (1H, d, J=8.5 Hz), 7.00 (1H, s), 7.52 (1H, dd, J=1.7, 9.0 Hz).

Example 2

Preparation of 1,5,5-trimethyl-3-[4-[2-oxo-8-propyl-4-(trifluoromethyl)-2H-chromen-7-yloxy]butyl]imidazolidine-2,4-dione

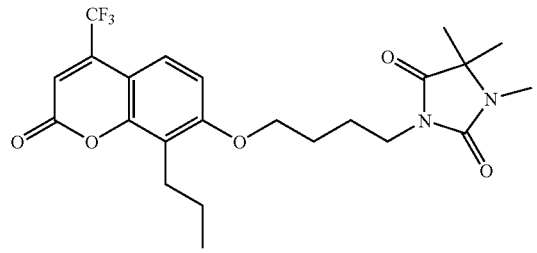

A 2-butanone (2 mL) solution of 7-hydroxy-8-propyl-4-(trifluoromethyl)-2H-chromen-2-one (30 mg, 0.11 mmol), 3-(4-bromobutyl)-1,5,5-trimethylimidazolidine-2,4-dione (30.5 mg, 0.11 mmol), and potassium carbonate (22.8 mg, 0.165 mmol) was heated and stirred overnight at 80° C. The reaction solution was added with water and extracted with ethyl acetate. Subsequently, the organic layer was washed with saturated saline, dried using anhydrous sodium sulfate, and concentrated under vacuum. The obtained residue was purified using thin-layer silica-gel chromatography (hexane:ethyl acetate=1:1), and 53.5 mg of the title compound (yield 100%) was obtained as colorless oil.

$^1$H-NMR (CDCl$_3$) δ: 0.96 (3H, t, J=7.3 Hz), 1.39 (6H, s), 1.55-1.61 (2H, m), 1.86 (4H, brs), 2.83 (2H, t, J=7.6 Hz), 2.90 (3H, s), 3.57-3.63 (2H, m), 4.10-4.13 (2H, m), 6.61 (1H, s), 6.88 (1H, d, J=9.0 Hz), 7.54 (1H, dd, J=8.9, 2.0 Hz).

By the same method as Example 1 or Example 2, the following compounds of Examples 3 to 15 were synthesized from a known compound or a compound that can be obtained by a known method.

Example 3

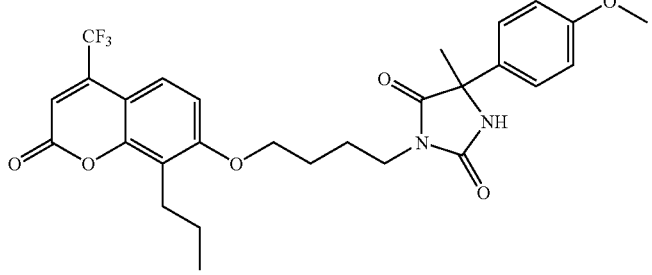

5-(4-methoxyphenyl)-5-methyl-3-(4-(2-oxo-8-propyl-4-(trifluoromethyl)-2H-chromen-7-yloxy)butyl)imidazolidin-2,4-dione $^1$H-NMR (CDCl$_3$) δ: 0.92 (3H, t, J=7.4 Hz), 1.50-1.60 (2H, m), 1.81-1.83 (7H, m), 2.79 (2H, t, J=7.6 Hz), 3.59-3.62 (2H, m), 3.78 (3H, s), 4.06-4.13 (2H, m), 6.60 (1H, s), 6.73 (1H, brs), 6.83-6.91 (3H, m), 7.41 (2H, d, J=6.8 Hz), 7.52 (1H, dd, J=8.8, 1.7 Hz)

For the compound of Example 3, its sodium salt was also synthesized as follows.

Preparation of Sodium Salt of 5-(4-methoxyphenyl)-5-methyl-3-(4-(2-oxo-8-propyl-4-(trifluoromethyl)-2H-chromen-7-yloxy)butyl)imidazolidine-2,4-dione To a tetrahydrofuran solution of 5-(4-methoxyphenyl)-5-methyl-3-(4-(2-oxo-8-propyl-4-(trifluoromethyl)-2H-chromen-7-yloxy)butyl)imidazolidine-2,4-dione (201.9 mg, 0.369 mmol), an aqueous solution of 0.98 mol/L sodium hydroxide was added in an amount of 0.75 mL and the mixture was heated at 45° C. in an oil bath for 3 hours. The reaction solution was concentrated to dryness under vacuum and the title compound (233 mg) was obtained as an yellow amorphous.

$^1$H-NMR (CD$_3$OD) δ: 0.92 (3H, t, J=7.6 Hz), 1.44-1.52 (2H, m), 1.71-1.89 (7H, m), 2.63 (2H, t, J=7.6 Hz), 3.56 (2H, t, J=6.5 Hz), 3.75 (3H, s), 3.93 (2H, t, J=6.5 Hz), 6.20 (1H, d, J=8.6 Hz), 6.79 (1H, s), 6.86-6.98 (3H, m), 7.41 (1H, J=8.6 Hz).

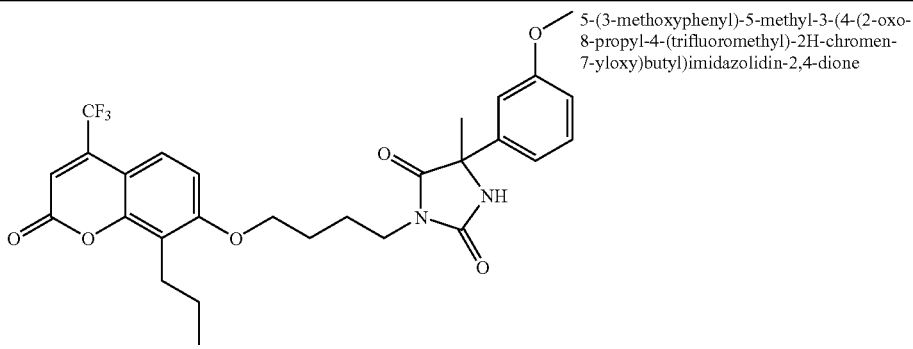

Example 4 — 5-(3-methoxyphenyl)-5-methyl-3-(4-(2-oxo-8-propyl-4-(trifluoromethyl)-2H-chromen-7-yloxy)butyl)imidazolidin-2,4-dione $^1$H-NMR (CDCl$_3$) δ: 0.92 (3H, t, J=7.3 Hz), 1.50-1.60 (2H, m), 1.82-1.84 (7H, m), 2.79 (2H, t, J=7.6 Hz), 3.59-3.61 (2H, m), 3.80 (3H, s), 4.07-4.11 (2H, m), 6.60 (1H, s), 6.83-6.89 (2H, m), 7.06-7.09 (2H, m), 7.30 (1H, t, J=8.1 Hz), 7.51 (1H, d, J=8.1 Hz).

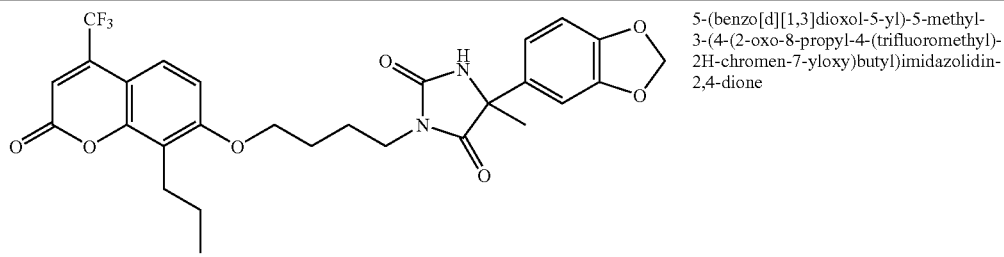

Example 5 — 5-(benzo[d][1,3]dioxol-5-yl)-5-methyl-3-(4-(2-oxo-8-propyl-4-(trifluoromethyl)-2H-chromen-7-yloxy)butyl)imidazolidin-2,4-dione $^1$H-NMR (CDCl$_3$) δ: 0.93 (3H, t, J=7.3 Hz), 1.51-1.63 (2H, m), 1.79-1.85 (7H, m), 2.80 (2H, t, J=7.6 Hz), 3.61 (2H, t, J=6.1 Hz), 4.06-4.09 (2H, m), 5.96 (2H, s), 6.34 (1H, brs), 6.61 (1H, s), 6.78 (1H, d, J=8.0 Hz), 6.85 (1H, d, J=9.0 Hz), 6.95 (1H, dd, J=8.3, 2.0 Hz), 6.99 (1H, s), 7.53 (1H, dd, J=8.6, 1.7 Hz).

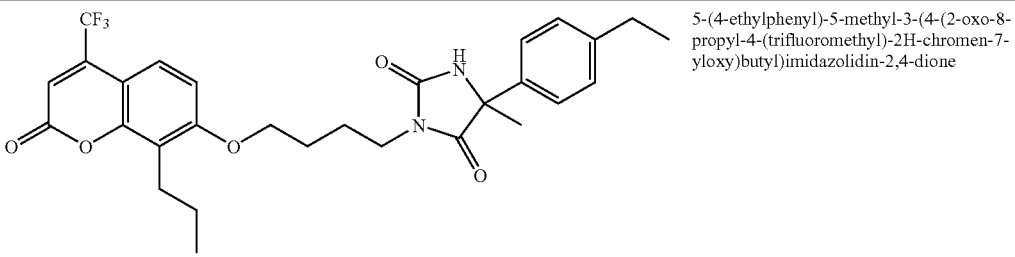

Example 6 — 5-(4-ethylphenyl)-5-methyl-3-(4-(2-oxo-8-propyl-4-(trifluoromethyl)-2H-chromen-7-yloxy)butyl)imidazolidin-2,4-dione $^1$H-NMR (CDCl$_3$) δ: 0.92 (3H, t, J=7.4 Hz), 1.21 (3H, t, J=7.6 Hz), 1.51-1.60 (2H, m), 1.82-1.85 (7H, m), 2.63 (2H, q, J=7.6 Hz), 2.80 (2H, t, J=7.6 Hz), 3.59-3.61 (2H, m), 4.06-4.09 (2H, m), 6.48 (1H, brs), 6.60 (1H, s), 6.84 (1H, d, J=9.0 Hz), 7.21 (2H, d, J=8.3 Hz), 7.41 (2H, d, J=8.3 Hz), 7.52 (1H, dd, J=8.9, 1.6 Hz).

| Example 7 | 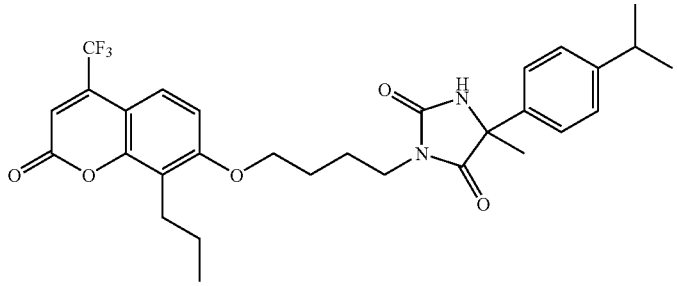 | 5-(4-isopropylphenyl)-5-methyl-3-(4-(2-oxo-8-propyl-4-(trifluoromethyl)-2H-chromen-7-yloxy)butyl)imidazolidin-2,4-dione |

$^1$H-NMR (CDCl$_3$) δ: 0.92 (3H, t, J=7.3 Hz), 1.22 (6H, d, J=6.8 Hz), 1.51-1.60 (2H, m), 1.82-1.85 (7H, m), 2.63 (2H, t, J=7.6 Hz), 2.80 (1H, sept, J=6.9 Hz), 3.59-3.61 (2H, m), 4.08-4.09 (2H, m), 6.31 (1H, brs), 6.60 (1H, s), 6.85 (1H, d, J=9.0 Hz), 7.24 (2H, d, J=8.3 Hz), 7.41 (2H, d, J=8.3 Hz), 7.52 (1H, dd, J=9.0, 1.7 Hz).

| Example 8 | 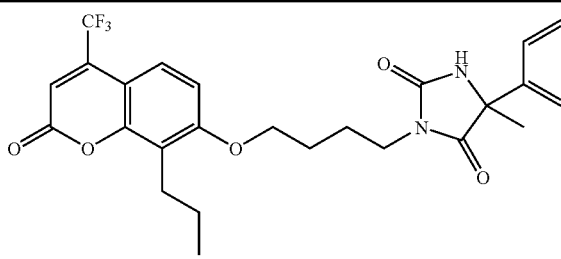 | 5-(4-ethoxyphenyl-5-methyl-3-(4-(2-oxo-8-propyl-4-(trifluoromethyl-2H-chromen-7-yloxy)butyl)imidazolidin-2,4-dione |

$^1$H-NMR (CDCl$_3$) δ: 0.92 (3H, t, J=7.3 Hz), 1.40 (3H, t, J=7.0 Hz), 1.48-1.62 (2H, m), 1.81-1.84 (7H, m), 2.63 (2H, t, J=7.6 Hz), 3.58-3.63 (2H, m), 4.00 (2H, q, J=7.0 Hz), 4.10-4.13 (2H, m), 6.46 (1H, s), 6.60 (1H, s), 6.82-6.90 (3H, m), 7.38 (2H, d, J=9.2 Hz), 7.52 (1H, dd, J=8.9, 2.0 Hz).

| Example 9 | 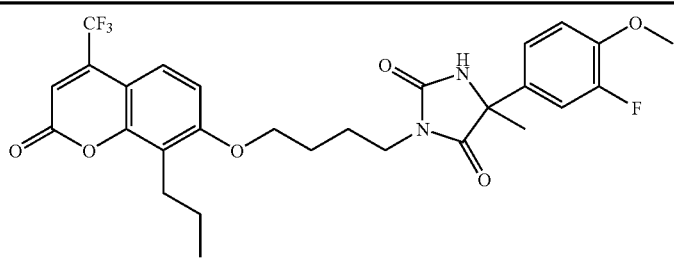 | 5-(3-fluoro-4-methoxyphenyl)-5-methyl-3-(4-(2-oxo-8-propyl-4-(trifluoromethyl)-2H-chromene-7-yloxy)butyl)imidazolidin-2,4-dione |

$^1$H-NMR (CDCl$_3$) δ: 0.92 (3H, t, J=7.4 Hz), 1.48-1.62 (2H, m), 1.81-1.84 (7H, m), 2.80 (2H, t, J=7.6 Hz), 3.61 (2H, s), 3.88 (3H, s), 4.08-4.13 (2H, m), 6.47 (1H, s), 6.60 (1H, s), 6.84 (1H, d, J=9.2 Hz), 6.95 (1H, m), 7.20-7.23 (2H, m), 7.52 (1H, dd, J=8.9, 1.6 Hz).

| Example 10 | 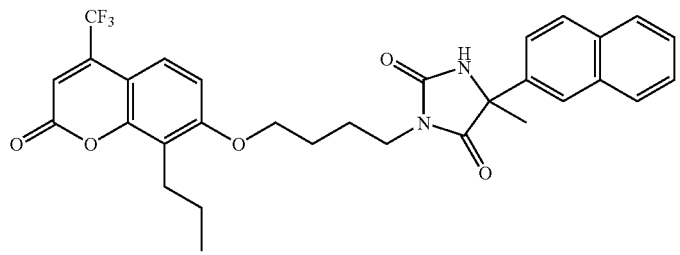 | 5-methyl-5-(naphthalen-2-yl)-3-(4-(2-oxo-8-propyl-4-(trifluoromethyl)-2H-chromen-7-yloxy)butyl)imidazolidin-2,4-dione |

$^1$H-NMR (CDCl$_3$) δ: 0.89 (3H, t, J=7.3 Hz), 1.47-1.57 (2H, m), 1.82-1.93 (7H, m), 2.76 (2H, t, J=7.6 Hz), 3.62-3.68 (2H, m), 4.02-4.05 (2H, m), 6.46 (1H, s), 6.59 (1H, s), 6.78 (1H, d, J=9.0 Hz), 7.47-7.52 (3H, m), 7.60-7.62 (1H, m), 7.80-7.87 (3H, m), 7.95 (1H, s).

| Example 11 | 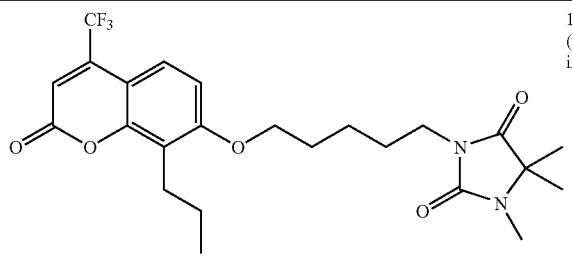 | 1,5,5-trimethyl-3-(5-(2-oxo-8-propyl-4-(trifluoromethyl)-2H-chromen-7-yloxy)pentyl)-imidazolidin-2,4-dione |

$^1$H-NMR (CDCl$_3$) δ: 0.96 (3H, t, J=7.4 Hz), 1.37 (6H, s), 1.41-1.63 (4H, m), 1.67-1.82 (2H, m), 1.86-1.92 (2H, m), 2.80-2.89 (5H, m), 3.55 (2H, t, J=7.3 Hz), 4.09 (2H, t, J=8.06 Hz), 6.60 (1H, s), 6.87 (1H, d, J=9.3 Hz), 7.54 (1H, dd, J=10.4, 2.0 Hz).

| Example 12 | 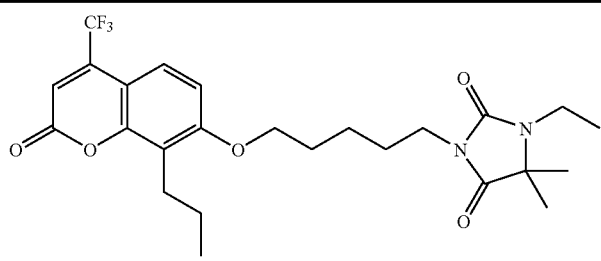 | 1-ethyl-5,5-dimethyl-3-(5-(2-oxo-8-propyl-4-(trifluoromethyl)-2H-chromen-7-yloxy)-pentyl)imidazolidin-2,4-dione |

$^1$H-NMR (CDCl$_3$) δ: 0.96 (3H, t, J=7.3 Hz), 1.25 (3H, t, J=7.3 Hz), 1.39 (6H, s), 1.46-1.94 (6H, m), 2.82 (2H, t, J=7.6 Hz), 3.34 (2H, q, J=7.3 Hz), 3.51-3.56 (2H, m), 4.05-4.09 (2H, m), 6.60 (1H, s), 6.86 (1H, d, J=8.9 Hz), 7.53 (1H, d, J=8.9 Hz).

| Example 13 | 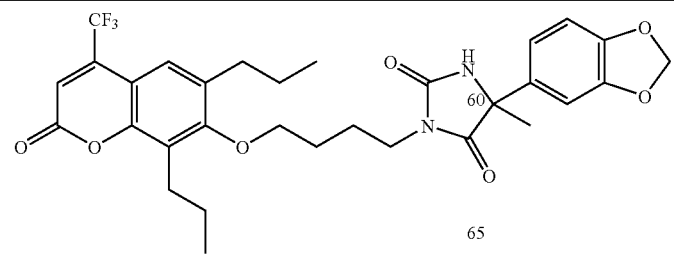 | 5-(benzo[d][1,3]dioxol-5-yl)-5-methyl-3-(4-(2-oxo-6,8-dipropyl-4-(trifluoromethyl)-2H-chromen-7-yloxy)butyl)imidazolidin-2,4-dione |

¹H-NMR (CDCl₃) δ: 0.96-0.99 (6H, m), 1.57-1.68 (4H, m), 1.81-1.89 (7H, m), 2.61 (2H, t, J=7.8 Hz), 2.76 (2H, t, J=7.8 Hz), 3.63 (2H, t, J=6.7 Hz), 3.82 (2H, t, J=5.9 Hz), 5.96 (2H, s), 6.51 (1H, brs), 6.68 (1H, s), 6.78 (1H, d, J=8.1 Hz), 6.95-6.98 (2H, m), 7.37 (1H, s).

| Example 14 | 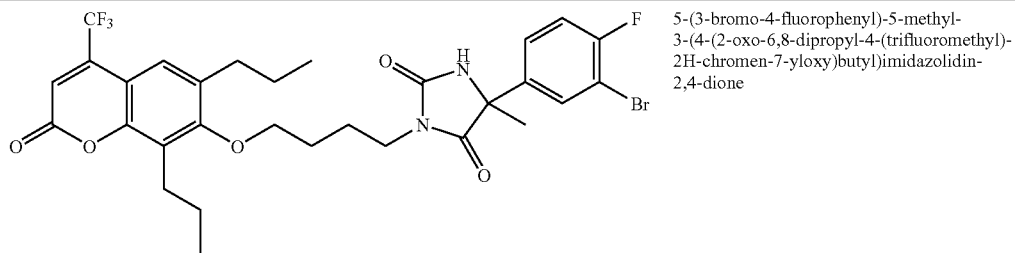 | 5-(3-bromo-4-fluorophenyl)-5-methyl-3-(4-(2-oxo-6,8-dipropyl-4-(trifluoromethyl)-2H-chromen-7-yloxy)butyl)imidazolidin-2,4-dione |
|---|---|---|

¹H-NMR (CDCl₃) δ: 0.93-0.98 (6H, m), 1.57-1.66 (4H, m), 1.83-1.90 (7H, m), 2.60 (2H, t, J=7.8 Hz), 2.76 (2H, t, J=7.8 Hz), 3.64 (2H, t, J=7.0 Hz), 3.82 (2H, t, J=5.9 Hz), 6.55 (1H, s), 6.69 (1H, s), 7.13 (1H, t, J=8.3 Hz), 7.37 (1H, s), 7.46-7.50 (1H, m), 7.72-7.75 (1H, m).

| Example 15 | 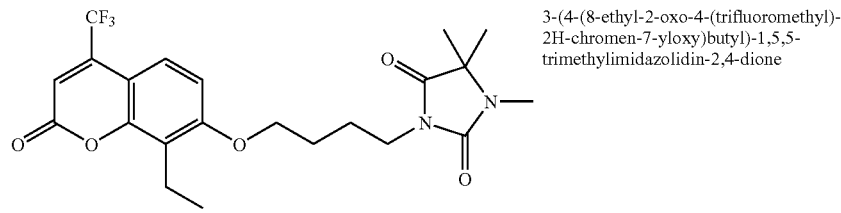 | 3-(4-(8-ethyl-2-oxo-4-(trifluoromethyl)-2H-chromen-7-yloxy)butyl)-1,5,5-trimethylimidazolidin-2,4-dione |
|---|---|---|

¹H-NMR (CDCl₃) δ: 1.15 (3H, t, J=6.3 Hz), 1.38 (6H, s), 1.87 (4H, brs), 2.84-2.92 (5H, m), 3.61 (2H, brs), 4.13 (2H, brs), 6.61 (1H, s), 6.89 (1H, d, J=9.0 Hz), 7.54 (1H, d, J=9.0 Hz).

By the same method as Example 1 or Example 2, the following compounds listed on Table 1-1 to Table 1-35 were synthesized from a known compound or a compound that can be obtained by a known method. The NMR data of a part of compounds are shown on Table 1-36 to Table 1-38.

TABLE 1-1

| Example 16 | 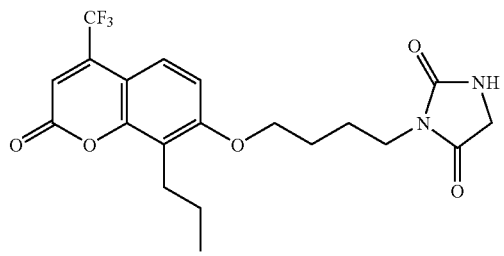 | 3-(4-(2-oxo-8-propyl-4-(trifluoromethyl)-2H-chromen-7-yloxy)butyl)imidazolidin-2,4-dione |
|---|---|---|

TABLE 1-1-continued

| Example 17 | 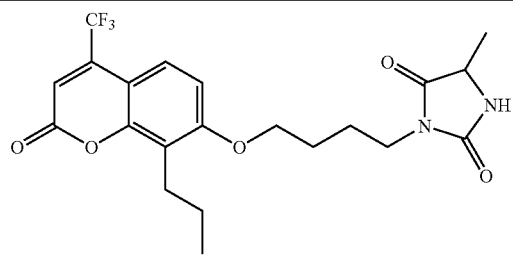 | 5-methyl-3-(4-(2-oxo-8-propyl-4-(trifluoromethyl)-2H-chromen-7-yloxy)butyl)imidazolidin-2,4-dione |
| Example 18 | 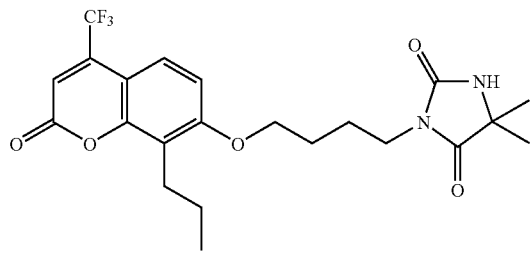 | 5,5-dimethyl-3-(4-(2-oxo-8-propyl-4-(trifluoromethyl)-2H-chromen-7-yloxy)butyl)imidazolidin-2,4-dione |
| Example 19 | 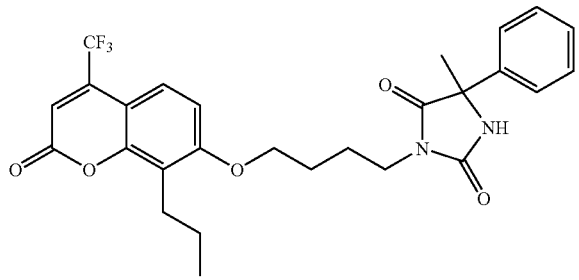 | 5-methyl-3-(4-(2-oxo-8-propyl-4-(trifluoromethyl)-2H-chromen-7-yloxy)butyl)-5-phenylimidazolidin-2,4-dione |
| Example 20 | 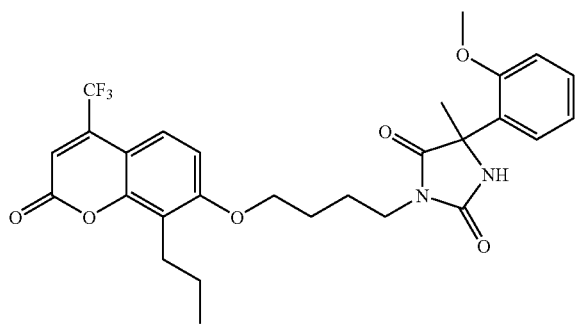 | 5-(2-methoxyphenyl)-5-methyl-3-(4-(2-oxo-8-propyl-4-(trifluoromethyl)-2H-chromen-7-yloxy)butyl)imidazolidin-2,4-dione |
| Example 21 | 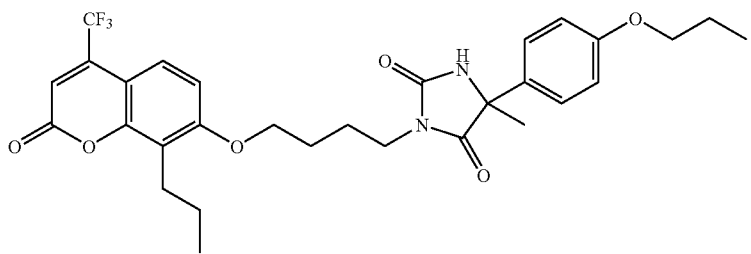 | 5-methyl-3-(4-(2-oxo-8-propyl-4-(trifluoromethyl)-2H-chromen-7-yloxy)butyl)-5-(4-propoxyphenyl)-imidazolidin-2,4-dione |
| Example 22 | 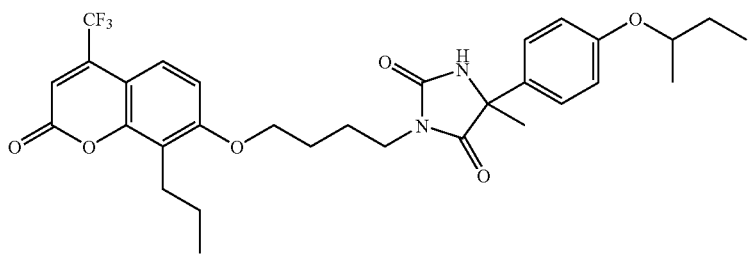 | 5-(4-isopropoxyphenyl)-5-methyl-3-(4-(2-oxo-8-propyl-4-(trifluoromethyl)-2H-chromen-7-yloxy)butyl)imidazolidin-2,4-dione |

TABLE 1-1-continued

| Example 23 | 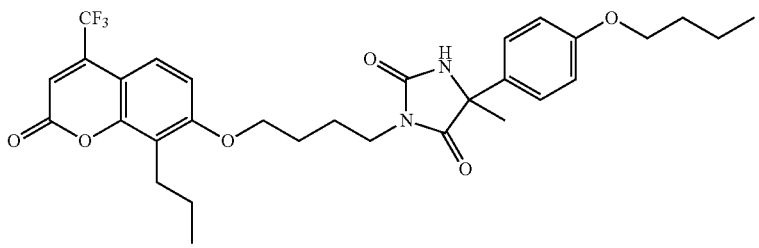 | 5-(4-butoxyphenyl)-5-methyl-3-(4-(2-oxo-8-propyl-4-(trifluoro-methyl)-2H-chromen-7-yloxy)-butyl)imidazolidin-2,4-dione |

TABLE 1-2

| Example 24 | 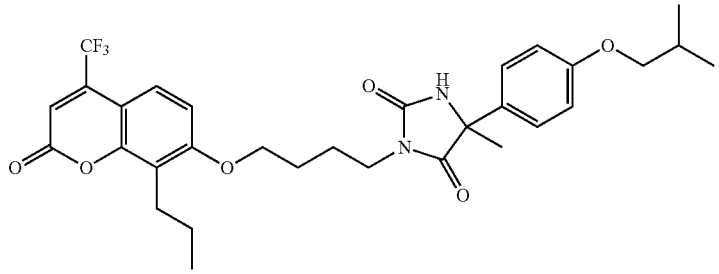 | 5-(4-isobutoxyphenyl)-5-methyl-3-(4-(2-oxo-8-propyl-4-(trifluoromethyl)-2H-chromen-7-yloxy)butyl)-imidazolidin-2,4-dione |
| Example 25 | 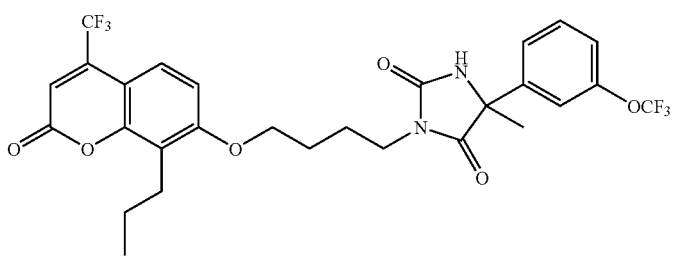 | 5-methyl-3-(4-(2-oxo-8-propyl-4-(trifluoromethyl)-2H-chromen-7-yloxy)-butyl)-5-(3-(trifluoromethoxy)phenyl)-imidazolidin-2,4-dione |
| Example 26 | 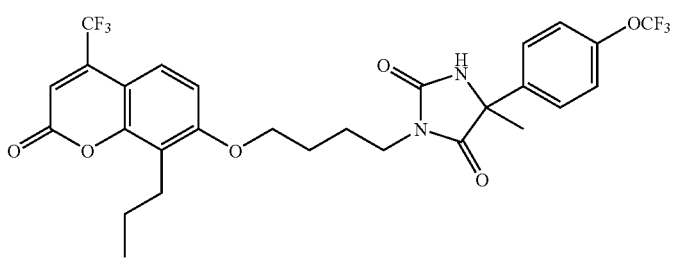 | 5-methyl-3-(4-(2-oxo-8-propyl-4-(trifluoromethyl)-2H-chromen-7-yloxy)-butyl)-5-(4-(trifluoromethoxy)phenyl)-imidazolidin-2,4-dione |
| Example 27 | 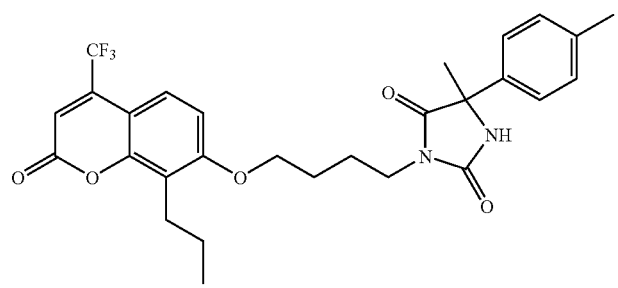 | 5-methyl-3-(4-(2-oxo-8-propyl-4-(trifluoromethyl)-2H-chromen-7-yloxy)-butyl)-5-p-tolylimidazolidin-2,4-dione |

TABLE 1-2-continued

| Example 28 | 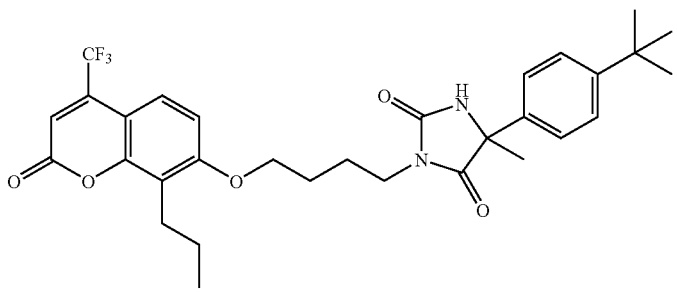 | 5-(4-tert-butylphenyl)-5-methyl-3-(4-(2-oxo-8-propyl-4-(trifluoromethyl)-2H-chromen-7-yloxy)butyl)imidazolidin-2,4-dione |
| --- | --- | --- |
| Example 29 | 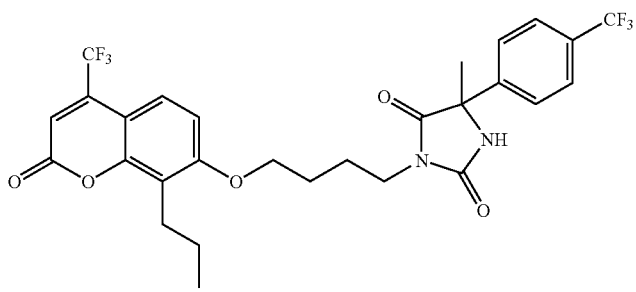 | 5-methyl-3-(4-(2-oxo-8-propyl-4-(trifluoromethyl)-2H-chromen-7-yloxy)-butyl)-5-(4-(trifluoromethyl)phenyl)-imidazolidin-2,4-dione |
| Example 30 | 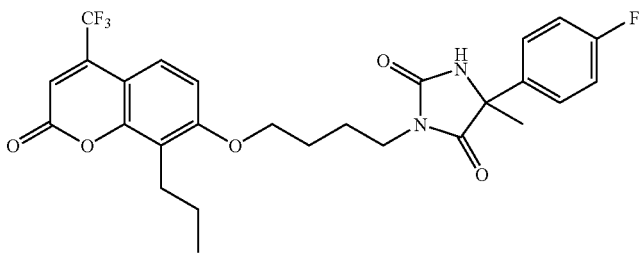 | 5-(4-fluorophenyl-5-methyl-3-(4-(2-oxo-8-propyl-4-(trifluoromethyl)-2H-chromen-7-yloxy)butyl)imidazolidin-2,4-dione |
| Example 31 | 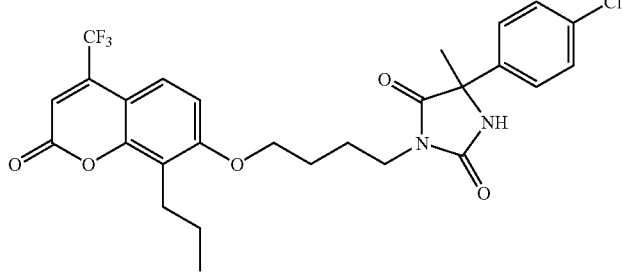 | 5-(4-chlorophenyl)-5-methyl-3-(4-(2-oxo-8-propyl-4-(trifluoromethyl)-2H-chromen-7-yloxy)butyl)imidazolidin-2,4-dione |

TABLE 1-3

| Example 32 | 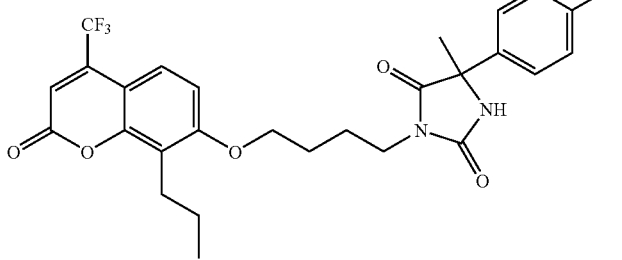 | 5-(4-bromophenyl)-5-methyl-3-(4-(2-oxo-8-propyl-4-(trifluoromethyl)-2H-chromen-7-yloxy)butyl)imidazolidin-2,4-dione |
| --- | --- | --- |

TABLE 1-3-continued

| Example 33 | 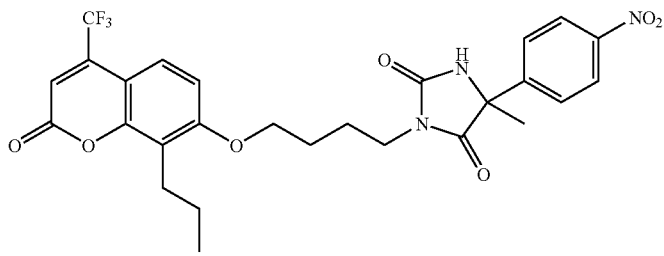 | 5-methyl-5-(4-nitrophenyl)-3-(4-(2-oxo-8-propyl-4-(trifluoromethyl)-2H-chromen-7-yloxy)butyl)imidazolidin-2,4-dione |
| Example 34 | 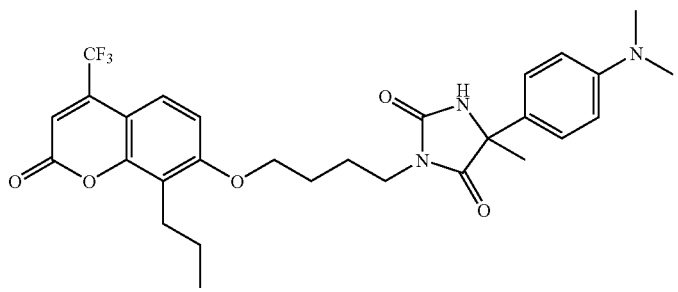 | 5-(4-(dimethylamino)phenyl)-5-methyl-3-(4-(2-oxo-8-propyl-4-(trifluoromethyl)-2H-chromen-7-yloxy)butyl)-imidazolidin-2,4-dione |
| Example 35 | 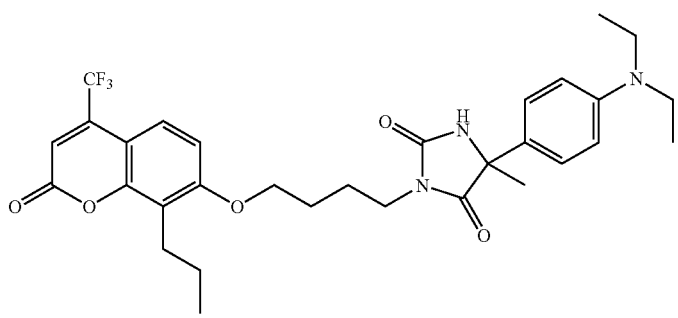 | 5-(4-(diethylamino)phenyl)-5-methyl-3-(4-(2-oxo-8-propyl-4-(trifluoromethyl)-2H-chromen-7-yloxy)butyl)-imidazolidin-2,4-dione |
| Example 36 | 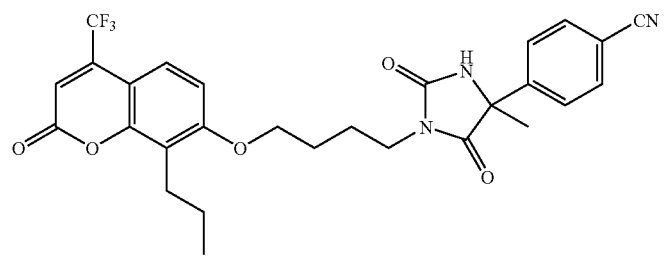 | 4-(4-methyl-2,5-dioxo-1-(4-(2-oxo-8-propyl-4-(trifluoromethyl)-2H-chromen-7-yloxy)butyl)imidazolidin-4-yl)-benzonitrile |
| Example 37 | 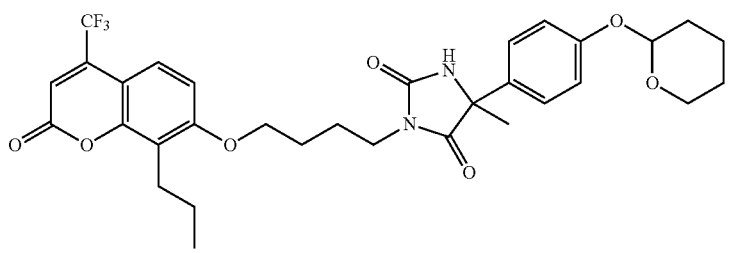 | 5-methyl-3-(4-(2-oxo-8-propyl-4-(trifluoromethyl)-2H-chromen-7-yloxy)butyl)-5-(4-(tetrahydro-2H-pyran-2-yloxy)phenyl)imidazolidin-2,4-dione |
| Example 38 | 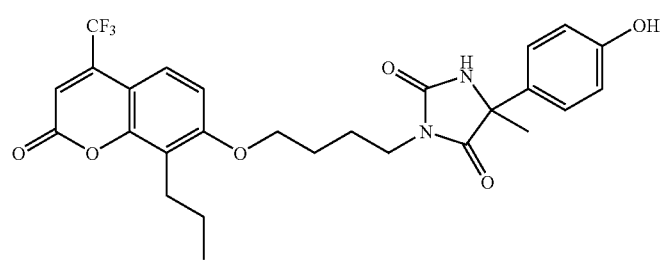 | 5-(4-hydroxyphenyl)-5-methyl-3-(4-(2-oxo-8-propyl-4-(trifluoromethyl)-2H-chromen-7-yloxy)butyl)imidazolidin-2,4-dione |

TABLE 1-3-continued

| Example 39 | 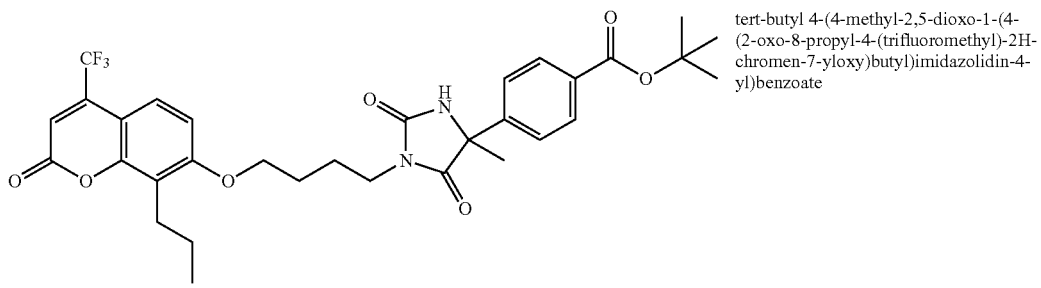 | tert-butyl 4-(4-methyl-2,5-dioxo-1-(4-(2-oxo-8-propyl-4-(trifluoromethyl)-2H-chromen-7-yloxy)butyl)imidazolidin-4-yl)benzoate |

TABLE 1-4

| Example 40 | 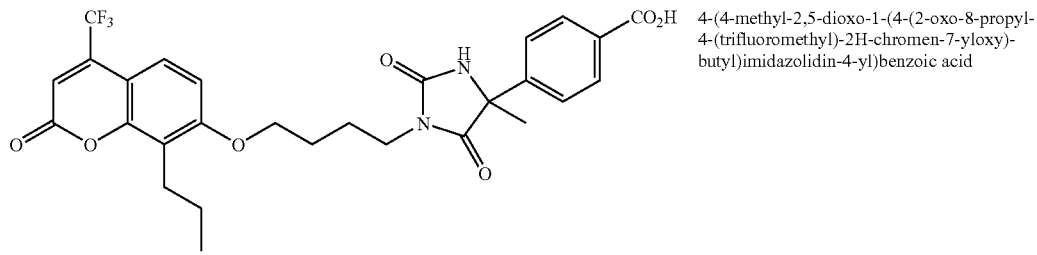 | 4-(4-methyl-2,5-dioxo-1-(4-(2-oxo-8-propyl-4-(trifluoromethyl)-2H-chromen-7-yloxy)-butyl)imidazolidin-4-yl)benzoic acid |
| Example 41 | 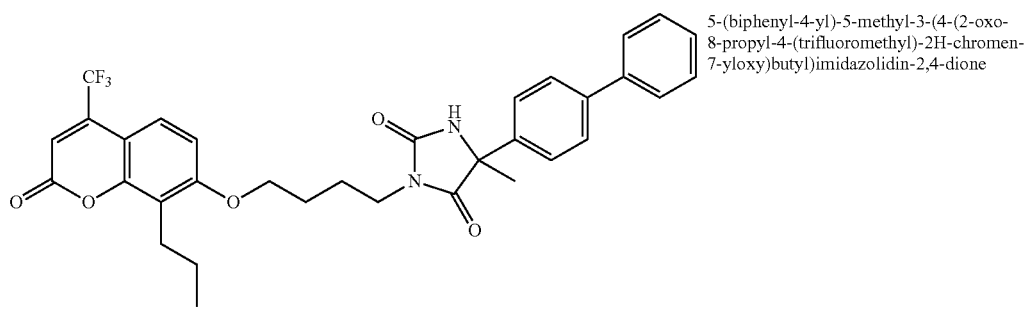 | 5-(biphenyl-4-yl)-5-methyl-3-(4-(2-oxo-8-propyl-4-(trifluoromethyl)-2H-chromen-7-yloxy)butyl)imidazolidin-2,4-dione |
| Example 42 | 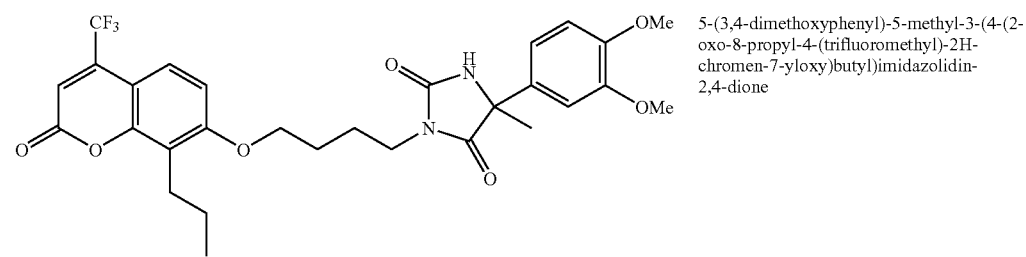 | 5-(3,4-dimethoxyphenyl)-5-methyl-3-(4-(2-oxo-8-propyl-4-(trifluoromethyl)-2H-chromen-7-yloxy)butyl)imidazolidin-2,4-dione |
| Example 43 | 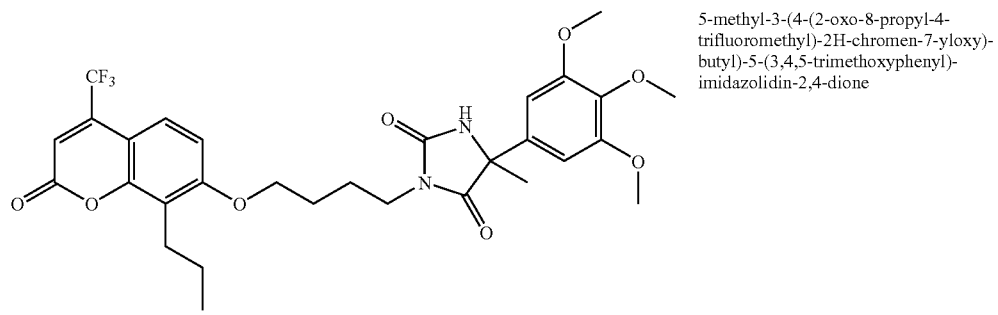 | 5-methyl-3-(4-(2-oxo-8-propyl-4-trifluoromethyl)-2H-chromen-7-yloxy)-butyl)-5-(3,4,5-trimethoxyphenyl)-imidazolidin-2,4-dione |

TABLE 1-4-continued

| Example 44 | 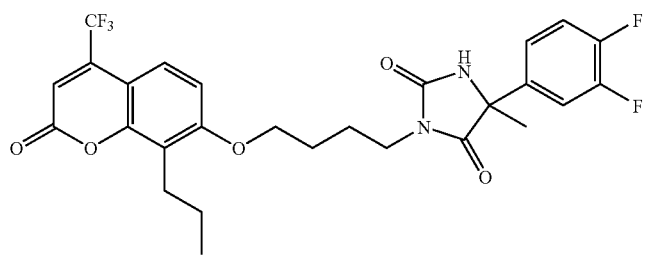 | 5-(3,4-difluorophenyl)-5-methyl-3-(4-(2-oxo-8-propyl-4-(trifluoromethyl)-2H-chromen-7-yloxy)butyl)imidazolidin-2,4-dione |
| Example 45 | 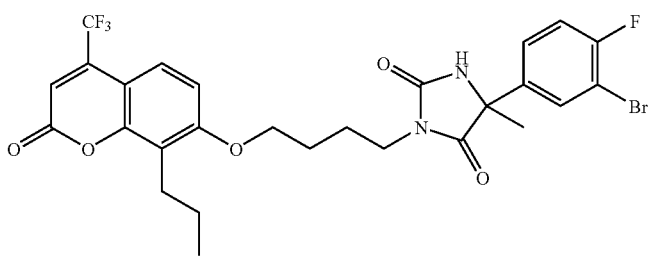 | 5-(3-bromo-4-fluorophenyl)-5-methyl-3-(4-(2-oxo-8-propyl-4-(trifluoromethyl)-2H-chromen-7-yloxy)butyl)imidazolidin-2,4-dione |
| Example 46 | 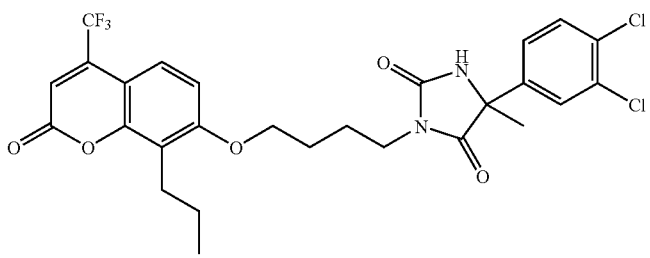 | 5-(3,4-dichlorophenyl-5-methyl-3-(4-(2-oxo-8-propyl-4-(trifluoromethyl)-2H-chromen-7-yloxy)butyl)imidazolidin-2,4-dione |
| Example 47 | 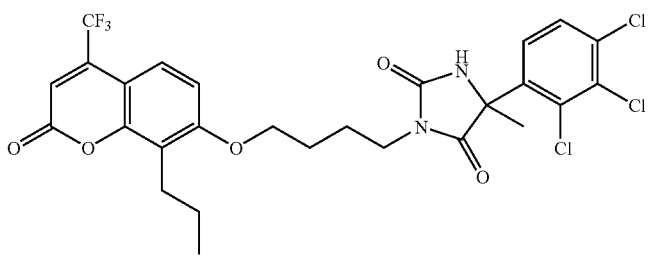 | 5-methyl-3-(4-(2-oxo-8-propyl-4-(trifluoromethyl)-2H-chromen-7-yloxy)butyl)-5-(2,3,4-trichlorophenyl)imidazolidin-2,4-dione |

TABLE 1-5

| Example 48 | 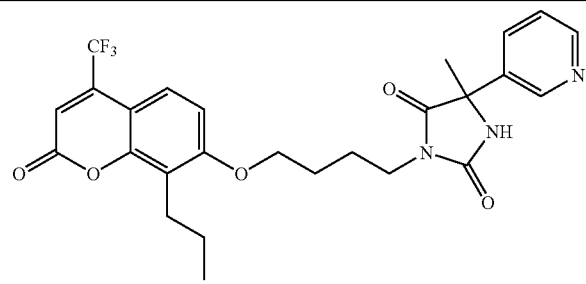 | 5-methyl-3-(4-(2-oxo-8-propyl-4-(trifluoromethyl)-2H-chromen-7-yloxy)butyl)-5-(pyridin-3-yl)imidazolidin-2,4-dione |

TABLE 1-5-continued

| Example 49 | 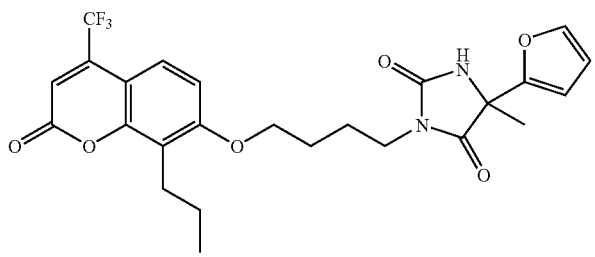 | 5-(furan-2-yl)-5-methyl-3-(4-(2-oxo-8-propyl-4-(trifluoromethyl)-2H-chromen-7-yloxy)-butyl)imidazolidin-2,4-dione |
| --- | --- | --- |
| Example 50 | 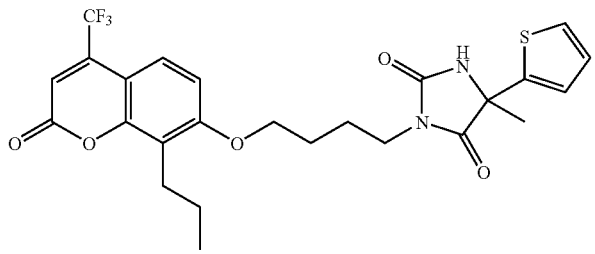 | 5-methyl-3-(4-(2-oxo-8-propyl-4-(trifluoromethyl)-2H-chromen-7-yloxy)butyl)-5-(thiophen-2-yl)imidazolidin-2,4-dione |
| Example 51 | 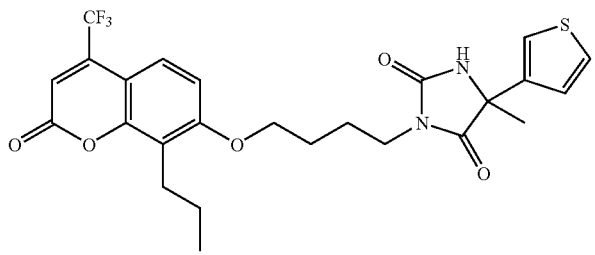 | 5-methyl-3-(4-(2-oxo-8-propyl-4-(trifluoromethyl)-2H-chromen-7-yloxy)butyl)-5-(thiophen-3-yl)imidazolidin-2,4-dione |
| Example 52 | 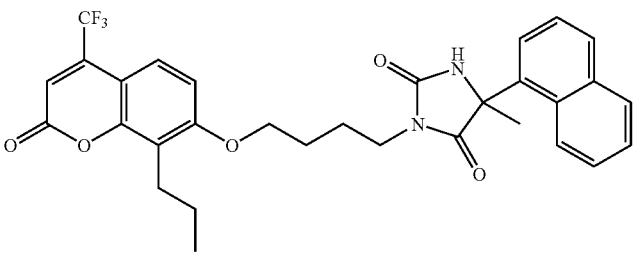 | 5-methyl-5-(naphthalen-1-yl)-3-(4-(2-oxo-8-propyl-4-(trifluoromethyl)-2H-chromen-7-yloxy)butyl)imidazolidin-2,4-dione |
| Example 53 | 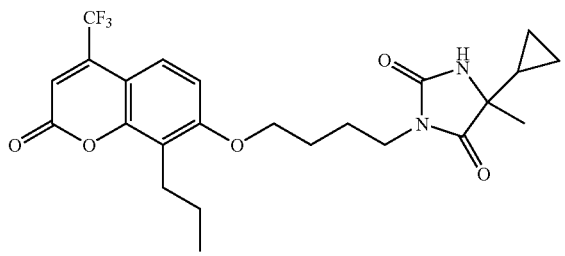 | 5-cyclopropyl-5-methyl-3-(4-(2-oxo-8-propyl-4-(trifluoromethyl)-2H-chromen-7-yloxy)butyl)imidazolidin-2,4-dione |
| Example 54 | 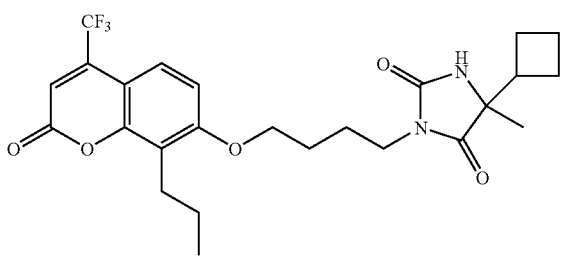 | 5-cyclobutyl-5-methyl-3-(4-(2-oxo-8-propyl-4-(trifluoromethyl)-2H-chromen-7-yloxy)-butyl)imidazolidin-2,4-dione |

TABLE 1-5-continued

| Example 55 | 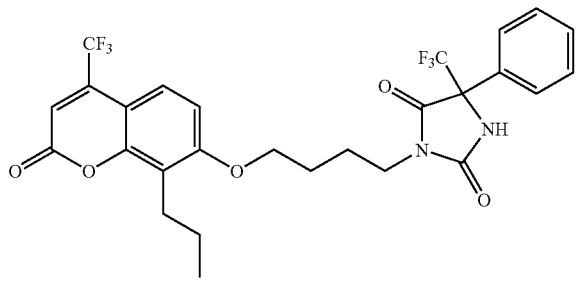 | 3-(4-(2-oxo-8-propyl-4-(trifluoromethyl)-2H-chromen-7-yloxy)butyl)-5-phenyl-5-(trifluoromethyl)imidazolidin-2,4-dione |

TABLE 1-6

| Example 56 | 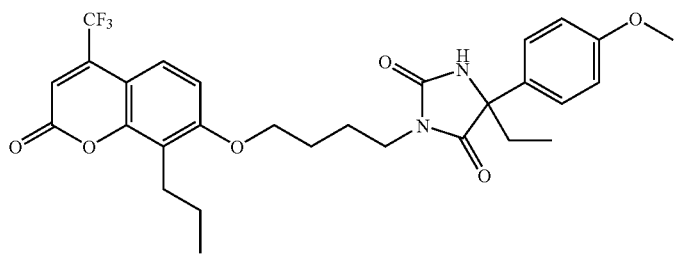 | 5-ethyl-5-(4-methoxyphenyl)-3-(4-(2-oxo-8-propyl-4-(trifluoromethyl)-2H-chromen-7-yloxy)butyl)imidazolidin-2,4-dione |
| Example 57 | 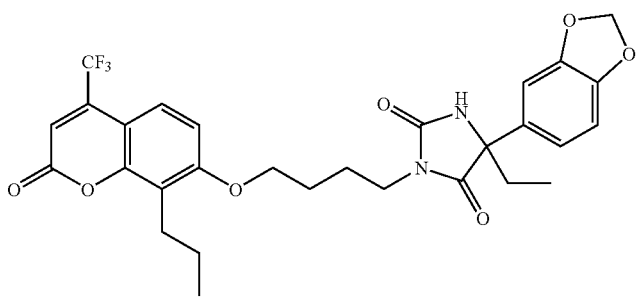 | 5-(benzo[d][1,3]dioxol-5-yl)-5-ethyl-3-(4-(2-oxo-8-propyl-4-(trifluoromethyl)-2H-chromen-7-yloxy)butyl)imidazolidin-2,4-dione |
| Example 58 | 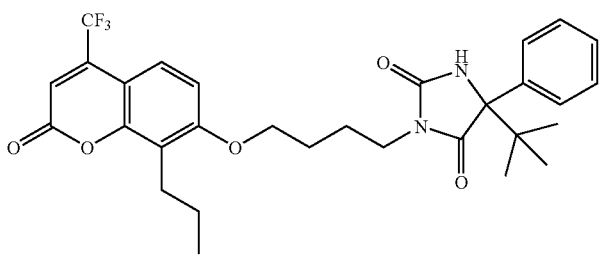 | 5-tert-butyl-3-(4-(2-oxo-8-propyl-4-(trifluoromethyl)-2H-chromen-7-yloxy)butyl)-5-phenylimidazolidin-2,4-dione |
| Example 59 | 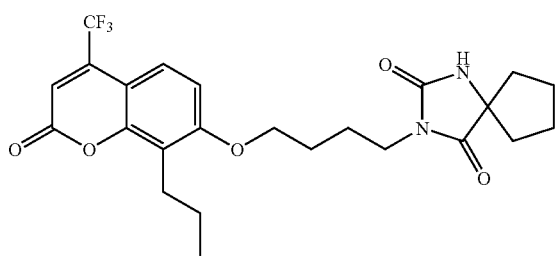 | 3-(4-(2-oxo-8-propyl-4-(trifluoromethyl)-2H-chromen-7-yloxy)butyl)-1,3-diazaspiro-[4.4]nonane-2,4-dione |

TABLE 1-6-continued

Example 60 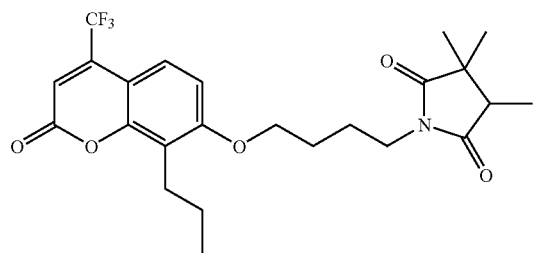 3,3,4-trimethyl-1-(4-(2-oxo-8-propyl-4-trifluoromethyl)-2H-chromen-7-yloxy)butyl)-pyrrolidine-2,5-dione Example 61 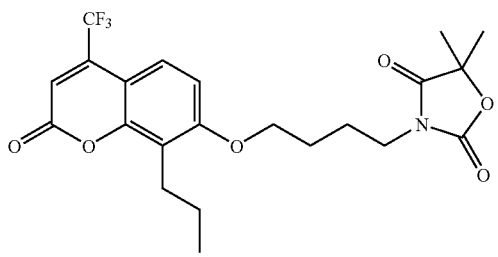 5,5-dimethyl-3-(4-(2-oxo-8-propyl-4-(trifluoromethyl)-2H-chromen-7-yloxy)butyl)-oxazolidin-2,4-dione Example 62 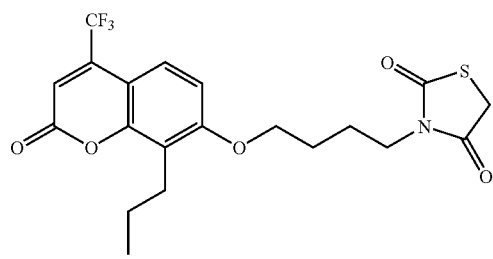 3-(4-(2-oxo-8-propyl-4-(trifluoromethyl)-2H-chromen-7-yloxy)butyl)thiazolidin-2,4-dione Example 63 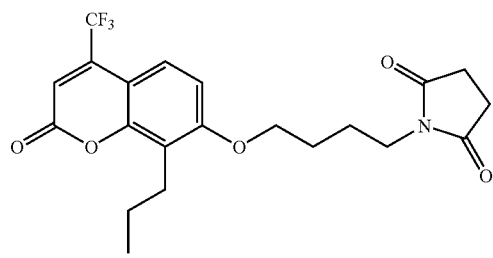 1-(4-(2-oxo-8-propyl-4-(trifluoromethyl)-2H-chromen-7-yloxy)butyl)pyrrolidine-2,5-dione Example 64 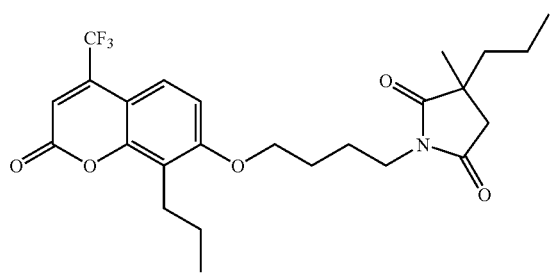 3-methyl-1-(4-(2-oxo-8-propyl-4-(trifluoromethyl)-2H-chromen-7-yloxy)butyl)-3-propylpyrrolidine-2,5-dione

TABLE 1-7

| | | |
|---|---|---|
| Example 65 | 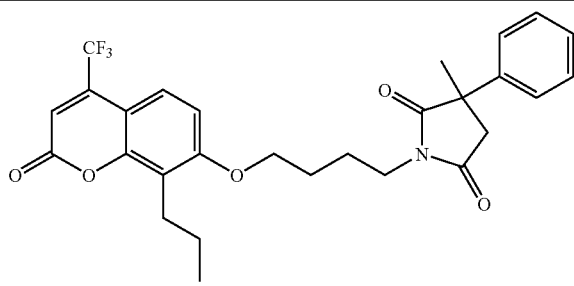 | 3-methyl-1-(4-(2-oxo-8-propyl-4-(trifluoromethyl)-2H-chromen-7-yloxy)butyl)-3-phenylpyrrolidine-2,5-dione |
| Example 66 | 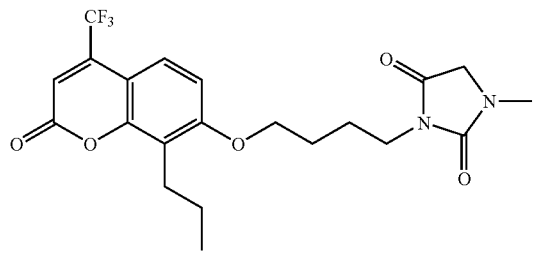 | 1-methyl-3-(4-(2-oxo-8-propyl-4-(trifluoromethyl)-2H-chromen-7-yloxy)butyl)-imidazolidin-2,4-dione |
| Example 67 | 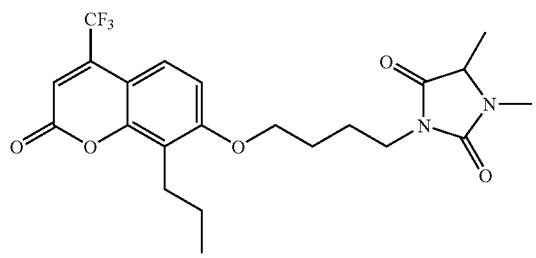 | 1,5-dimethyl-3-(4-(2-oxo-8-propyl-4-(trifluoromethyl)-2H-chromen-7-yloxy)butyl)-imidazolidin-2,4-dione |
| Example 68 | 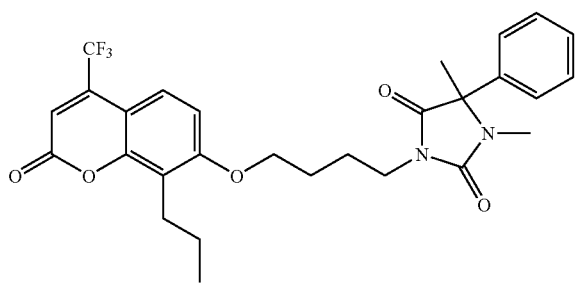 | 1,5-dimethyl-3-(4-(2-oxo-8-propyl-4-(trifluoromethyl)-2H-chromen-7-yloxy)butyl)-5-phenylimidazolidin-2,4-dione |
| Example 69 | 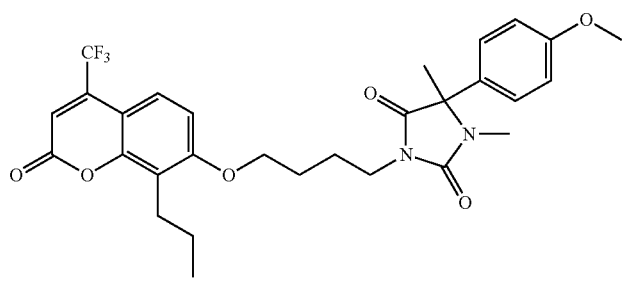 | 5-(4-methoxyphenyl)-1,5-dimethyl-3-(4-(2-oxo-8-propyl-4-(trifluoromethyl)-2H-chromen-7-yloxy)butyl)imidazolidin-2,4-dione |
| Example 70 | 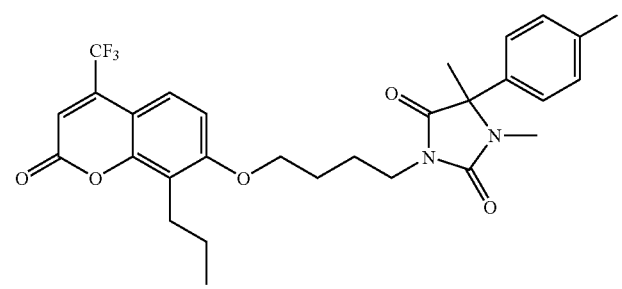 | 1,5-dimethyl-3-(4-(2-oxo-8-propyl-4-(trifluoromethyl)-2H-chromen-7-yloxy)butyl)-5-p-tolylimidazolidin-2,4-dione |

TABLE 1-7-continued

| Example 71 | 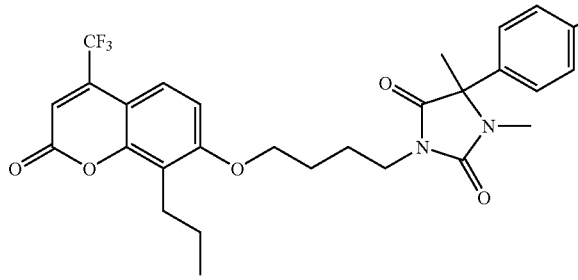 | Cl | 5-(4-chlorophenyl)-1,5-dimethyl-3-(4-(2-oxo-8-propyl-4-(trifluoromethyl)-2H-chromen-7-yloxy)butyl)imidazolidin-2,4-dione |
| --- | --- | --- | --- |
| Example 72 | 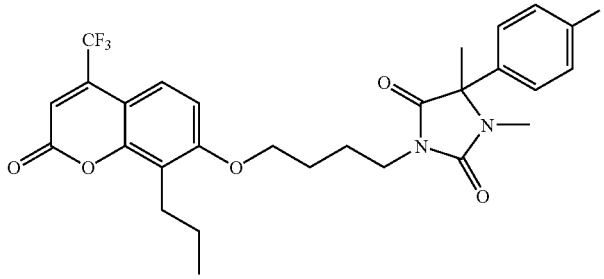 | Br | 5-(4-bromophenyl)-1,5-dimethyl-3-(4-(2-oxo-8-propyl-4-(trifluoromethyl)-2H-chromen-7-yloxy)butyl)imidazolidin-2,4-dione |

TABLE 1-8

| Example 73 | 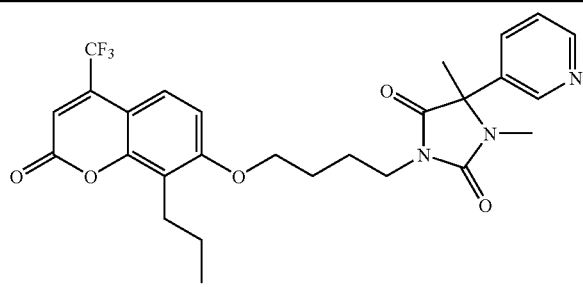 | 1,5-dimethyl-3-(4-(2-oxo-8-propyl-4-(trifluoromethyl)-2H-chromen-7-yloxy)butyl)-5-(pyridin-3-yl)imidazolidin-2,4-dione |
| --- | --- | --- |
| Example 74 | 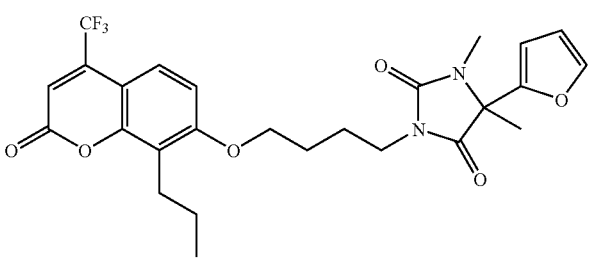 | 5-(furan-2-yl)-1,5-dimethyl-3-(4-(2-oxo-8-propyl-4-(trifluoromethyl)-2H-chromen-7-yloxy)butyl)imidazolidin-2,4-dione |
| Example 75 | 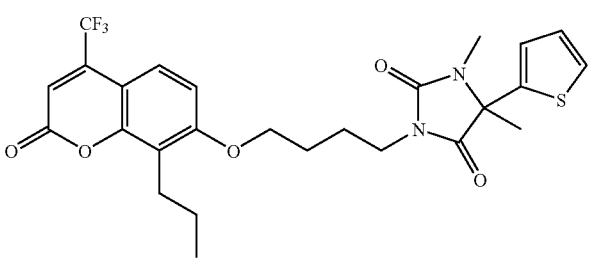 | 1,5-dimethyl-3-(4-(2-oxo-8-propyl-4-(trifluoromethyl)-2H-chromen-7-yloxy)butyl)-5-(thiophen-2-yl)imidazolidin-2,4-dione |

TABLE 1-8-continued

| Example 76 | 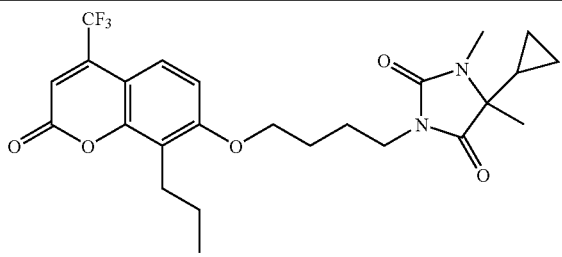 | 5-cyclopropyl-1,5-dimethyl-3-(4-(2-oxo-8-propyl-4-(trifluoromethyl)-2H-chromen-7-yloxy)-butyl)imidazolidin-2,4-dione |
| Example 77 | 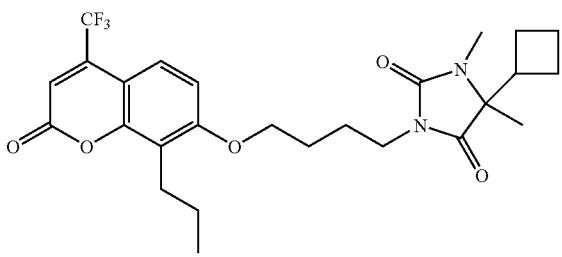 | 5-cyclobutyl-1,5-dimethyl-3-(4-(2-oxo-8-propyl-4-(trifluoromethyl)-2H-chromen-7-yloxy)-butyl)imidazolidin-2,4-dione |
| Example 78 | 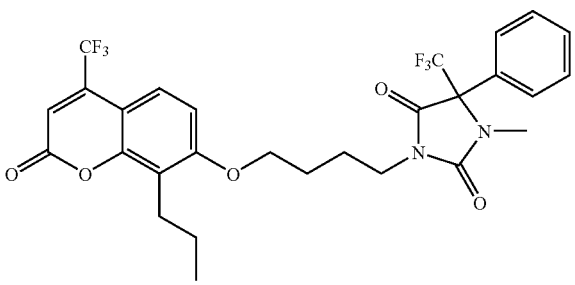 | 1-methyl-3-(4-(2-oxo-8-propyl-4-(trifluoromethyl)-2H-chromen-7-yloxy)butyl)-5-phenyl-5-(trifluoromethyl)imidazolidin-2,4-dione |
| Example 79 | 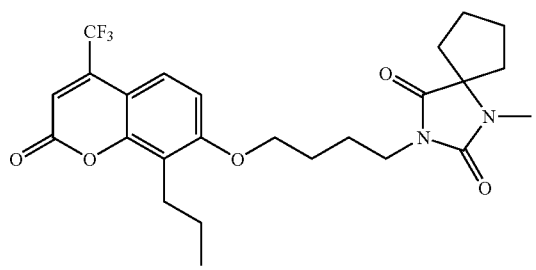 | 1-methyl-3-(4-(2-oxo-8-propyl-4-(trifluoromethyl)-2H-chromen-7-yloxy)butyl)-1,3-diazaspiro[4.4]nonane-2,4-dione |
| Example 80 | 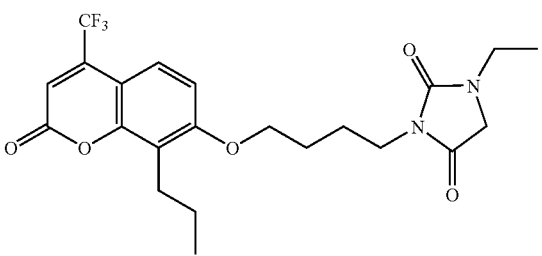 | 1-ethyl-3-(4-(2-oxo-8-propyl-4-(trifluoromethyl)-2H-chromen-7-yloxy)butyl)- |

TABLE 1-9

Example 81 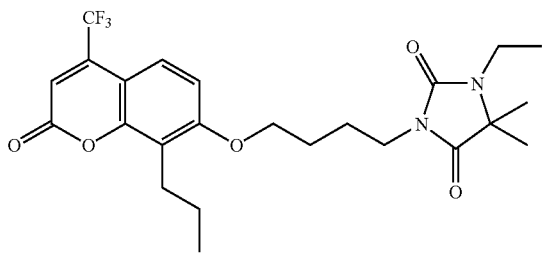 1-ethyl-5,5-dimethyl-3-(4-(2-oxo-8-propyl-4-(trifluoromethyl)-2H-chromen-7-yloxy)butyl)imidazolidin-2,4-dione Example 82 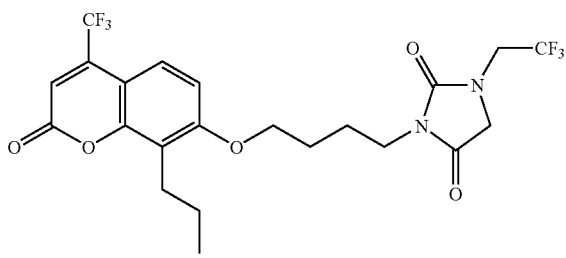 3-(4-(2-oxo-8-propyl-4-(trifluoromethyl)-2H-chromen-7-yloxy)butyl)-1-(2,2,2-trifluoroethyl)imidazolidin-2,4-dione Example 83 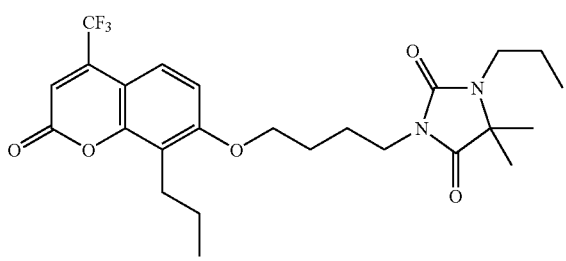 5,5-dimethyl-3-(4-(2-oxo-8-propyl-4-(trifluoromethyl)-2H-chromen-7-yloxy)butyl)-1-propylimidazolidin-2,4-dione Example 84 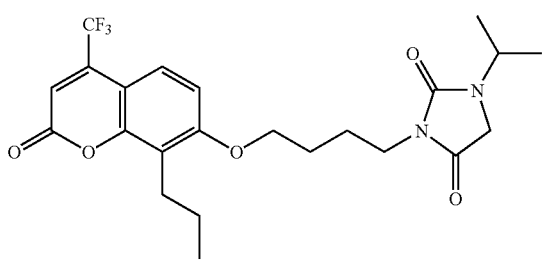 1-isopropyl-3-(4-(2-oxo-8-propyl-4-(trifluoromethyl)-2H-chromen-7-yloxy)butyl)imidazolidin-2,4-dione Example 85 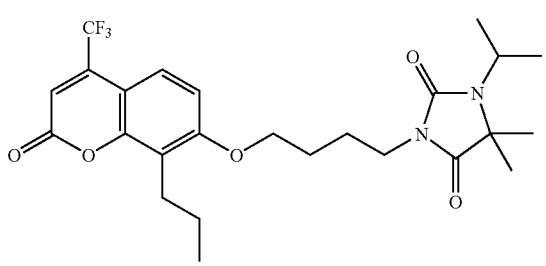 1-isopropyl-5,5-dimethyl-3-(4-(2-oxo-8-propyl-4-(trifluoromethyl)-2H-chromen-7-yloxy)butyl)imidazolidin-2,4-dione Example 86 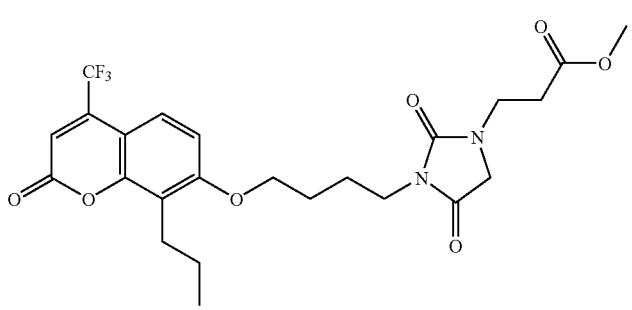 methyl 3-(2,4-dioxo-3-(4-(2-oxo-8-propyl-4-(trifluoromethyl)-2H-chromen-7-yloxy)butyl)imidazolidin-1-yl) propanoate TABLE 1-9-continued Example 87 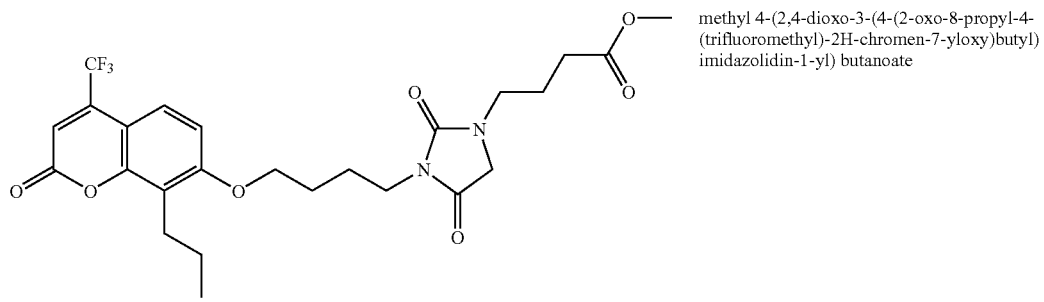 methyl 4-(2,4-dioxo-3-(4-(2-oxo-8-propyl-4-(trifluoromethyl)-2H-chromen-7-yloxy)butyl) imidazolidin-1-yl) butanoate Example 88 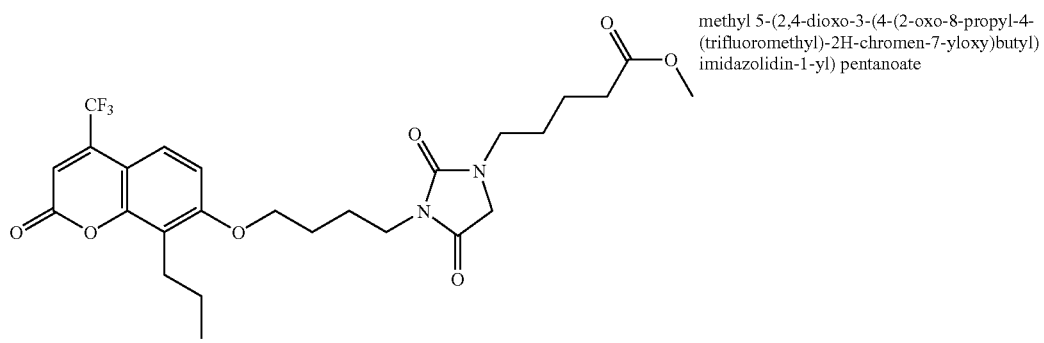 methyl 5-(2,4-dioxo-3-(4-(2-oxo-8-propyl-4-(trifluoromethyl)-2H-chromen-7-yloxy)butyl) imidazolidin-1-yl) pentanoate

TABLE 1-10

Example 89 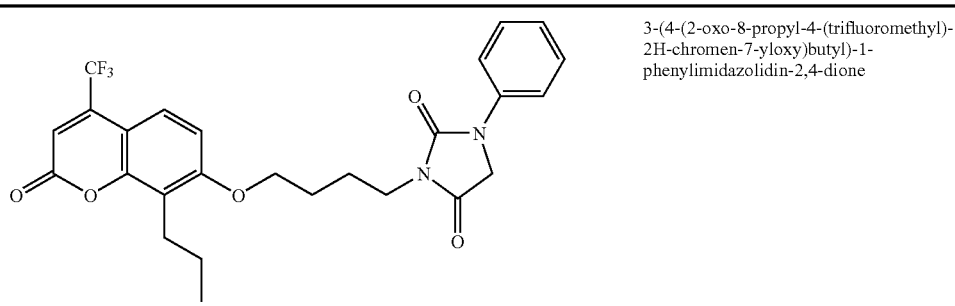 3-(4-(2-oxo-8-propyl-4-(trifluoromethyl)-2H-chromen-7-yloxy)butyl)-1-phenylimidazolidin-2,4-dione Example 90 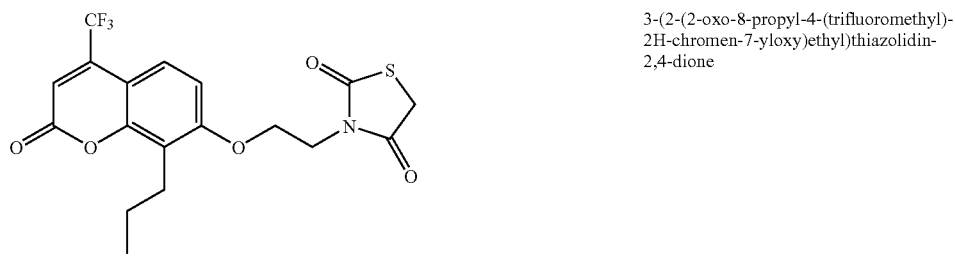 3-(2-(2-oxo-8-propyl-4-(trifluoromethyl)-2H-chromen-7-yloxy)ethyl)thiazolidin-2,4-dione Example 91 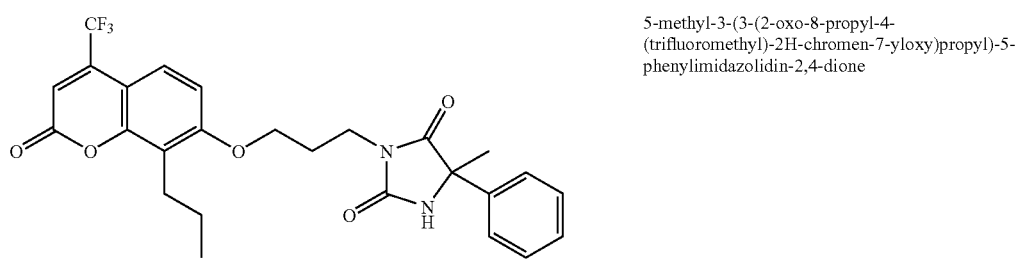 5-methyl-3-(3-(2-oxo-8-propyl-4-(trifluoromethyl)-2H-chromen-7-yloxy)propyl)-5-phenylimidazolidin-2,4-dione TABLE 1-10-continued

| | | |
|---|---|---|
| Example 92 | 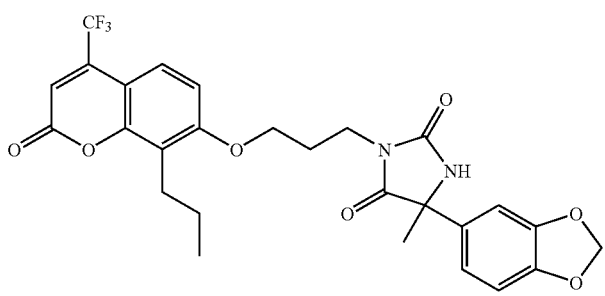 | 5-(benzo[d][1,3]dioxol-5-yl)-5-methyl-3-(3-(2-oxo-8-propyl-4-(trifluoromethyl)-2H-chromen-7-yloxy)propyl) imidazolidin-2,4-dione |
| Example 93 | 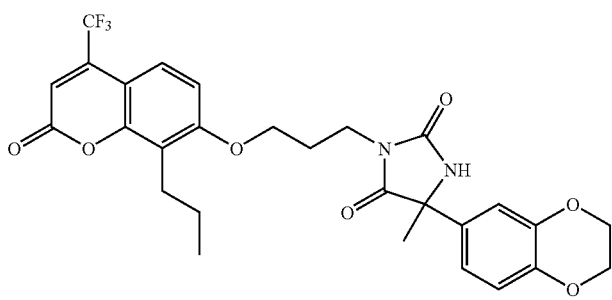 | 5-(2,3-dihydrobenzo[b][1,4]dioxin-6-yl)-5-methyl-3-(3-(2-oxo-8-propyl-4-(trifluoromethyl)-2H-chromen-7-yloxy)propyl) imidazolidin-2,4-dione |
| Example 94 | 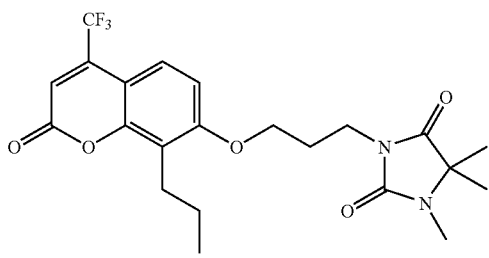 | 1,5,5-trimethyl-3-(3-(2-oxo-8-propyl-4-(trifluoromethyl)-2H-chromen-7-yloxy)propyl) imidazolidin-2,4-dione |
| Example 95 | 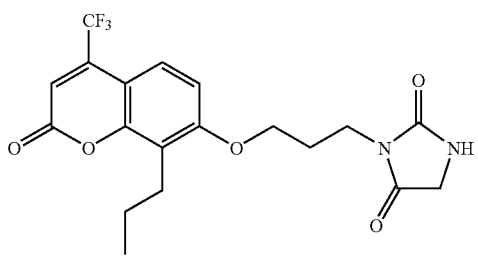 | 3-(3-(2-oxo-8-propyl-4-(trifluoromethyl)-2H-chromen-7-yloxy)propyl) imidazolidin-2,4-dione |
| Example 96 | 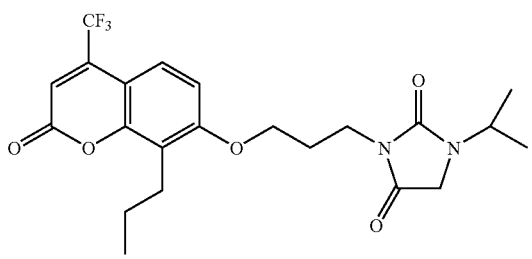 | 1-isopropyl-3-(3-(2-oxo-8-propyl-4-(trifluoromethyl)-2H-chromen-7-yloxy)propyl) imidazolidin-2,4-dione |

TABLE 1-11

Example 97 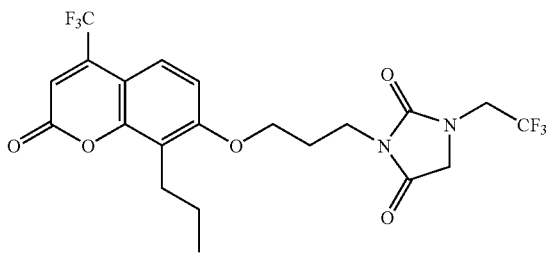 3-(3-(2-oxo-8-propyl-4-(trifluoromethyl)-2H-chromen-7-yloxy)propyl)-1-(2,2,2-trifluoroethyl)imidazolidin-2,4-dione Example 98 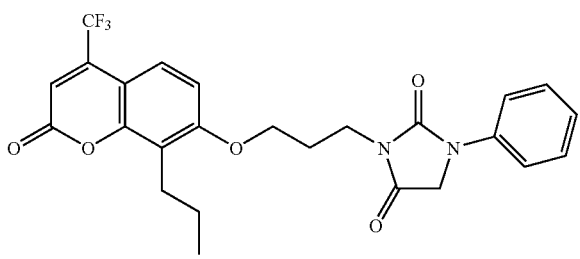 3-(3-(2-oxo-8-propyl-4-(trifluoromethyl)-2H-chromen-7-yloxy)propyl)-1-phenylimidazolidin-2,4-dione Example 99 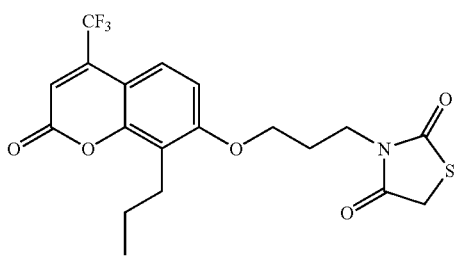 3-(3-(2-oxo-8-propyl-4-(trifluoromethyl)-2H-chromen-7-yloxy)propyl) thiazolidin-2,4-dione Example 100 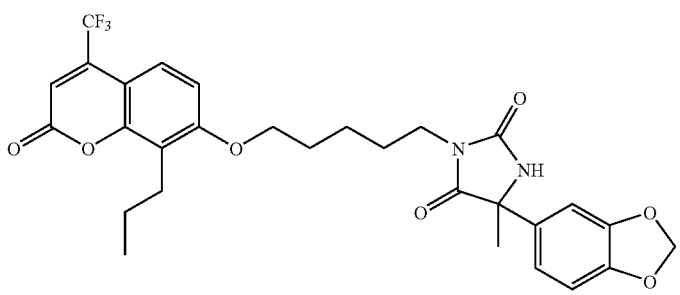 5-(benzo[d](1,3-dioxol-5-yl)-5-methyl-3-(5-(2-oxo-8-propyl-4-(trifluoromethyl)-2H-chromen-7-yloxy)pentyl) imidazolidin-2,4-dione Example 101 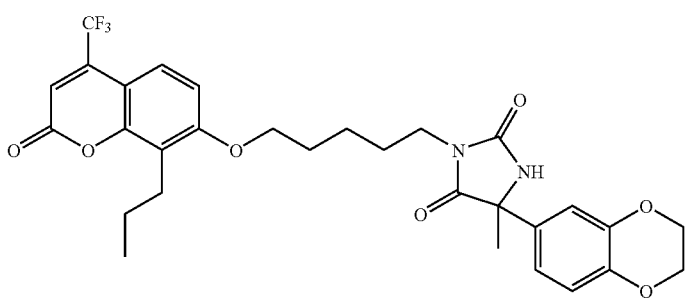 5-(2,3-dihydrobenzo[b][1,4]dioxin-6-yl)-5-methyl-3-(5-(2-oxo-8-propyl-4-(trifluoromethyl)-2H-chromen-7-yloxy)pentyl) imidazolidin-2,4-dione TABLE 1-11-continued

| | | |
|---|---|---|
| Example 102 | 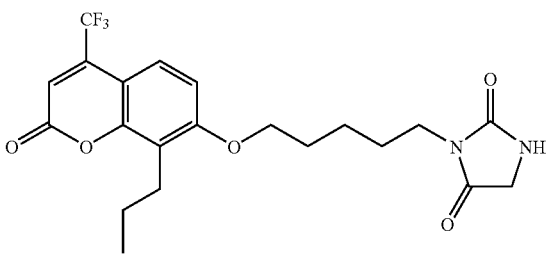 | 3-(5-(2-oxo-8-propyl-4-(trifluoromethyl)-2H-chromen-7-yloxy)pentyl)imidazolidin-2,4-dione |
| Example 103 | 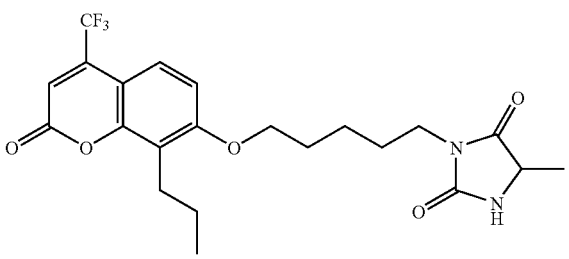 | 5-methyl-3-(5-(2-oxo-8-propyl-4-(trifluoromethyl)-2H-chromen-7-yloxy)pentyl)imidazolidin-2,4-dione |
| Example 104 | 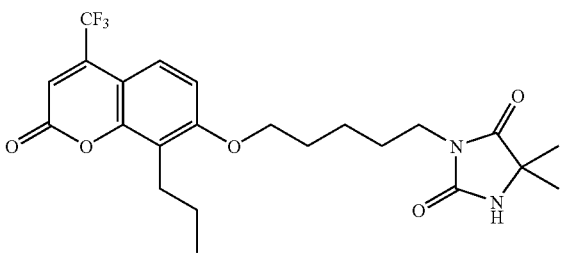 | 5,5-dimethyl-3-(5-(2-oxo-8-propyl-4-(trifluoromethyl)-2H-chromenthyloxy)pentyl)imidazolidin-2,4-dione |

TABLE 1-12

| | | |
|---|---|---|
| Example 105 | 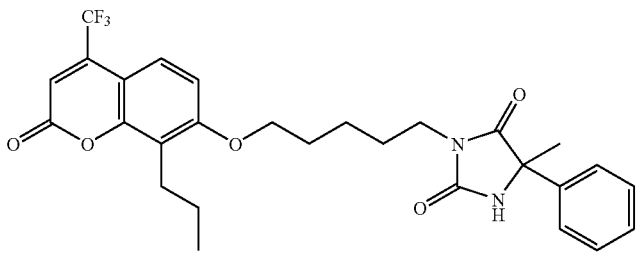 | 5-methyl-3-(5-(2-oxo-8-propyl-4-(trifluoromethyl)-2H-chromen-7-yloxy)pentyl)-5-phenylimidazolidin-2,4-dione |
| Example 106 | 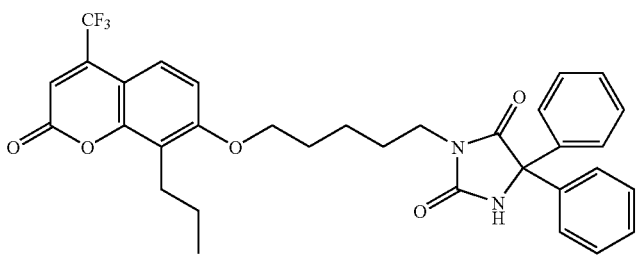 | 3-(5-(2-oxo-8-propyl-4-(trifluoromethyl)-2H-chromen-7-yloxy)pentyl)-5,5-diphenylimidazolidin-2,4-dione |

| | | |
|---|---|---|
| Example 107 | 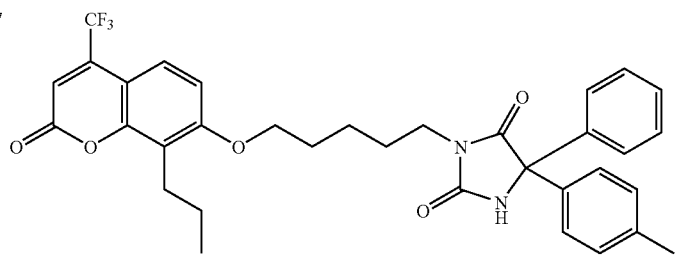 | 3-(5-(2-oxo-8-propyl-4-(trifluoromethyl)-2H-chromen-7-yloxy)pentyl)-5-phenyl-5-p-tolylimidazolidin-2,4-dione |
| Example 108 | 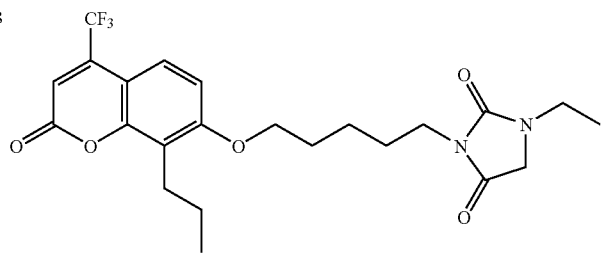 | 1-ethyl-3-(5-(2-oxo-8-propyl-4-(trifluoromethyl)-2H-chromen-7-yloxy)pentyl)imidazolidin-2,4-dione |
| Example 109 | 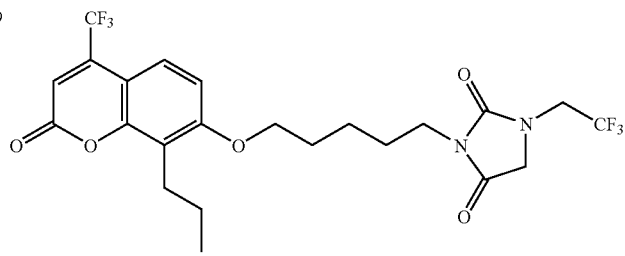 | 3-(5-(2-oxo-8-propyl-4-(trifluoromethyl)-2H-chromen-7-yloxy)pentyl)-1-(2,2,2-trifluoroethyl)imidazolidin-2,4-dione |
| Example 110 | 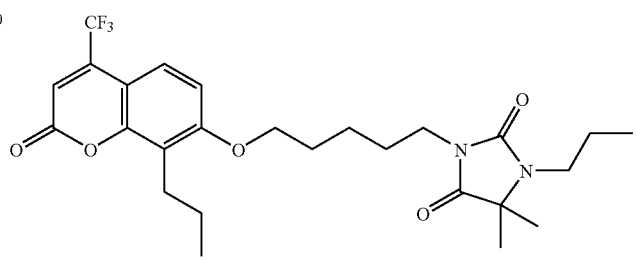 | 5,5-dimethyl-3-(5-(2-oxo-8-propyl-4-(trifluoromethyl)-2H-chromen-7-yloxy)pentyl)-1-propylimidazolidin-2,4-dione |
| Example 111 | 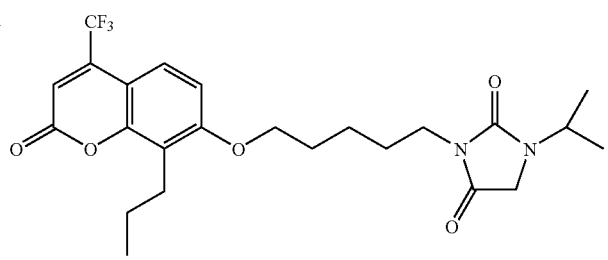 | 1-isopropyl-3-(5-(2-oxo-8-propyl-4-(trifluoromethyl)-2H-chromen-7-yloxy)pentyl)imidazolidin-2,4-dione |
| Example 112 | 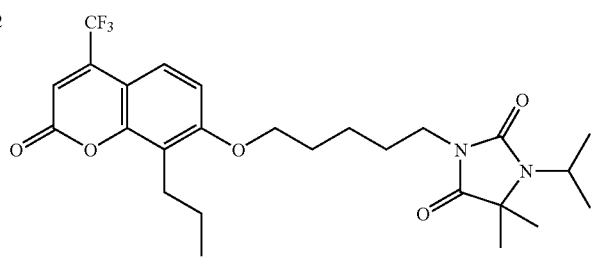 | 1-isopropyl-5,5-dimethyl-3-5-(2-oxo-8-propyl-4-(trifluoromethyl)-2H-chromen-7-yloxy)pentyl)imidazolidin-2,4-dione |

TABLE 1-13

| Example 113 | 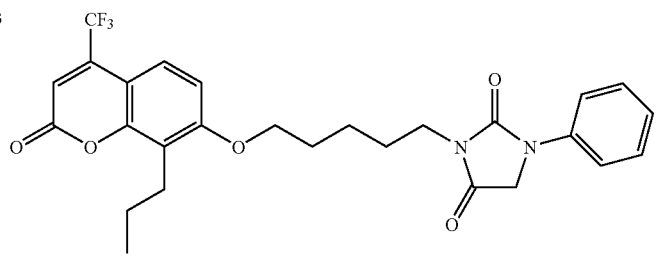 | 3-(5-(2-oxo-8-propyl-4-(trifluoromethyl)-2H-chromen-7-yloxy)pentyl)-1-phenylimidazolidin-2,4-dione |
| Example 114 | 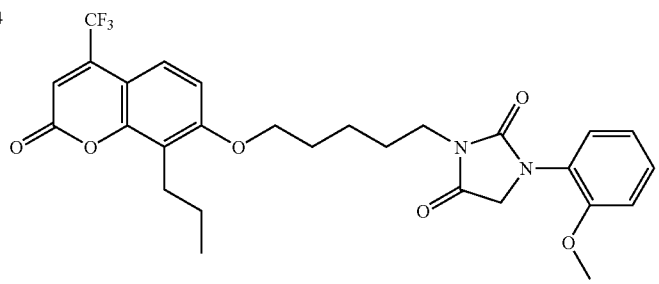 | 1-(2-methoxyphenyl)-3-(5-(2-oxo-8-propyl-4-(trifluoromethyl)-2H-chromen-7-yloxy)pentyl)imidazolidin-2,4-dione |
| Example 115 | 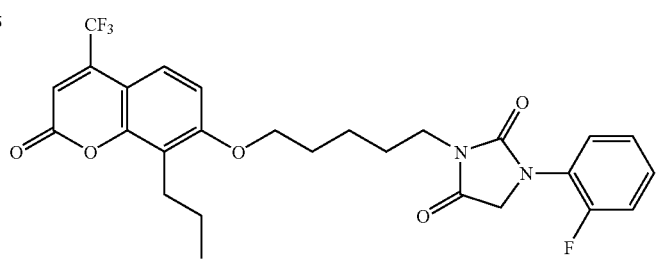 | 1-(2-fluorophenyl)-3-(5-(2-oxo-8-propyl-4-(trifluoromethyl)-2H-chromen-7-yloxy)pentyl)imidazolidin-2,4-dione |
| Example 116 | 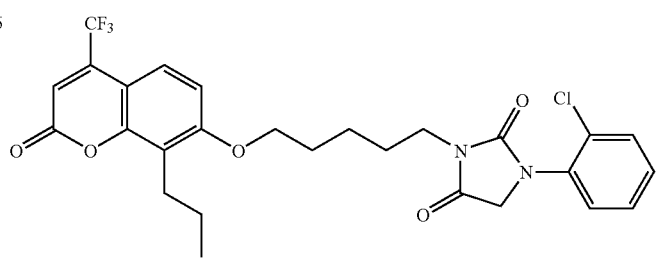 | 1-(2-chlorophenyl)-3-(5-(2-oxo-8-propyl-4-(trifluoromethyl)-2H-chromen-7-yloxy)pentyl)imidazolidin-2,4-dione |
| Example 117 | 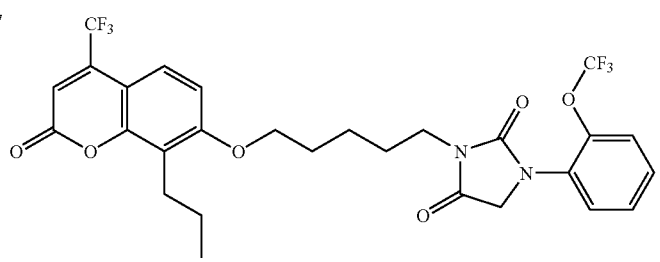 | 3-(5-(2-oxo-8-propyl-4-(trifluoromethyl)-2H-chromen-7-yloxy)pentyl)-1-(2-(trifluoromethoxy)phenyl)imidazolidin-2,4-dione |
| Example 118 | 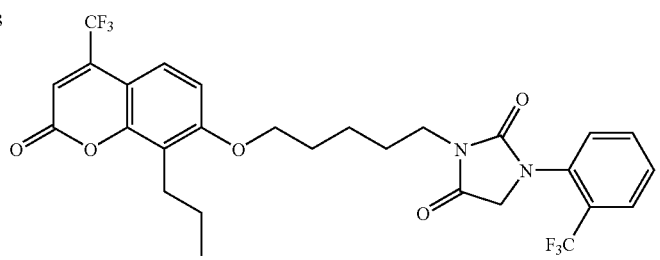 | 3-(5-(2-oxo-8-propyl-4-(trifluoromethyl)-2H-chromen-7-yloxy)pentyl)-1-(2-(trifluoromethyl)phenyl)imidazolidin-2,4-dione |

TABLE 1-13-continued

| Example 119 | 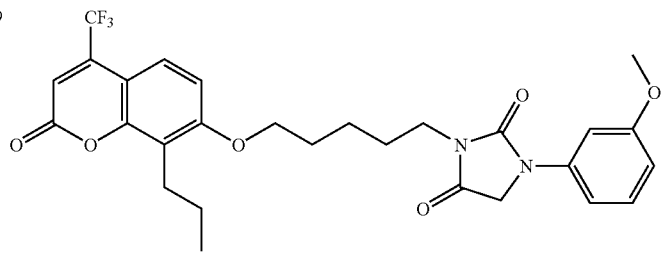 | 1-(3-methoxyphenyl)-3-(5-(2-oxo-8-propyl-4-(trifluoromethyl)-2H-chromen-7-yloxy)pentyl)imidazolidin-2,4-dione |
| Example 120 | 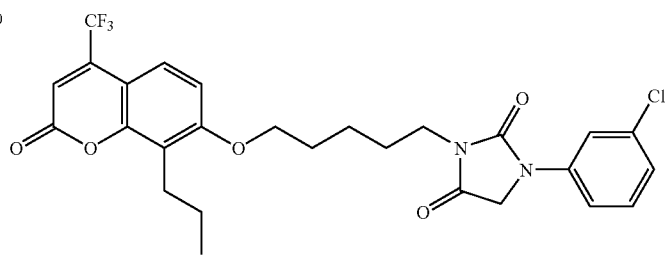 | 1-(3-chlorophenyl)-3-(5-(2-oxo-8-propyl-4-(trifluoromethyl)-2H-chromen-7-yloxy)pentyl)imidazolidin-2,4-dione |

TABLE 1-14

| Example 121 | 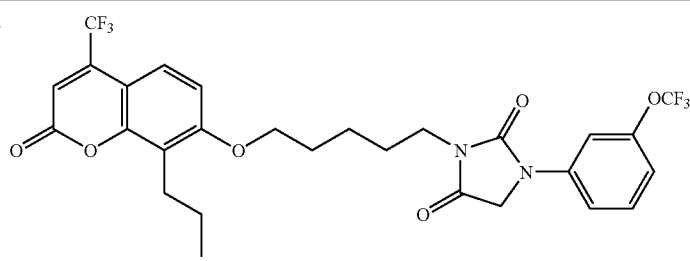 | 3-(5-(2-oxo-8-propyl-4-(trifluoromethyl)-2H-chromen-7-yloxy)pentyl)-1-(3-(trifluoromethoxy)phenyl)imidazolidin-2,4-done |
| Example 122 | 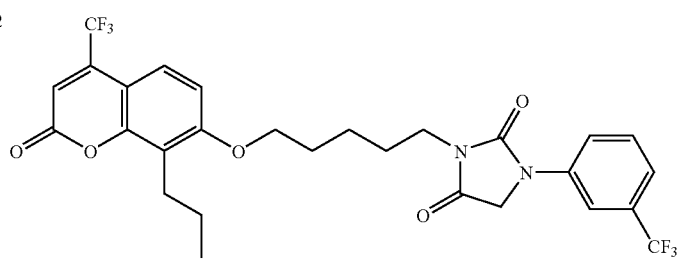 | 3-(5-(2-oxo-8-propyl-4-(trifluoromethyl)-2H-chromen-7-yloxy)pentyl)-1-(3-(trifluoromethyl)phenyl)imidazolidin-2,4-dione |
| Example 123 | 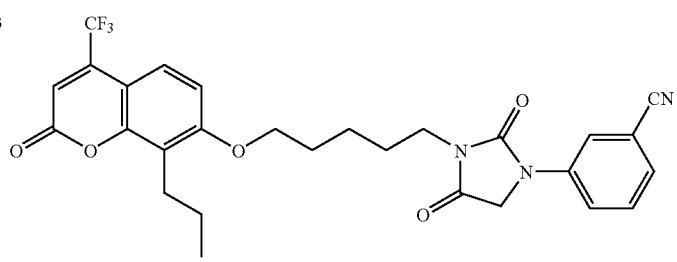 | 3-(2,4-dioxo-3-(5-(2-oxo-8-propyl-4-(trifluoromethyl)-2H-chromen-7-yloxy)pentyl) imidazolidin-1-yl) benzonitrile |

TABLE 1-14-continued

| Example 124 | 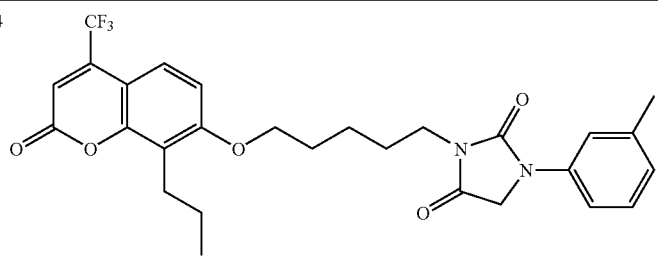 | 3-(5-(2-oxo-8-propyl-4-(trifluoromethyl)-2H-chromen-7-yloxy)pentyl)-1-m-tolylimidazolidin-2,4-dione |
| Example 125 | 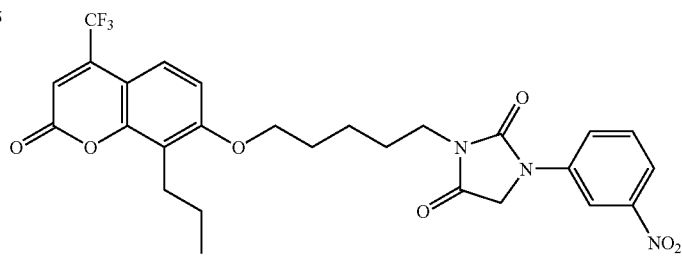 | 1-(3-nitrophenyl-3-(5-(2-oxo-8-propyl-4-(trifluoromethyl)-2H-chromen-7-yloxy)pentyl)imidazolidin-2,4-dione |
| Example 126 | 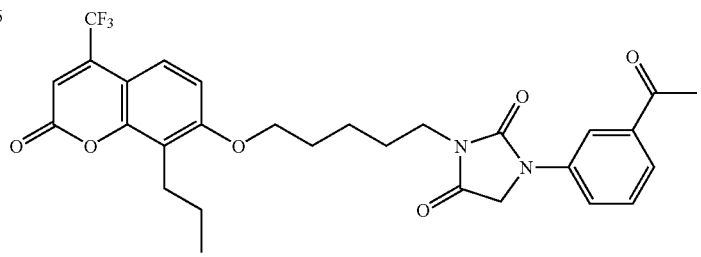 | 1-(3-acetylphenyl-3-(5-(2-oxo-8-propyl-4-(trifluoromethyl)-2H-chromen-7-yloxy)pentyl)imidazolidin-2,4-dione |
| Example 127 | 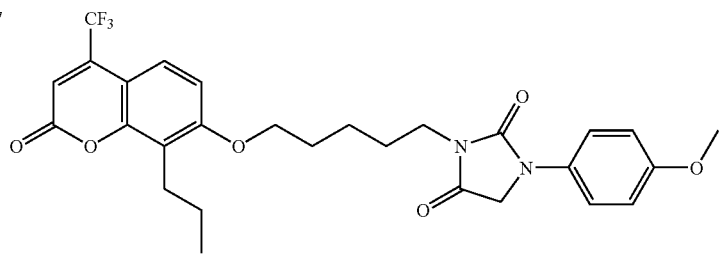 | 1-(4-methoxyphenyl-3-(5-(2-oxo-8-propyl-4-(trifluoromethyl)-2H-chromen-7-yloxy)pentyl)imidazolidin-2,4-dione |
| Example 128 | 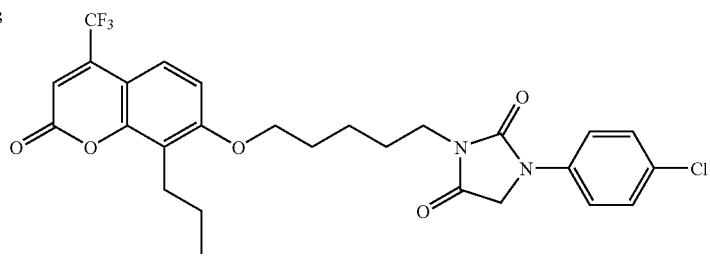 | 1-(4-chlorophenyl)-3-(5-(2-oxo-8-propyl-4-(trifluoromethyl)-2H-chromen-7-yloxy)pentyl)imidazolidin-2,4-dione |

TABLE 1-15

| Example 129 | 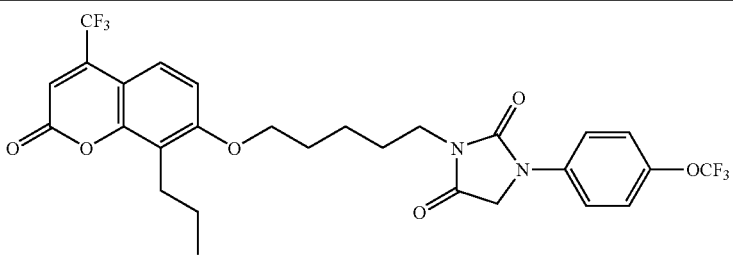 | 3-(5-(2-oxo-8-propyl-4-(trifluoromethyl)-2H-chromen-7-yloxy)pentyl)-1-(4-(trifluoromethoxy)phenyl)imidazolidin-2,4-dione |

TABLE 1-15-continued

| Example 130 | 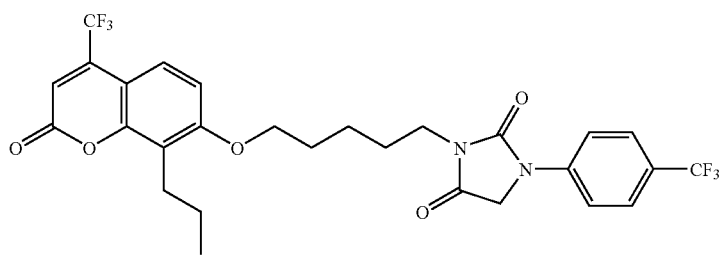 | 3-(5-(2-oxo-8-propyl-4-(trifluoromethyl)-2H-chromen-7-yloxy)pentyl)-1-(4-(trifluoromethyl)phenyl)imidazolidin-2,4-dione |
| Example 131 | 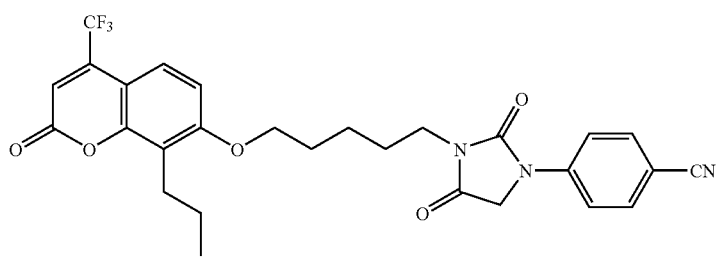 | 4-(2,4-dioxo-3-(5-(2-oxo-8-propyl-4-(trifluoromethyl)-2H-chromen-7-yloxy)pentyl)imidazolidin-1-yl)benzonitrile |
| Example 132 | 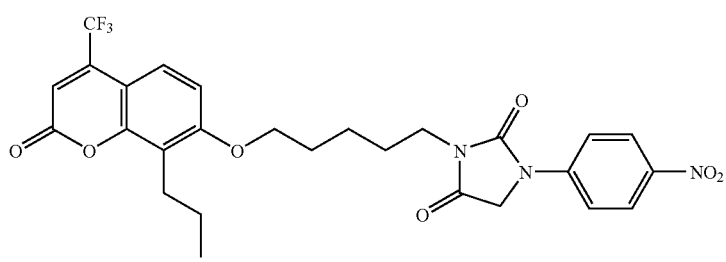 | 1-(4-nitrophenyl)-3-(5-(2-oxo-8-propyl-4-(trifluoromethyl)-2H-chromen-7-yloxy)pentyl)imidazolidin-2,4-dione |
| Example 133 | 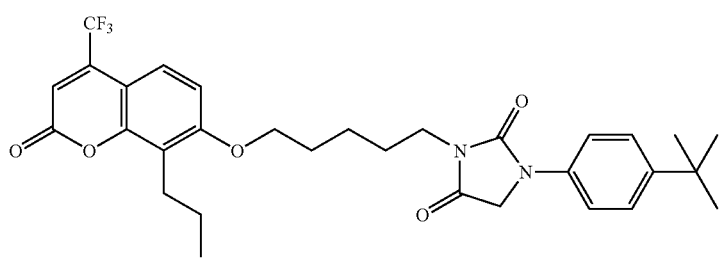 | 1-(4-tert-butylphenyl)-3-(5-(2-oxo-8-propyl-4-(trifluoromethyl)-2H-chromen-7-yloxy)pentyl)imidazolidin-2,4-dione |
| Example 134 | 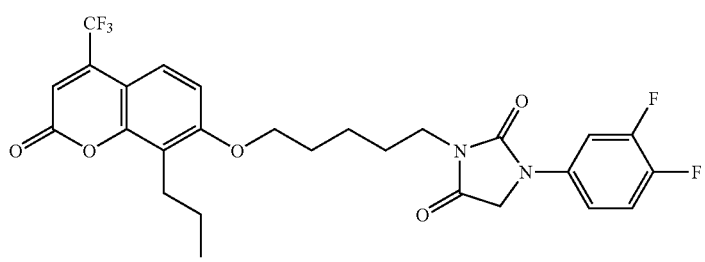 | 1-(3,4-difluorophenyl)-3-(5-(2-oxo-8-propyl-4-(trifluoromethyl)-2H-chromen-7-yloxy)pentyl)imidazolidin-2,4-dione |
| Example 135 | 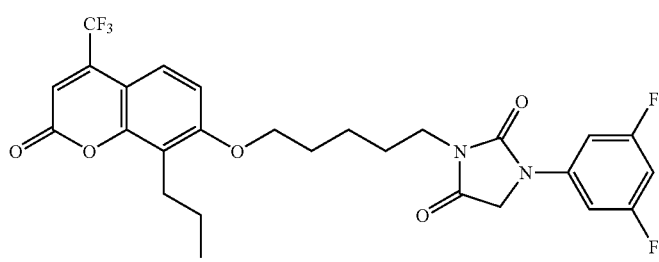 | 1-(3,5-difluorophenyl)-3-(5-(2-oxo-8-propyl-4-(trifluormethyl)-2H-chromen-7-yloxy)pentyl)imidazolidin-2,4-dione |

TABLE 1-15-continued

| Example 136 | 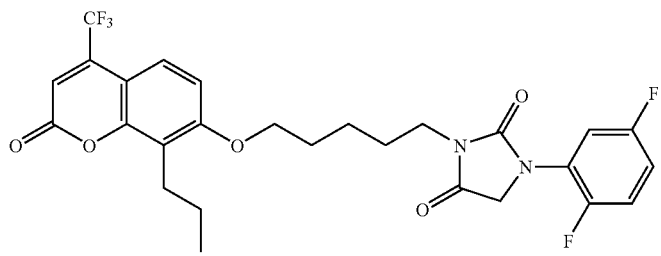 | 1-(2,5-difluorophenyl)-3-(5-(2-oxo-8-propyl-4-(trifluoromethyl)-2H-chromen-7-yloxy)pentyl)imidazolidin-2,4-dione |

TABLE 1-16

| Example 137 | 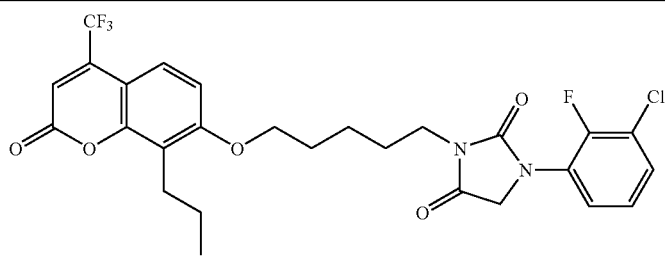 | 1-(3-chloro-2-fluorophenyl)-3-(5-(2-oxo-8-propyl-4-(trifluoromethyl)-2H-chromen-7-yloxy)pentyl)imidazolidin-2,4-dione |
| Example 138 | 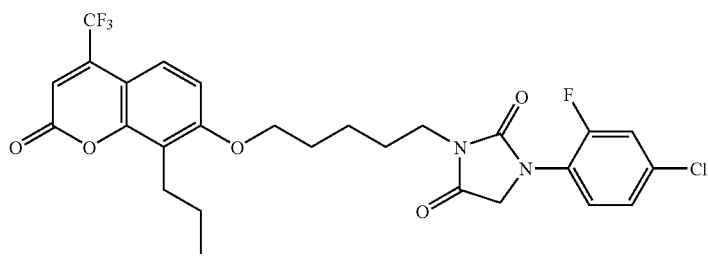 | 1-(4-chloro-2-fluorophenyl)-3-(5-(2-oxo-8-propyl-4-(trifluoromethyl)-2H-chromen-7-yloxy)pentyl)imidazolidin-2,4-dione |
| Example 139 | 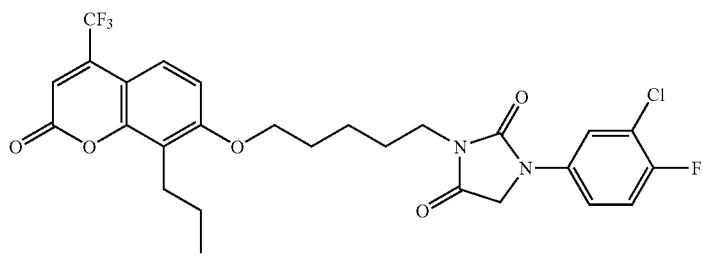 | 1-(3-chloro-4-fluorophenyl)-3-(5-(2-oxo-8-propyl-4-(trifluoromethyl)-2H-chromen-7-yloxy)pentyl)imidazolidin-2,4-dione |
| Example 140 | 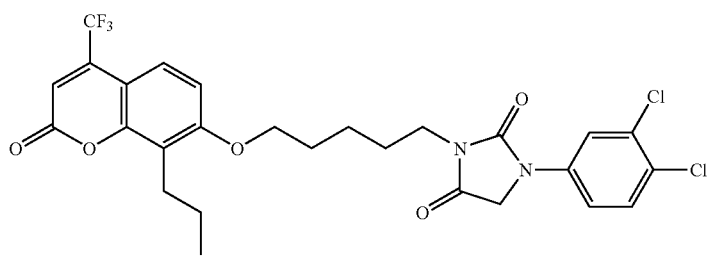 | 1-(3,4-dichlorophenyl)-3-(5-(2-oxo-8-propyl-4-(trifluoromethyl)-2H-chromen-7-yloxy)pentyl)imidazolidin-2,4-dione |

TABLE 1-16-continued

| Example 141 | 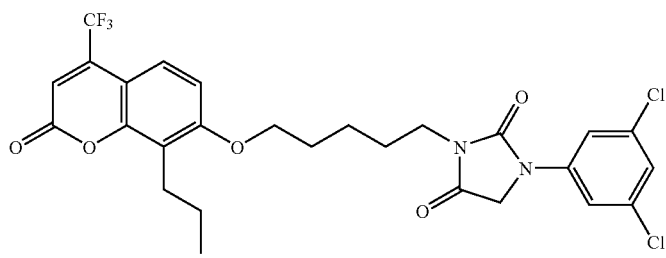 | 1-(3,5-dichlorophenyl)-3-(5-(2-oxo-8-propyl-4-(trifluoromethyl)-2H-chromen-7-yloxy)pentyl)imidazolidin-2,4-dione |
| Example 142 | 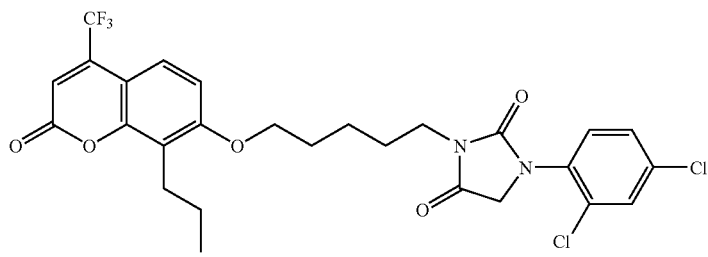 | 1-(2,4-dichlorophenyl)-3-(5-(2-oxo-8-propyl-4-(trifluoromethyl)-2H-chromen-7-yloxy)pentyl)imidazolidin-2,4-dione |
| Example 143 | 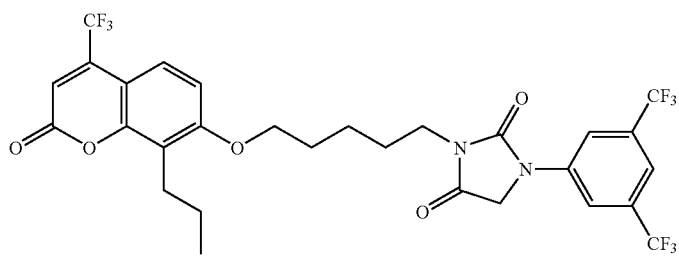 | 1-(3,5-bis(trifluoromethyl)phenyl)-3-(5-(2-oxo-8-propyl-4-(trifluoromethyl)-2H-chromen-7-yloxy)pentyl)imidazolidin-2,4-dione |
| Example 144 | 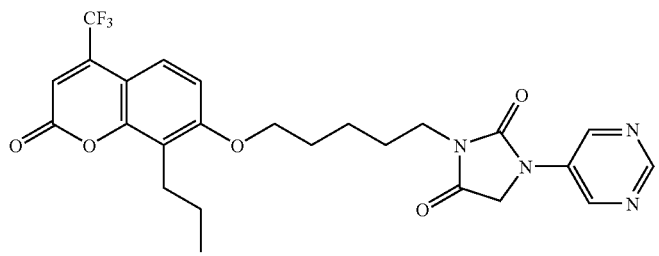 | 3-(5-(2-oxo-8-propyl-4-(trifluoromethyl)-2H-chromen-7-yloxy)pentyl)-1-(pyrimidin-5-yl)imidazolidin-2,4-dione |

TABLE 1-17

| Example 145 | 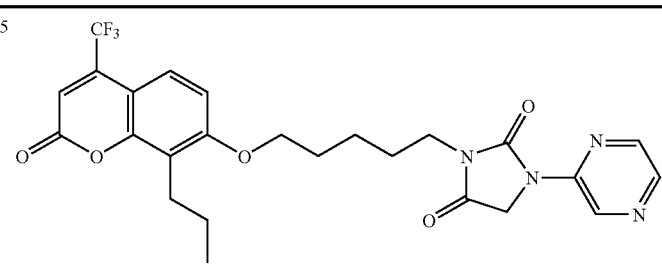 | 3-(5-(2-oxo-8-propyl-4-(trifluoromethyl)-2H-chromen-7-yloxy)pentyl)-1-pyrazin-2-yl)imidazolidin-2,4-dione |

TABLE 1-17-continued

| Example | Structure | Name |
|---|---|---|
| Example 146 | 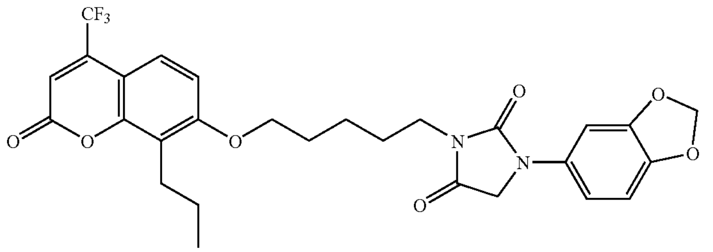 | 1-(benzo[d][1,3]dioxol-5-yl)-3-(5-(2-oxo-8-propyl-4-(trifluoromethyl)-2H-chromen-7-yloxy)pentyl)imidazolidin-2,4-dione |
| Example 147 | 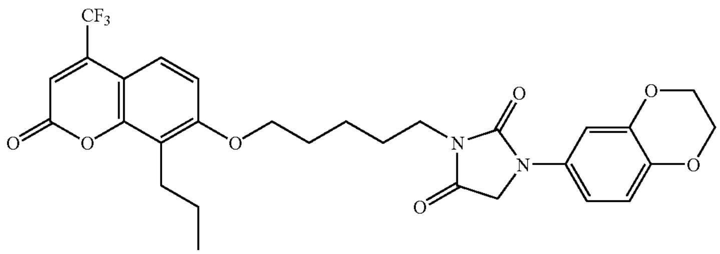 | 1-(2,3-dihydrobenzo-[b][1,4]dioxin-6-yl)-3-(5-(2-oxo-8-propyl-4-(trifluoromethyl)-2H-chromen-7-yloxy)pentyl)imidazolidin-2,4-dione |
| Example 148 | 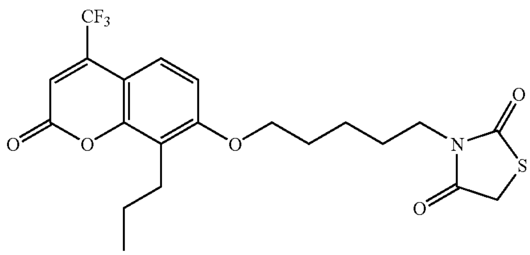 | 3-(5-(2-oxo-8-propyl-4-(trifluoromethyl)-2H-chromen-7-yloxy)pentyl)thiazolidin-2,4-dione |
| Example 149 | 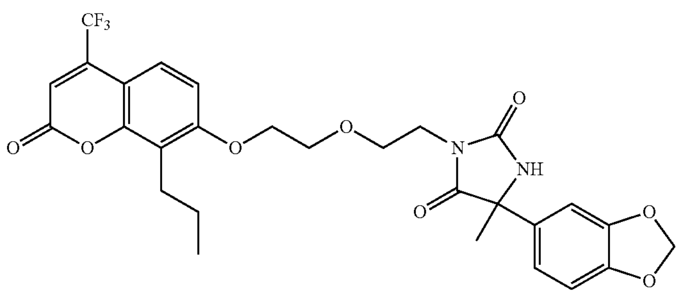 | 5-(benzo[d[[1,3]dioxol-5-yl)-5-methyl-3-(2-(2-(2-oxo-8-propyl-4-(trifluoromethyl)-2H-chromen-7-yloxy)ethoxy)ethyl)imidazolidin-2,4-dione |
| Example 150 | 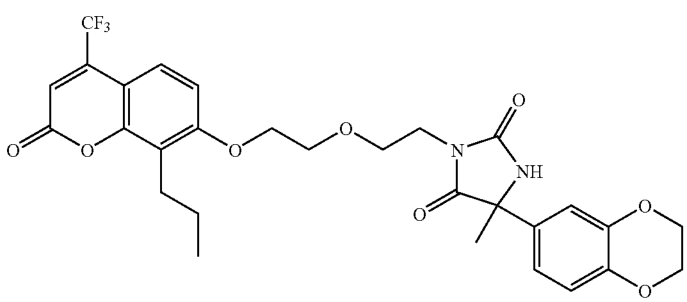 | 5-(2,3-dihydrobenzo[b][1,4]dioxin-6-yl)-5-methyl-3-(2-(2-(2-oxo-8-propyl-4-(trifluoromethyl)-2H-chromen-7-yloxy)ethoxy)ethyl)imidazolidin-2,4-dione |
| Example 151 | 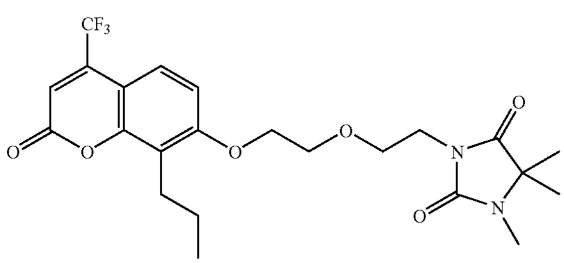 | 1,5,5-trimethyl-3-(2-(2-(2-oxo-8-propyl-4-(trifluoromethyl)-2H-chromen-7-yloxy)ethoxy)ethyl)imidazolidin-2,4-dione |

TABLE 1-17-continued

| Example 152 | 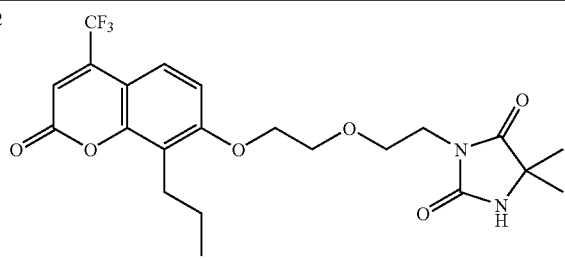 | 5,5-dimethyl-3-(2-(2-(2-oxo-8-propyl-4-(trifluoromethyl)-2H-chromen-7-yloxy)ethoxy)ethyl)imidazolidin-2,4-dione |

TABLE 1-18

| Example 153 | 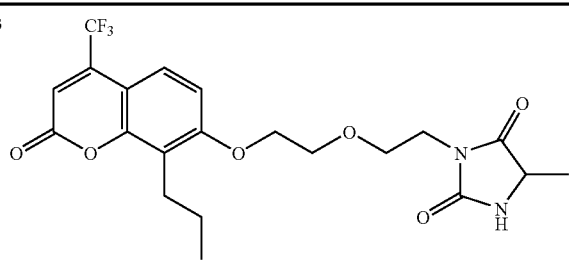 | 5-methyl-3-(2-(2-(2-oxo-8-propyl-4-(trifluoromethyl)-2H-chromen-7-yloxy)ethoxy)ethyl)imidazolidin-2,4-dione |
| Example 154 | 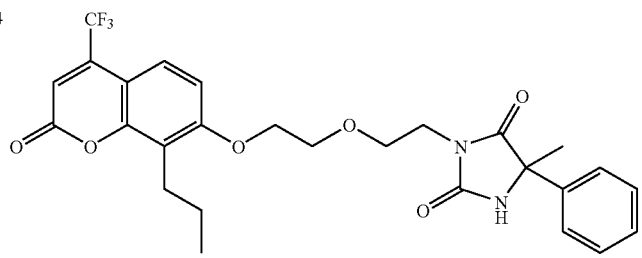 | 5-methyl-3-(2-(2-(2-oxo-8-propyl-4-(trifluoromethyl)-2H-chromen-7-yloxy)ethoxy)ethyl)-5-phenylimidazolidin-2,4-dione |
| Example 155 | 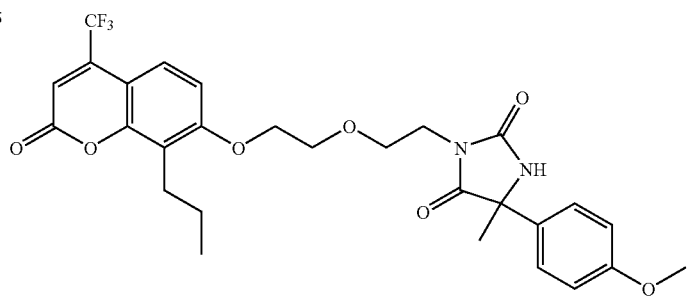 | 5-(4-methoxyphenyl-5-methyl-3-(2-(2-(2-oxo-8-propyl-4-(trifluoromethyl)-2H-chromen-7-yloxy)ethoxy)ethyl)imidazolidin-2,4-dione |
| Example 156 | 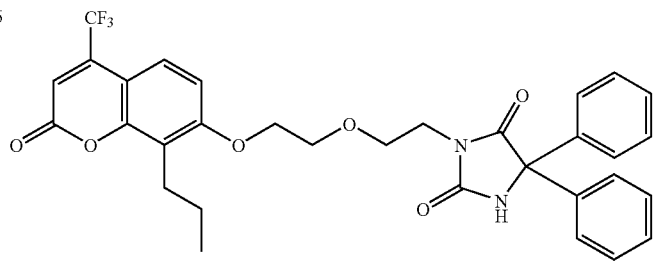 | 3-(2-(2-(2-oxo-8-propyl-4-(trifluoromethyl)-2H-chromen-7-yloxy)ethoxy)ethyl)-5,5-diphenylimidazolidin-2,4-dione |

TABLE 1-18-continued

| Example 157 | 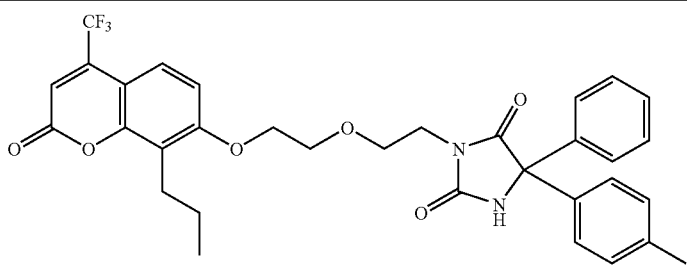 | 3-(2-(2-(2-oxo-8-propyl-4-(trifluoromethyl)-2H-chromen-7-yloxy)ethoxy)ethyl)-5-phenyl-5-p-tolylimidazolidin-2,4-dione |

TABLE 1-19

| Example 158 | 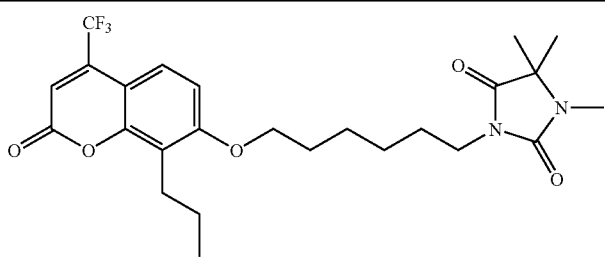 | 1,5,5-trimethyl-3-(6-(2-oxo-8-propyl-4-(trifluoromethyl)-2H-chromen-7-yloxy)hexyl)imidazolidin-2,4-dione |
| Example 159 | 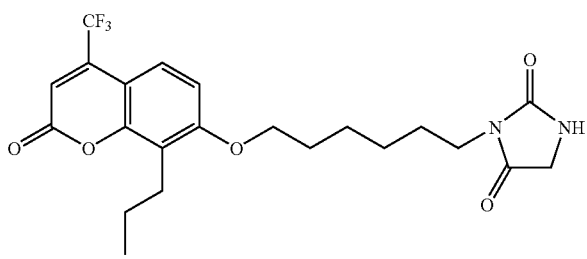 | 3-(6-(2-oxo-8-propyl-4-(trifluoromethyl)-2H-chromen-7-yloxy)hexyl)imidazolidin-2,4-dione |
| Example 160 | 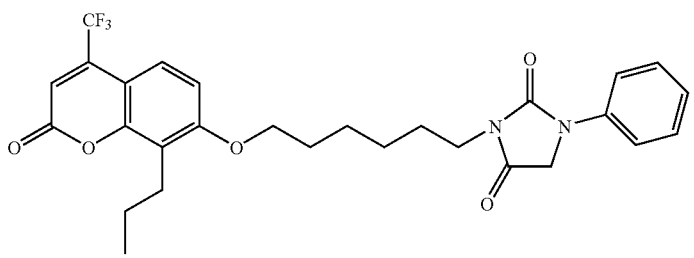 | 3-(6-(2-oxo-8-propyl-4-(trifluoromethyl)-2H-chromen-7-yloxy)hexyl)-1-phenylimidazolidin-2,4-dione |
| Example 161 | 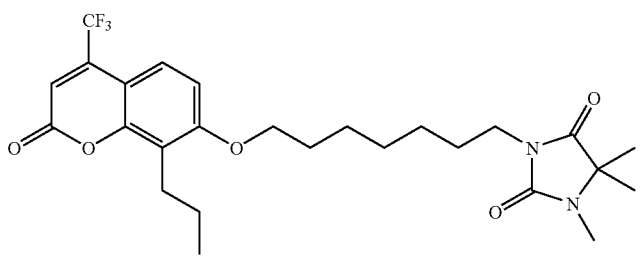 | 1,5,5-trimethyl-3-(7-(2-oxo-8-propyl-4-(trifluoromethyl)-2H-chromen-7-yloxy)heptyl)imidazolidin-2,4-dione |

TABLE 1-19-continued

Example 162
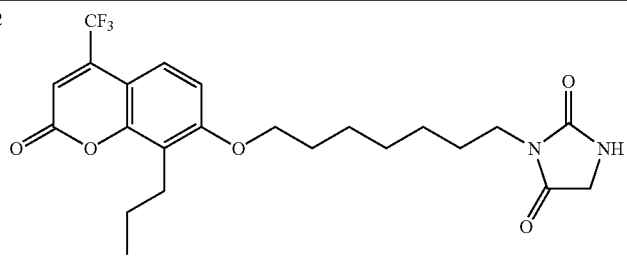
3-(7-(2-oxo-8-propyl-4-(trifluoromethyl)-2H-chromen-7-yloxy)heptyl)imidazolidin-2,4-dione Example 163
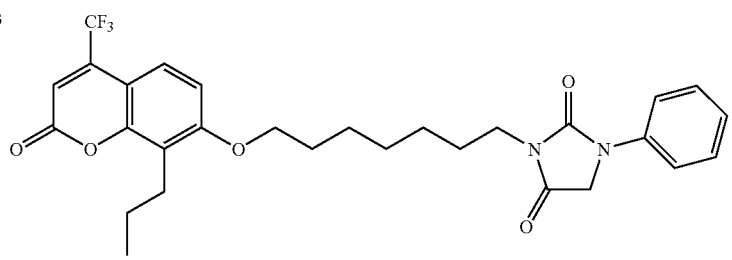
3-(7-(2-oxo-8-propyl-4-(trifluoromethyl)-2H-chromen-7-yloxy)heptyl)-1-phenylimidazolidin-2,4-dione

TABLE 1-20

Example 164
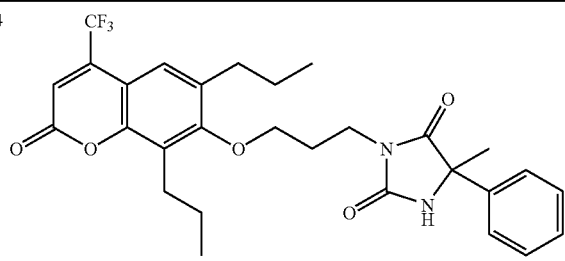
5-methyl-3-(3-(2-oxo-6,8-dipropyl-4-(trifluoromethyl)-2H-chromen-7-yloxy)propyl)-5-phenylimidazolidin-2,4-dione Example 165
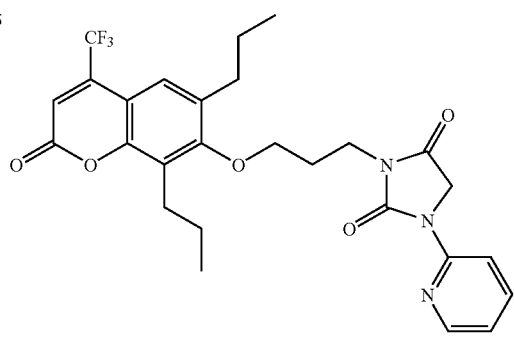
3-(3-(2-oxo-6,8-dipropyl-4-(trifluoromethyl)-2H-chromen-7-yloxy)propyl)-1-(pyridin-2-yl)imidazolidin-2,4-dione Example 166
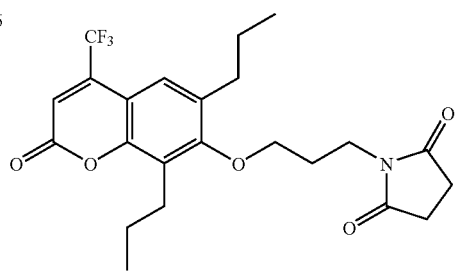
1-(3-(2-oxo-6,8-dipropyl-4-(trifluoromethyl)-2H-chromen-7-yloxy)propyl)pyrrolidin-2,5-dione TABLE 1-20-continued Example 167 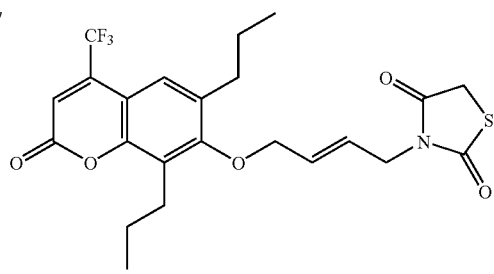 (E)-3-(4-(2-oxo-6,8-dipropyl-4-(trifluoromethyl)-2H-chromen-7-yloxy)but-2-enyl)thiazolidin-2,4-dione Example 168 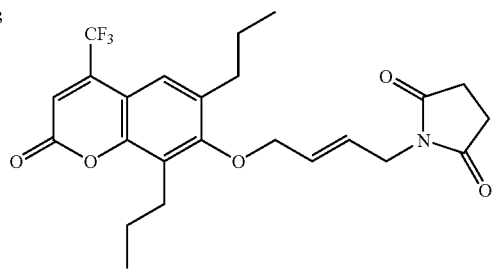 (E)-1-(4-(2-oxo-6,8-dipropyl-4-(trifluoromethyl)-2H-chromen-7-yloxy)but-2-enyl)pyrrolidin-2,5-dione Example 169 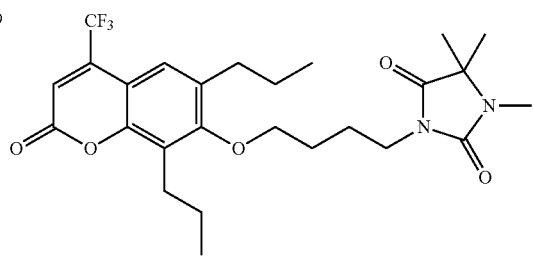 1,5,5-trimethyl-3-(4-(2-oxo-6,8-dipropyl-4-(trifluoromethyl)-2H-chromen-7-yloxy)butyl)imidazolidin-2,4-dione Example 170 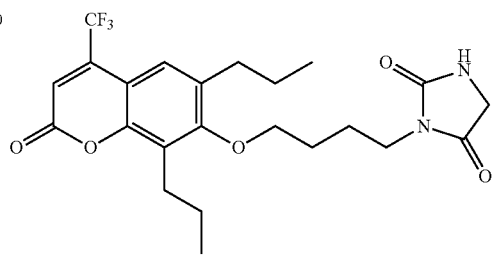 3-(4-(2-oxo-6,8-dipropyl-4-(trifluoromethyl)-2H-chromen-7-yloxy)butyl)imidazolidin-2,4-dione Example 171 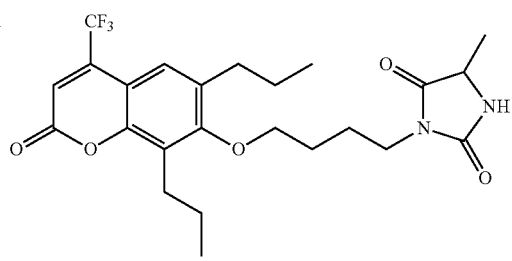 5-methyl-3-(4-(2-oxo-6,8-dipropyl-4-(trifluoromethyl)-2H-chromen-7-yloxy)butyl)imidazolidin-2,4-dione Example 172 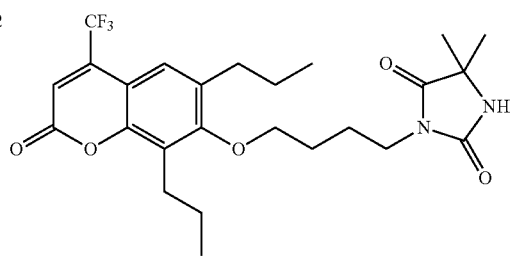 5,5-dimethyl-3-(4-(2-oxo-6,8-dipropyl-4-(trifluoromethyl)-2H-chromen-7-yloxy)butyl)imidazolidin-2,4-dione TABLE 1-20-continued
Example 173 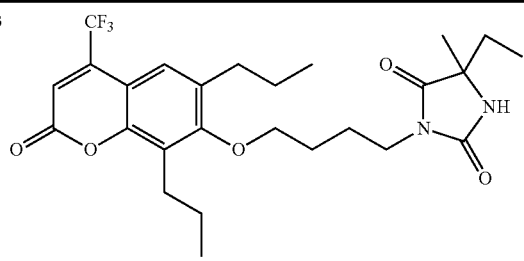 5-ethyl-5-methyl-3-(4-(2-oxo-6,8-dipropyl-4-(trifluoromethyl)-2H-chromen-7-yloxy)butyl)imidazolidin-2,4-dione
TABLE 1-21
Example 174 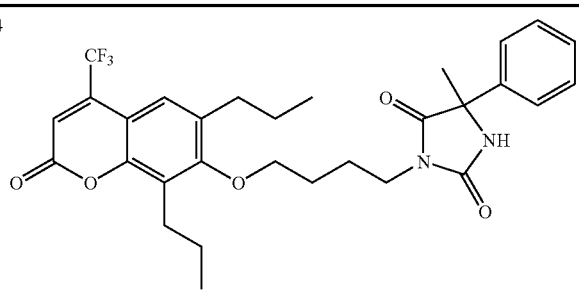
Example 175 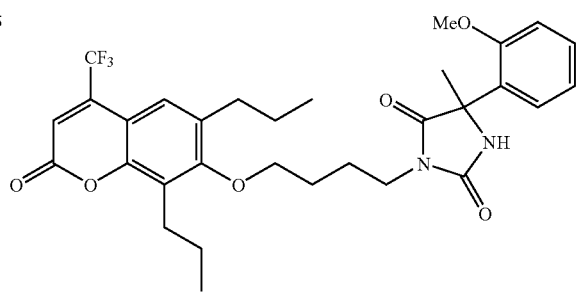
Example 176 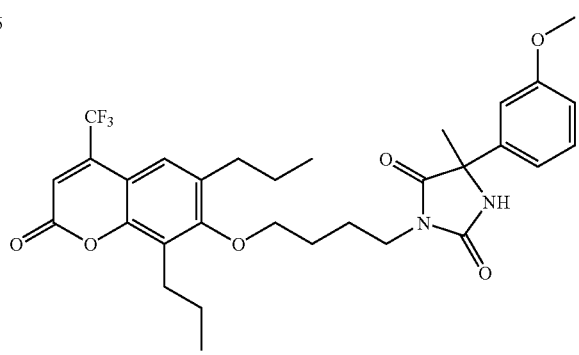

TABLE 1-21-continued

Example 177

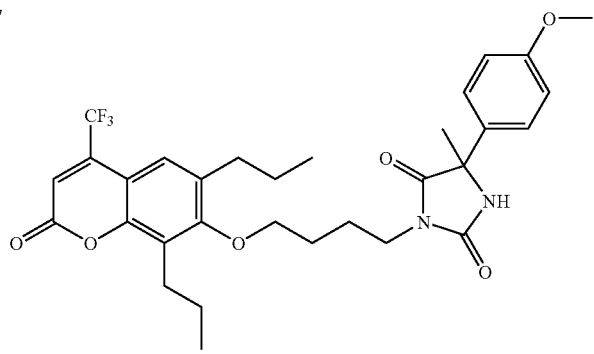

Example 178

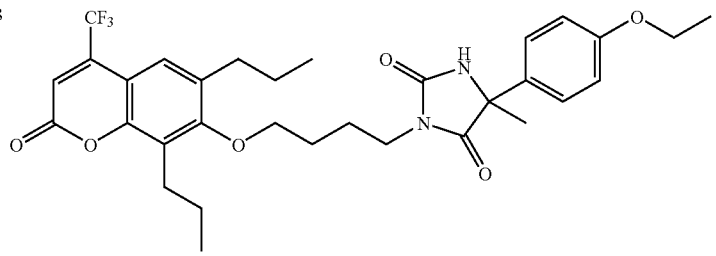

Example 179

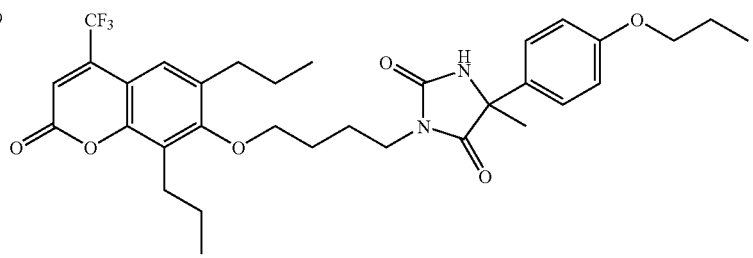

Example 180

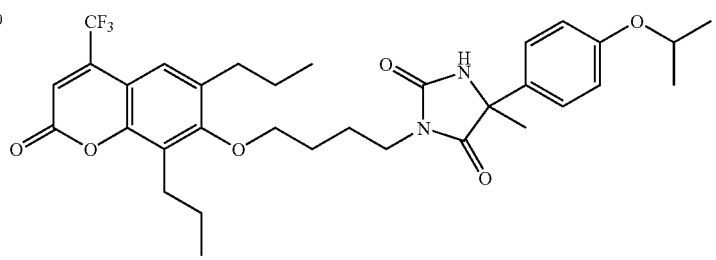

Example 181

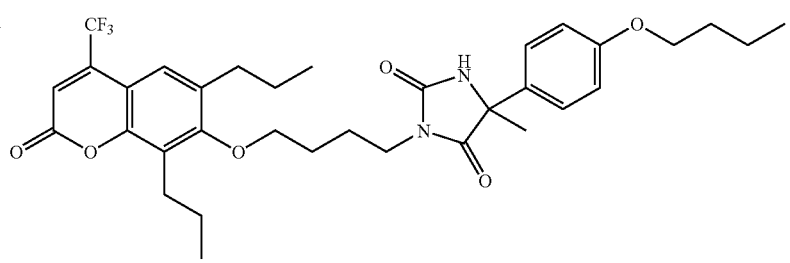

Example 174  5-methyl-3-(4-(2-oxo-6,8-dipropyl-4-(trifluoromethyl)-2H-chromen-7-yloxy)butyl)-5-phenylimidazolidin-2,4-dione
Example 175  5-(3-methoxyphenyl)-5-methyl-3-(4-(2-oxo-6,8-dipropyl-4-(trifluoromethyl)-2H-chromen-7-yloxy)butyl)imidazolidin-2,4-dione
Example 176  5-(3-methoxyphenyl)-5-methyl-3-(4-(2-oxo-6,8-dipropyl-4-(trifluoromethyl)-2H-chromen-7-yloxy)butyl)imidazolidin-2,4-dione
Example 177  5-(4-methoxyphenyl)-5-methyl-3-(4-(2-oxo-6,8-dipropyl-4-(trifluoromethyl)-2H-chromen-7-yloxy)butyl)imidazolidin-2,4-dione TABLE 1-21-continued

| | |
|---|---|
| Example 178 | 5-(4-ethoxyphenyl-5-methyl-3-(4-(2-oxo-6,8-dipropyl-4-(trifluoromethyl)-2H-chromen-7-yloxy)butyl)imidazolidin-2,4-dione |
| Example 179 | 5-methyl-3-(4-(2-oxo-6,8-dipropyl-4-(trifluoromethyl)-2H-chromen-7-yloxy)butyl)-5-(4-propoxyphenyl)imidazolidin-2,4-dione |
| Example 180 | 5-(4-isopropoxyphenyl)-5-methyl-3-(4-(2-oxo-6,8-dipropyl-4-(trifluoromethyl)-2H-chromen-7-yloxy)butyl)imidazolidin-2,4-dione |
| Example 181 | 5-(4-butoxyphenyl)-5-methyl-3-(4-(2-oxo-6,8-dipropyl-4-(trifluoromethyl)-2H-chromen-7-yloxy)butyl)imidazolidin-2,4-dione |

TABLE 1-22

Example 182

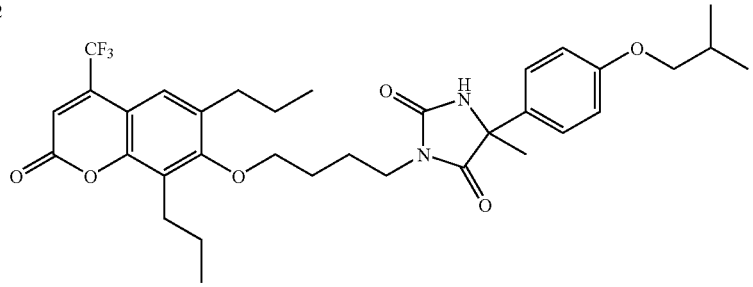

Example 183

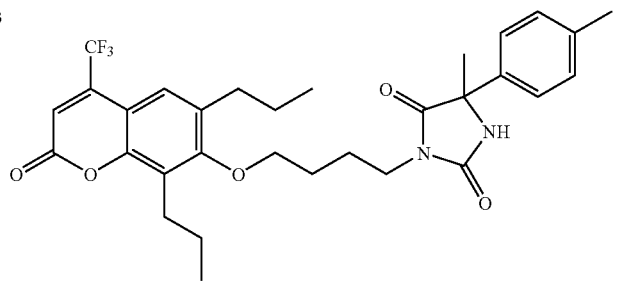

Example 184

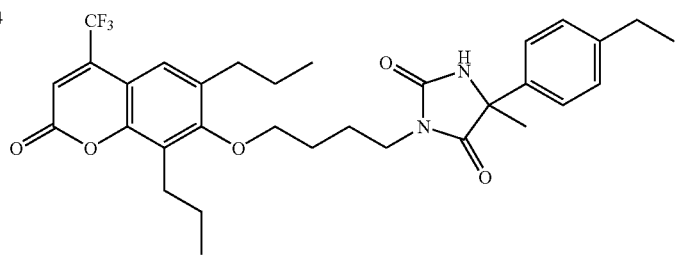

Example 185

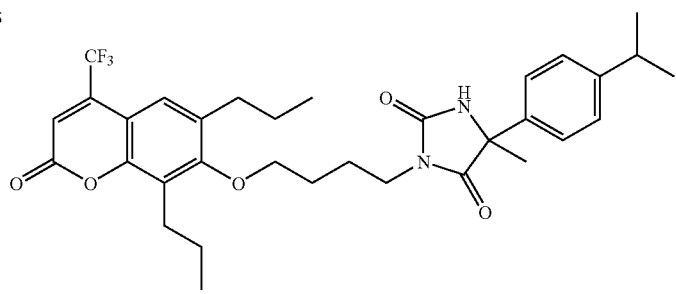

TABLE 1-22-continued

Example 186

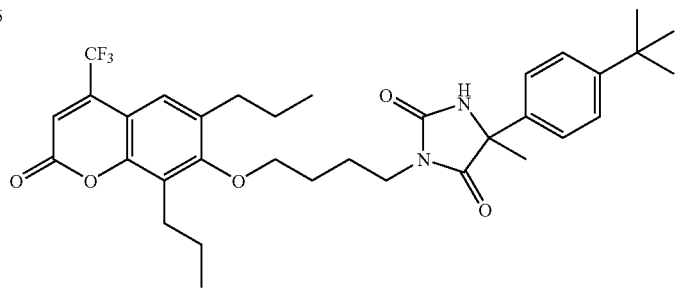

Example 187

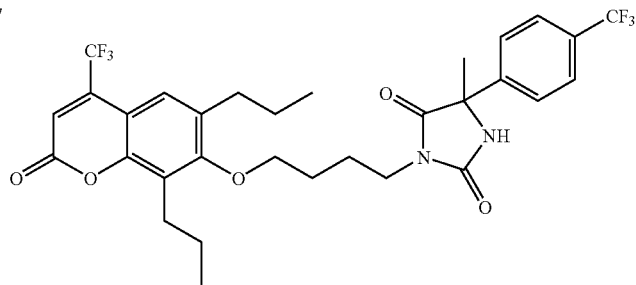

Example 188

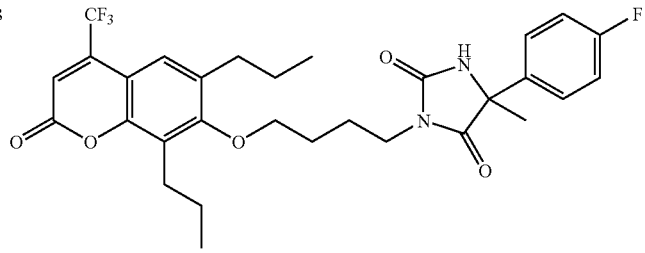

Example 189

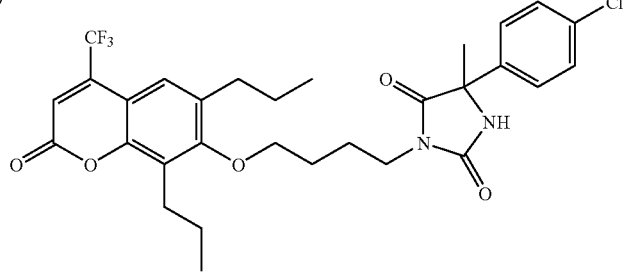

Example 182 5-(4-isobutoxyphenyl)-5-methyl-3-(4-(2-oxo-6,8-dipropyl-4-(trifluoromethyl)-2H-chromen-7-yloxy)butyl)imidazolidin-2,4-dione Example 183 5-methyl-3-(4-(2-oxo-6,8-dipropyl-4-(trifluoromethyl)-2H-chromen-7-yloxy)butyl)-5-p-tolylimidazolidin-2,4-dione Example 184 5-(4-ethylphenyl)-5-methyl-3-(4-(2-oxo-6,8-dipropyl-4-(trifluoromethyl)-2H-chromen-7-yloxy)butyl)imidazolidin-2,4-dione Example 185 5-(4-isopropylphenyl-5-methyl-3-(4-(2-oxo-6,8-dipropyl-4-(trifluoromethyl)-2H-chromen-7-yloxy)butyl)imidazolidin-2,4-dione Example 186 5-(4-tert-butylphenyl-5-methyl-3-(4-(2-oxo-6,8-dipropyl-4-(trifluoromethyl)-2H-chromen-7-yloxy)butyl)imidazolidin-2,4-dione Example 187 5-methyl-3-(4-(2-oxo-6,8-dipropyl-4-(trifluoromethyl)-2H-chromen-7-yloxy)butyl)-5-(4-(trifluoromethyl)phenyl)imidazolidin-2,4-dione Example 188 5-(4-fluorophenyl)-5-methyl-3-(4-(2-oxo-6,8-dipropyl-4-(trifluoromethyl)-2H-chromen-7-yloxy)butyl)imidazolidin-2,4-dione Example 189 5-(4-chlorophenyl)-5-methyl-3-(4-(2-oxo-6,8-dipropyl-4-(trifluoromethyl)-2H-chromen-7-yloxy)butyl)imidazolidin-2,4-dione TABLE 1-23
Example 190
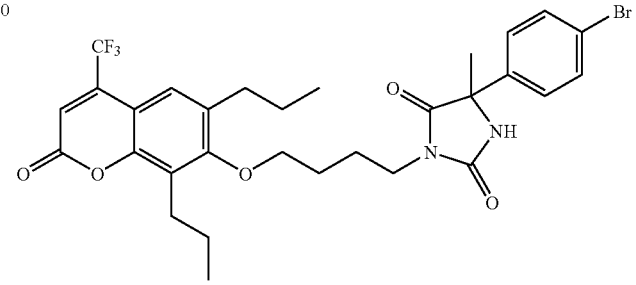
Example 191
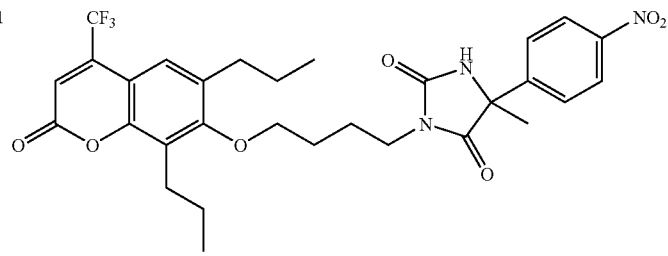
Example 192
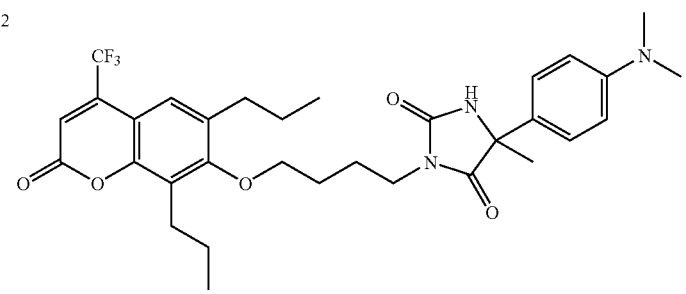
Example 193
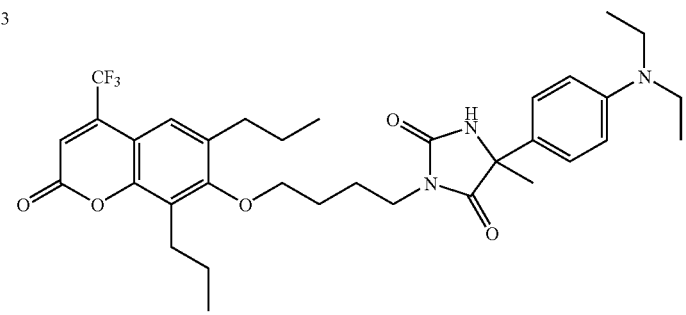
Example 194
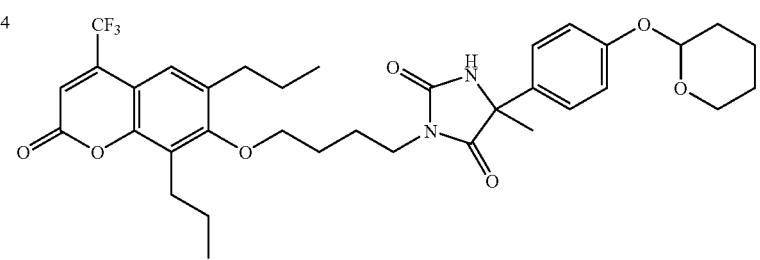

TABLE 1-23-continued

Example 195
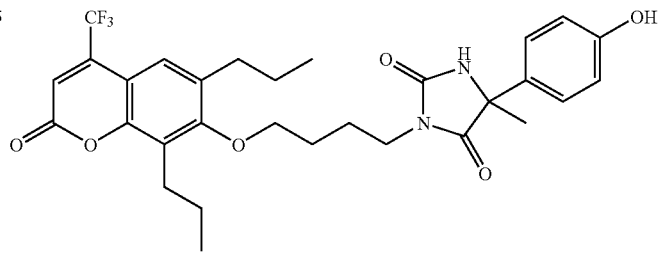

Example 196
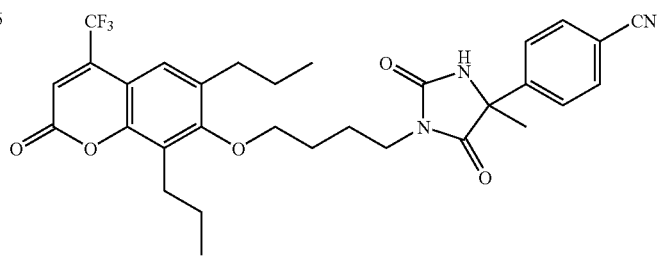

Example 197
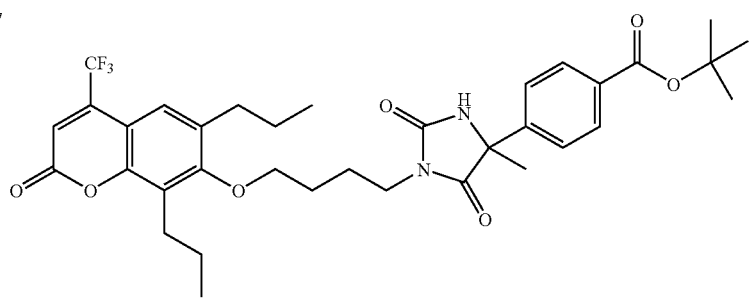

| | |
|---|---|
| Example 190 | 5-(4-bromophenyl)-5-methyl-3-(4-(2-oxo-6,8-dipropyl-4-(trifluoromethyl)-2H-chromen-7-yloxy)butyl)imidazolidin-2,4-dione |
| Example 191 | 5-methyl-5-(4-nitrophenyl)-3-(4-(2-oxo-6,8-dipropyl-4-(trifluoromethyl)-2H-chromen-7-yloxy)butyl)imidazolidin-2,4-dione |
| Example 192 | 5-(4-(dimethylamino)phenyl)-5-methyl-3-(4-(2-oxo-6,8-dipropyl-4-(trifluoromethyl)-2H-chromen-7-yloxy)butyl)imidazolidin-2,4-dione |
| Example 193 | 5-(4-(diethylamino)phenyl)-5-methyl-3-(4-(2-oxo-6,8-dipropyl-4-(trifluoromethyl)-2H-chromen-7-yloxy)butyl)imidazolidin-2,4-dione |
| Example 194 | 5-methyl-3-(4-(2-oxo-6,8-dipropyl-4-(trifluoromethyl)-2H-chromen-7-yloxy)butyl)-5-(4-(tetrahydra-2H-pyran-2-yloxy)phenyl)imidazolidin-2,4-dione |
| Example 195 | 5-(4-hydroxyphenyl)-5-methyl-3-(4-(2-oxo-6,8-dipropyl-4-(trifluoromethyl)-2H-chromen-7-yloxy)butyl)imidazolidin-2,4-dione |
| Example 196 | 4-(4-methyl-2,5-dioxo-1-(4-(2-oxo-6,8-dipropyl-4-(trifluoromethyl)-2H-chromen-7-yloxy)butyl)imidazolidin-4-yl)benzonitrile |
| Example 197 | tert-butyl 4-(4-methyl-2,5-dioxo-1-(4-(2-oxo-6,8-dipropyl-4-(trifluoromethyl)-2H-chromen-7-yloxy)butyl)imidazolidin-4-yl) benzoate |

TABLE 1-24

| Example 198 | [structure] | 4-(4-methyl-2,5-dioxo-1-(4-(2-oxo-6,8-dipropyl-4-(trifluoromethyl)-2H-chromen-7-yloxy)butyl)imidazolidin-4-yl)benzoic acid |
| --- | --- | --- |
| Example 199 | [structure] | 5-(3,4-dimethoxyphenyl-5-methyl-3-(4-(2-oxo-6,8-dipropyl-4-(trifluoromethyl)-2H-chromen-7-yloxy)butyl)imidazolidin-2,4-dione |
| Example 200 | [structure] | 5-methyl-3-(4-(2-oxo-6,8-dipropyl-4-(trifluoromethyl)-2H-chromen-7-yloxy)butyl)-5-(3,4,5-trimethoxyphenyl)imidazolidin-2,4-dione |
| Example 201 | [structure] | 5-(3-fluoro-4-methoxyphenyl)-5-methyl-3-(4-(2-oxo-6,8-dipropyl-4-trifluoromethyl)-2H-chromen-7-yloxy)butyl)imidazolidin-2,4-dione |
| Example 202 | [structure] | 5-(3,4-difluorophenyl)-5-methyl-3-(4-(2-oxo-6,8-dipropyl-4-(trifluoromethyl)-2H-chromen-7-yloxy)butyl)imidazolidin-2,4-dione |
| Example 203 | [structure] | 5-(3,4-dichlorophenyl)-5-methyl-3-(4-(2-oxo-6,8-dipropyl-4-(trifluoromethyl)-2H-chromen-7-yloxy)butyl)imidazolidin-2,4-dione |

TABLE 1-24-continued

| Example 204 | 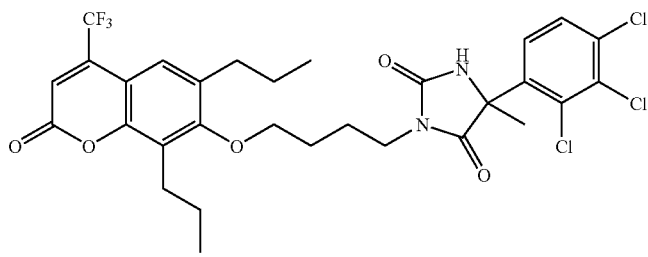 | 5-methyl-3-(4-(2-oxo-6,8-dipropyl-4-(trifluoromethyl)-2H-chromen-7-yloxy)-butyl)-5-(2,3,4-trichlorophenyl)imidazolidin-2,4-dione |
| Example 205 | 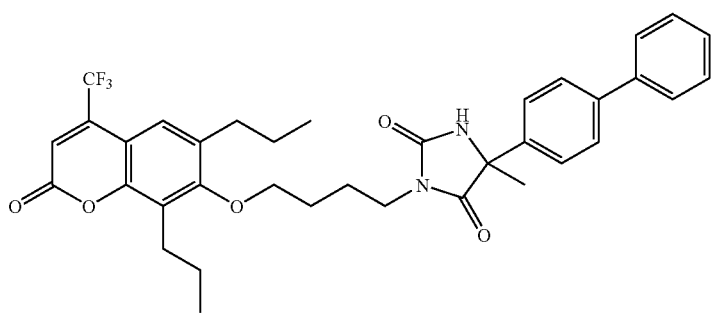 | 5-(biphenyl-4-yl)-5-methyl-3-(4-(2-oxo-6,8-dipropyl-4-(trifluoromethyl)-2H-chromen-7-yloxy)butyl)imidazolidin-2,4-dione |

TABLE 1-25

| Example 206 | 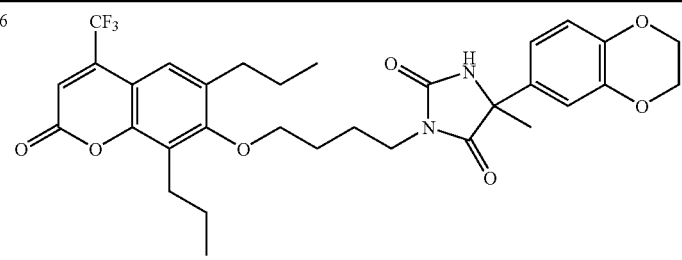 | 5-(2,3-dihydrobenzo[b][1,4]dioxin-6-yl)-5-methyl-3-(4-(2-oxo-6,8-dipropyl-4-(trifluoromethyl)-2H-chromen-7-yloxy)butyl)-imidazolidin-2,4-dione |
| Example 207 | 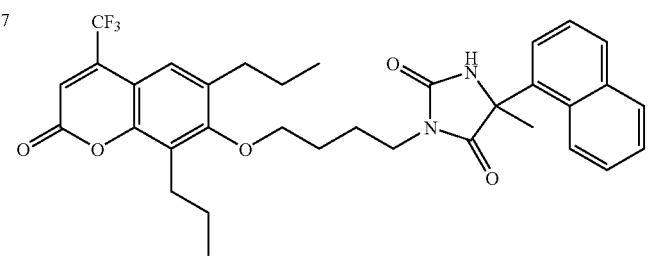 | 5-methyl-5-(naphthalen-1-yl)-3-(4-(2-oxo-6,8-dipropyl-4-(trifluoromethyl)-2H-chromen-7-yloxy)butyl)imidazolidin-2,4-dione |
| Example 208 | 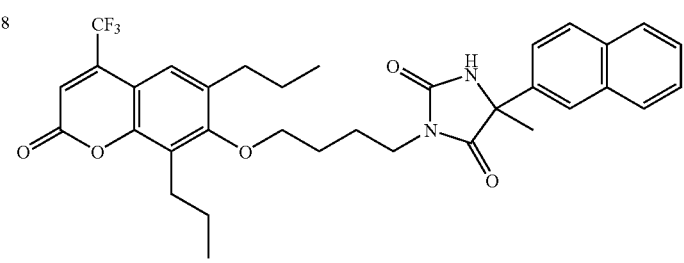 | 5-methyl-5-(naphthalen-2-yl)-3-(4-(2-oxo-6,8-dipropyl-4-(trifluoromethyl)-2H-chromen-7-yloxy)butyl)imidazolidin-2,4-dione |

TABLE 1-25-continued

| Example 209 | 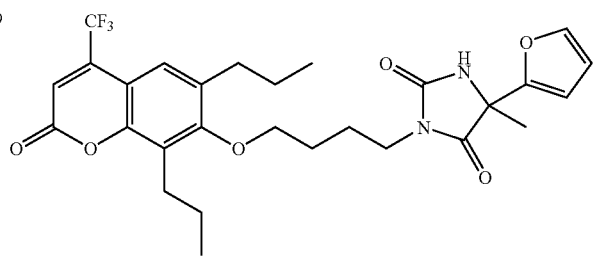 | 5-(furan-2-yl)-5-methyl-3-(4-(2-oxo-6,8-dipropyl-4-(trifluoromethyl)-2H-chromen-7-yloxy)butyl)imidazolidin-2,4-dione |
| Example 210 | 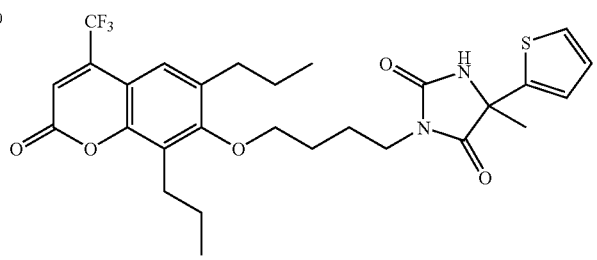 | 5-methyl-3-(4-(2-oxo-6,8-dipropyl-4-(trifluoromethyl)-2H-chromen-7-yloxy)-butyl)-5-(thiophen-2-yl)imidazolidin-2,4-dione |
| Example 211 | 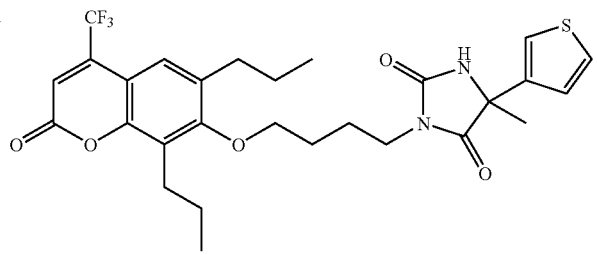 | 5-methyl-3-(4-(2-oxo-6,8-dipropyl-4-(trifluoromethyl)-2H-chromen-7-yloxy)butyl)-5-(thiophen-3-yl)imidazolidin-2,4-dione |
| Example 212 | 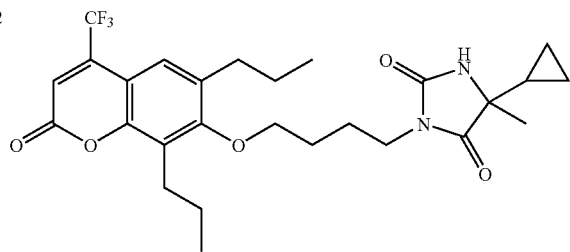 | 5-cyclopropyl-5-methyl-3-(4-(2-oxo-6,8-dipropyl-4-(trifluoromethyl)-2H-chromen-7-yloxy)butyl)imidazolidin-2,4-dione |
| Example 213 | 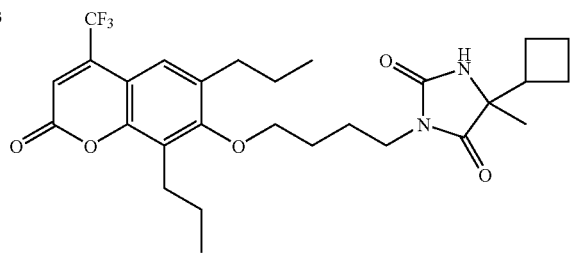 | 5-cyclobutyl-5-methyl-3-(4-(2-oxo-6,8-dipropyl-4-(trifluoromethyl)-2H-chromen-7-yloxy)butyl)imidazolidin-2,4-dione |

TABLE 1-26

| | | |
|---|---|---|
| Example 214 | 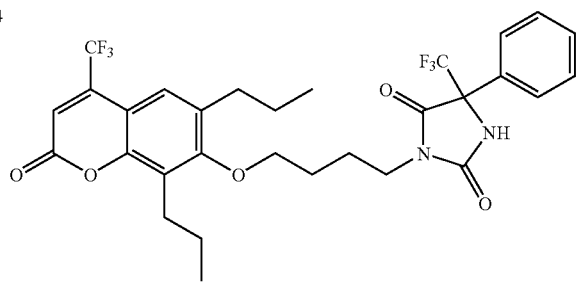 | 3-(4-(2-oxo-6,8-dipropyl-4-(trifluoromethyl)-2H-chromen-7-yloxy)butyl)-5-phenyl-5-(trifluoromethyl)imidazolidin-2,4-dione |
| Example 215 | 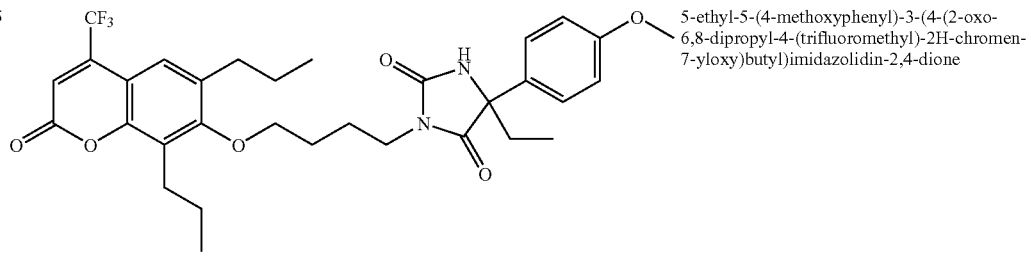 | 5-ethyl-5-(4-methoxyphenyl)-3-(4-(2-oxo-6,8-dipropyl-4-(trifluoromethyl)-2H-chromen-7-yloxy)butyl)imidazolidin-2,4-dione |
| Example 216 | 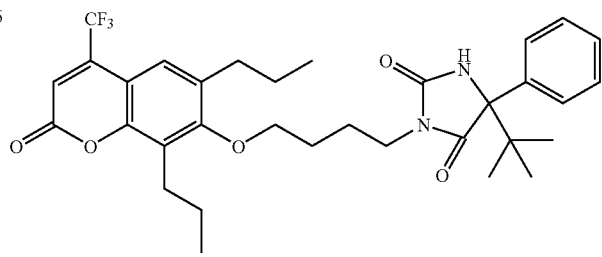 | 5-tert-butyl-3-(4-(2-oxo-6,8-dipropyl-4-(trifluoromethyl)-2H-chromen-7-yloxy)butyl)-5-phenylimidazolidin-2,4-dione |
| Example 217 | 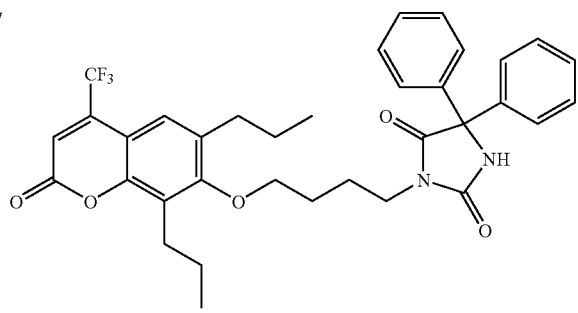 | 3-(4-(2-oxo-6,8-dipropyl-4-(trifluoromethyl)-2H-chromen-7-yloxy)butyl)-5,5-diphenylimidazolidin-2,4-dione |
| Example 218 | 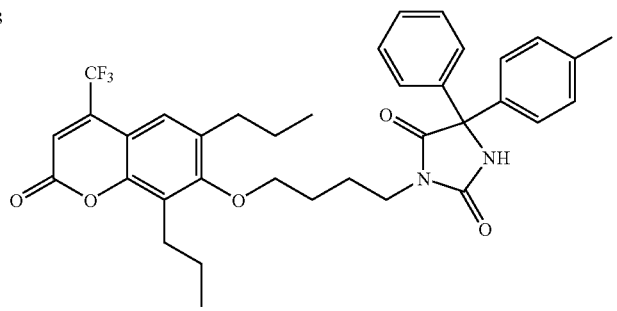 | 3-(4-(2-oxo-6,8-dipropyl-4-(trifluoromethyl)-2H-chromen-7-yloxy)butyl)-5-phenyl-5-p-tolylimidazolidin-2,4-dione |

TABLE 1-26-continued

| Example 219 | 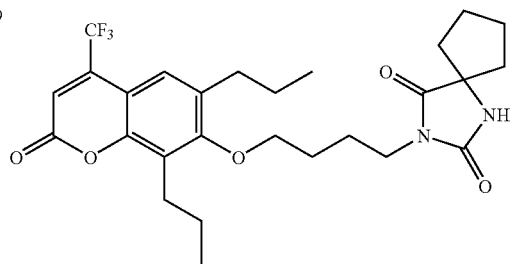 | 3-(4-(2-oxo-6,8-dipropyl-4-(trifluoromethyl)-2H-chromen-7-yloxy)butyl)-1,3-diazaspiro[4.4]nonane-2,4-dione |
| Example 220 | 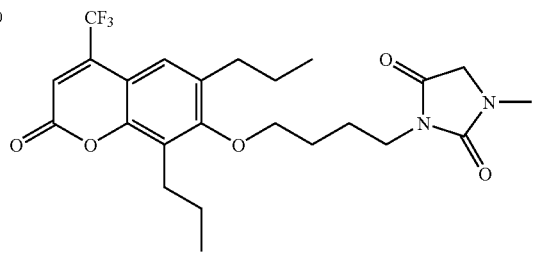 | 1-methyl-3-(4-(2-oxo-6,8-dipropyl-4-(trifluoromethyl)-2H-chromen-7-yloxy)butyl)-imidazolidin-2,4-dione |
| Example 221 | 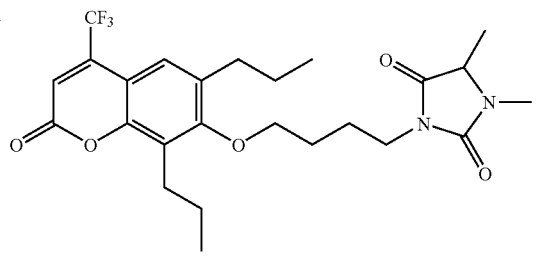 | 1,5-dimethyl-3-(4-(2-oxo-6,8-dipropyl-4-(trifluoromethyl)-2H-chromen-7-yloxy)butyl)-imidazolidin-2,4-dione |

TABLE 1-27

| Example 222 | 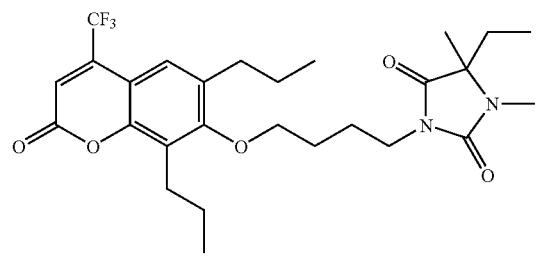 | 5-ethyl-1,5-dimethyl-3-(4-(2-oxo-6,8-dipropyl-4-(trifluoromethyl)-2H-chromen-7-yloxy)butyl)imidazolidin-2,4-dione |
| Example 223 | 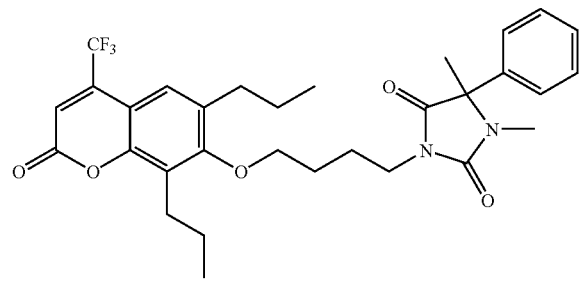 | 1,5-dimethyl-3-(4-(2-oxo-6,8-dipropyl-4-(trifluoromethyl)-2H-chromen-7-yloxy)butyl)-5-phenylimidazolidin-2,4-dione |

TABLE 1-27-continued

| Example 224 | 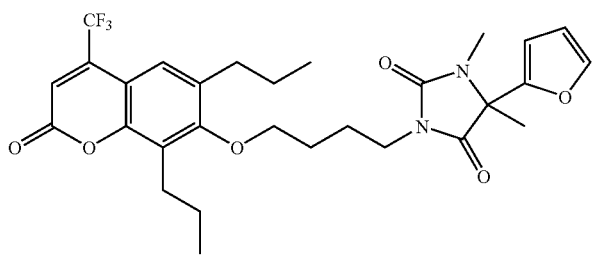 | 5-(furan-2-yl)-1,5-dimethyl-3-(4-(2-oxo-6,8-dipropyl-4-(trifluoromethyl)-2H-chromen-7-yloxy)butyl)imidazolidin-2,4-dione |
| --- | --- | --- |
| Example 225 | 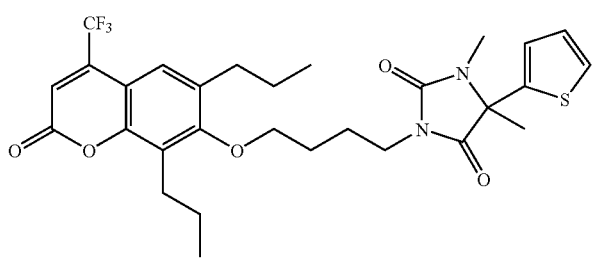 | 1,5-dimethyl-3-(4-(2-oxo-6,8-dipropyl-4-(trifluoromethyl)-2H-chromen-7-yloxy)butyl)-5-(thiophen-2-yl)imidazolidin-2,4-dione |
| Example 226 | 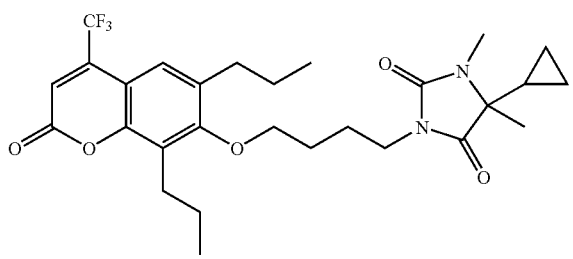 | 5-cyclopropyl-1,5-dimethyl-3-(4-(2-oxo-6,8-dipropyl-4-(trifluoromethyl)-2H-chromen-7-yloxy)butyl)imidazolidin-2,4-dione |
| Example 227 | 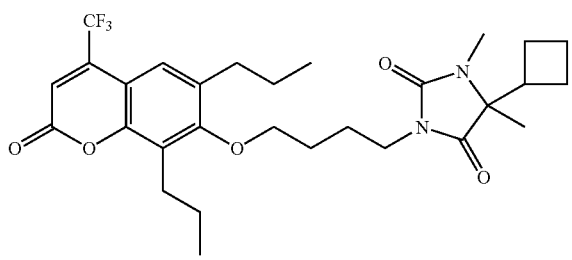 | 5-cyclobutyl-1,5-dimethyl-3-(4-(2-oxo-6,8-dipropyl-4-(trifluoromethyl)-2H-chromen-7-yloxy)butyl)imidazolidin-2,4-dione |
| Example 228 | 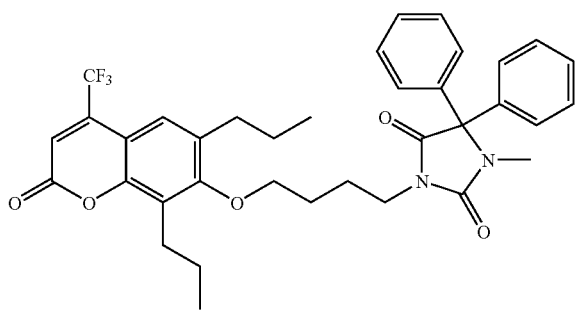 | 1-methyl-3-(4-(2-oxo-6,8-dipropyl-4-(trifluoromethyl)-2H-chromen-7-yloxy)butyl)-5,5-diphenylimidazolidin-2,4-dione |

TABLE 1-27-continued

| Example 229 | 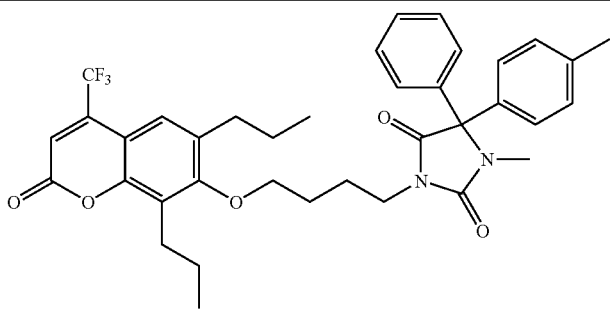 | 1-methyl-3-(4-(2-oxo-6,8-dipropyl-4-(trifluoromethyl)-2H-chromen-7-yloxy)butyl)-5-phenyl-5-p-totylimidazolidin-2,4-dione |

TABLE 1-28

| Example 230 | 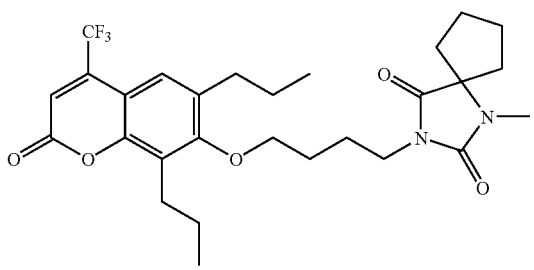 | 1-methyl-3-(4-(2-oxo-6,8-dipropyl-4-(trifluoromethyl)-2H-chromen-7-yloxy)butyl)-1,3-diazaspiro[4.4]nonane-2,4-dione |
| Example 231 | 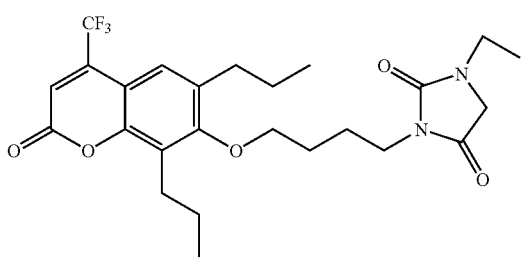 | 1-ethyl-3-(4-(2-oxo-6,8-dipropyl-4-(trifluoromethyl)-2H-chromen-7-yloxy)butyl)-imidazolidin-2,4-dione |
| Example 232 | 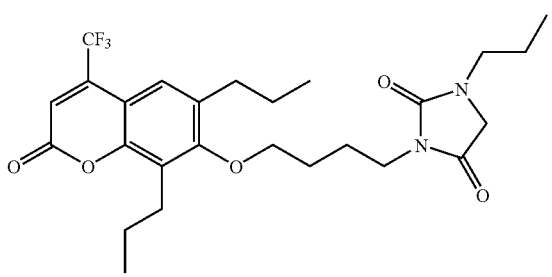 | 3-(4-(2-oxo-6,8-dipropyl-4-(trifluoromethyl)-2H-chromen-7-yloxy)butyl)-1-propylimidazolidin-2,4-dione |
| Example 233 | 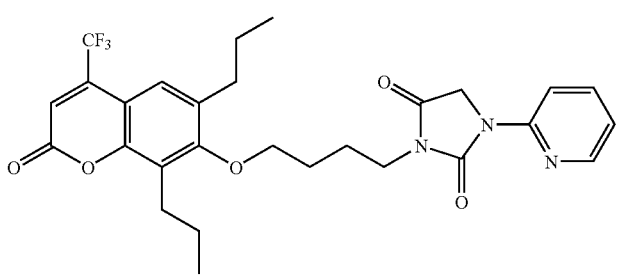 | 3-(4-(2-oxo-6,8-dipropyl-4-(trifluoromethyl)-2H-chromen-7-yloxy)butyl)-1-(pyridin-2-yl)imidazolidin-2,4-dione |

TABLE 1-28-continued

| Example 234 | 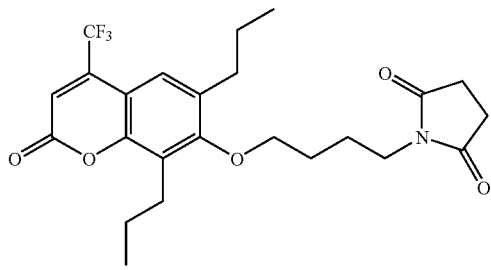 | 1-(4-(2-oxo-6,8-dipropyl-4-(trifluoromethyl)-2H-chromen-7-yloxy)butyl)pyrrolidine-2,5-dione |
| Example 235 | 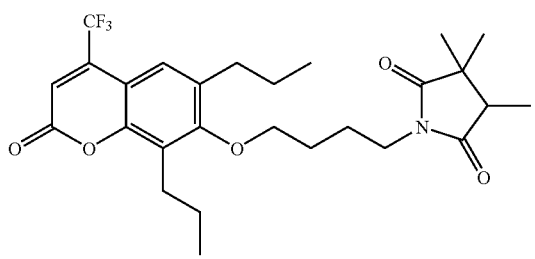 | 3,3,4-trimethyl-1-(4-(2-oxo-6,8-dipropyl-4-(trifluoromethyl)-2H-chromen-7-yloxy)-butyl)pyrrolidine-2,5-dione |
| Example 236 | 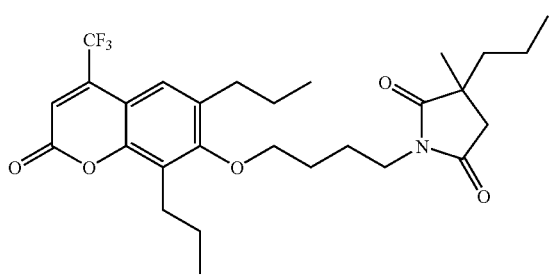 | 3-methyl-1-(4-(2-oxo-6,8-dipropyl-4-(trifluoromethyl)-2H-chromen-7-yloxy)butyl)-3-propylpyrrolidine-2,5-dione |
| Example 237 | 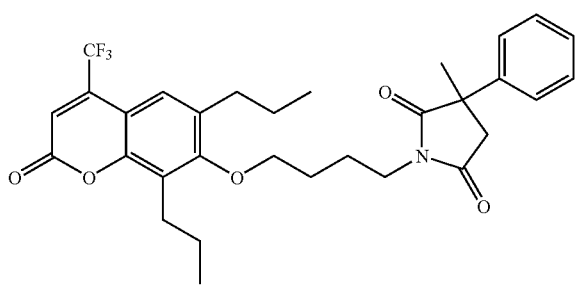 | 3-methyl-1-(4-(2-oxo-6,8-dipropyl-4-(trifluoromethyl)-2H-chromen-7-yloxy)butyl)-3-phenylpyrrolidine-2,5-dione |
| Example 238 | 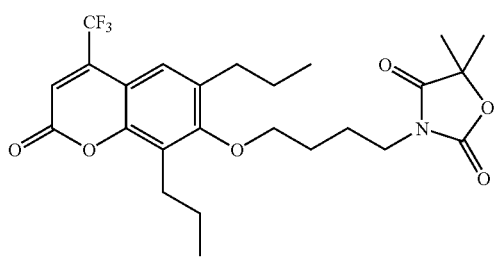 | 5,5-dimethyl-3-(4-(2-oxo-6,8-dipropyl-4-(trifluoromethyl)-2H-chromen-7-yloxy)butyl)-oxazolidin-2,4-dione |

TABLE 1-29

| Example 239 | 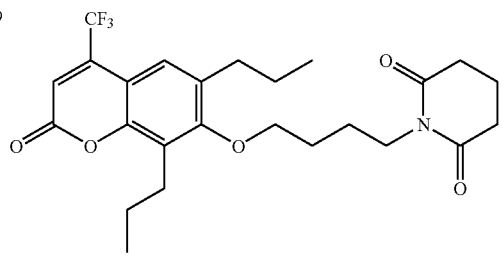 | 1-(4-(2-oxo-6,8-dipropyl-4-(trifluoromethyl)-2H-chromen-7-yloxy)butyl)piperidine-2,6-dione |
| Example 240 | 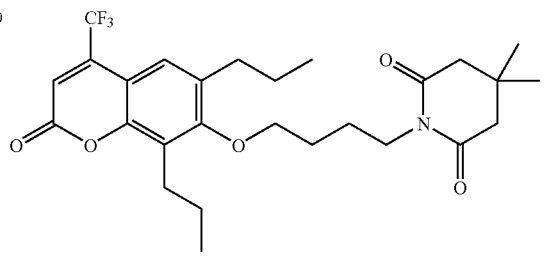 | 4,4-dimethyl-1-(4-(2-oxo-6,8-dipropyl-4-(trifluoromethyl)-2H-chromen-7-yloxy)butyl)-piperidine-2,6-dione |
| Example 241 | 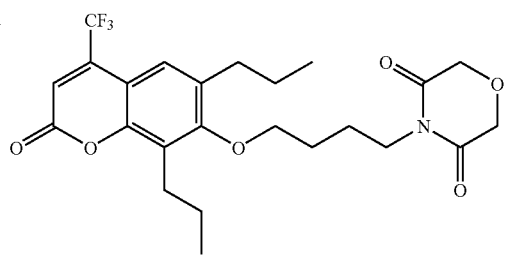 | 4-(4-(2-oxo-6,8-dipropyl-4-(trifluoromethyl)-2H-chromen-7-yloxy)butyl)morpholine-3,5-dione |
| Example 242 | 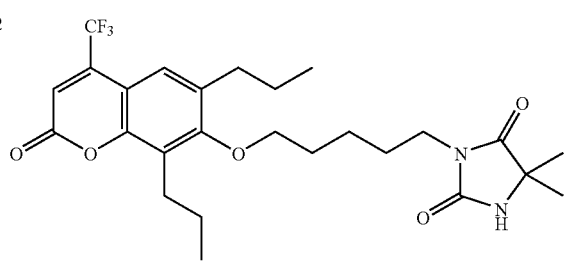 | 5,5-dimethyl-3-(5-(2-oxo-6,8-dipropyl-4-(trifluoromethyl)-2H-chromen-7-yloxy)-pentyl)imidazolidin-2,4-dione |
| Example 243 | 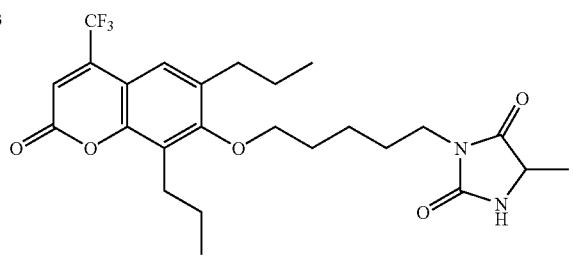 | 5-methyl-3-(5-(2-oxo-6,8-dipropyl-4-(trifluoromethyl)-2H-chromen-7-yloxy)pentyl)-imidazolidin-2,4-dione |
| Example 244 | 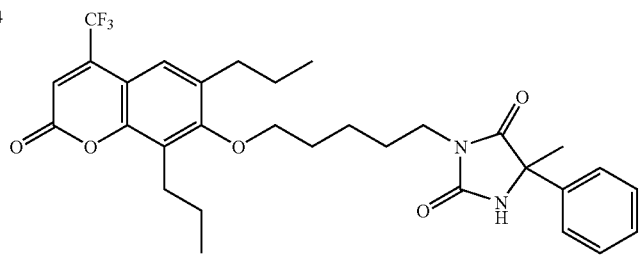 | 5-methyl-3-(5-(2-oxo-6,8-dipropyl-4-(trifluoromethyl)-2H-chromen-7-yloxy)pentyl)-5-phenylimidazolidin-2,4-dione |

TABLE 1-29-continued

| Example 245 | 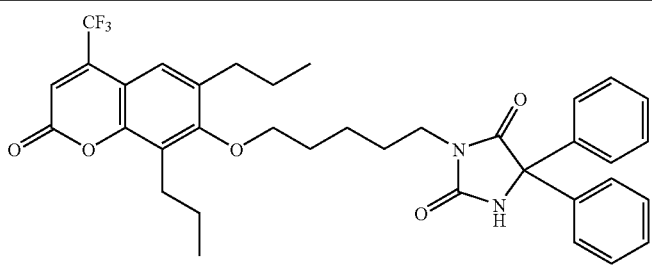 | 3-(5-(2-oxo-6,8-dipropyl-4-(trifluoromethyl)-2H-chromen-7-yloxy)pentyl)-5,5-diphenylimidazolidin-2,4-dione |
| Example 246 | 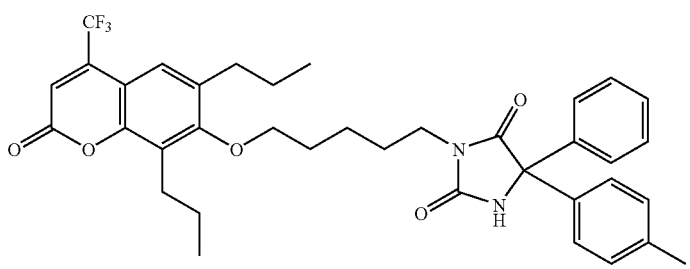 | 3-(5-(2-oxo-6,8-dipropyl-4-(trifluoromethyl)-2H-chromen-7-yloxy)pentyl)-5-phenyl-5-p-tolylimidazolidin-2,4-dione |
| Example 247 | 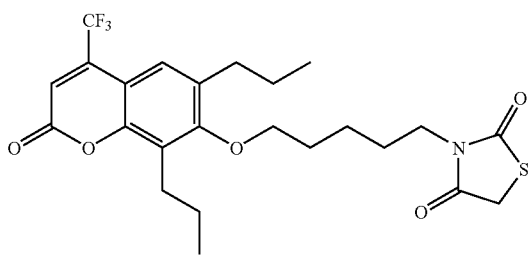 | 3-(5-(2-oxo-6,8-dipropyl-4-(trifluoromethyl)-2H-chromen-7-yloxy)pentyl)thiazolidin-2,4-dione |

TABLE 1-30

| Example 248 | 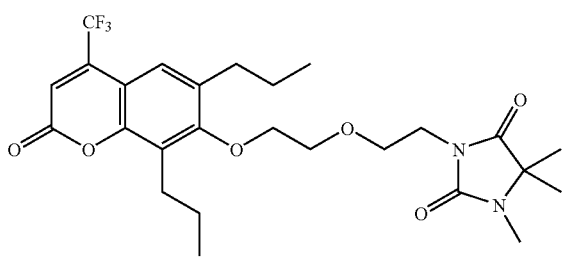 | 1,5,5-trimethyl-3-(2-(2-(2-oxo-6,8-dipropyl-4-(trifluoromethyl)-2H-chromen-7-yloxy)-ethoxy)ethyl)imidazolidin-2,4-dione |
| Example 249 | 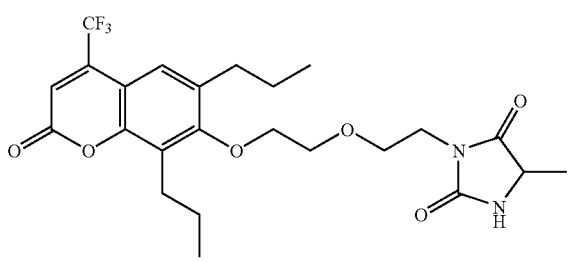 | 5-methyl-3-(2-(2-(2-oxo-6,8-dipropyl-4-(trifluoromethyl)-2H-chromen-7-yloxy)ethoxy)-ethyl)imidazolidin-2,4-dione |

TABLE 1-30-continued

| Example 250 | 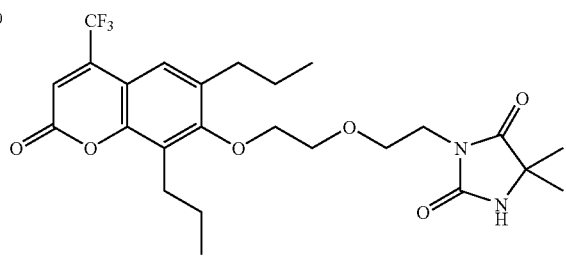 | 5,5-dimethyl-3-(2-(2-(2-oxo-6,8-dipropyl-4-(trifluoromethyl)-2H-chromen-7-yloxy)-ethoxy)ethyl)imidazolidin-2,4-dione |
| Example 251 | 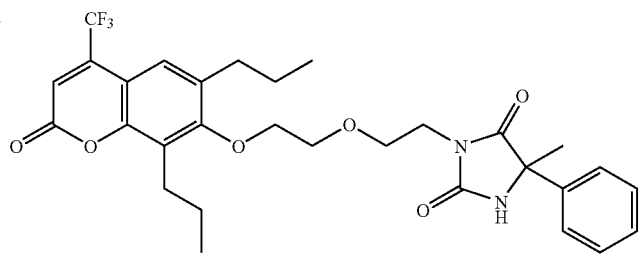 | 5-methyl-3-2-(2-(2-oxo-6,8-dipropyl-4-(trifluoromethyl)-2H-chromen-7-yloxy)-ethoxy)ethyl)-5-phenylimidazolidin-2,4-dione |
| Example 252 | 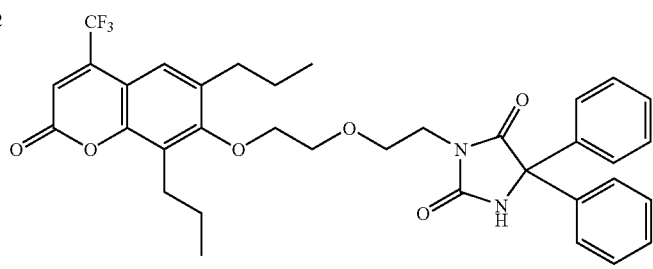 | 3-(2-(2-(2-oxo-6,8-dipropyl-4-(trifluoromethyl)-2H-chromen-7-yloxy)ethoxy)-ethyl)-5,5-diphenylimidazolidin-2,4-dione |
| Example 253 | 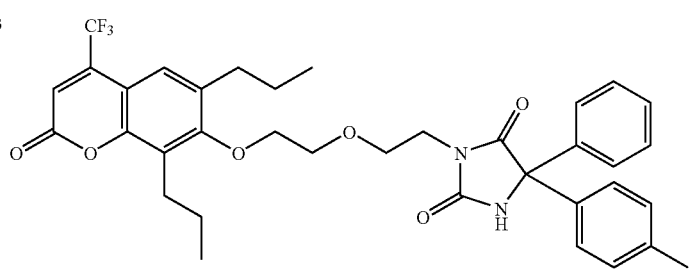 | 3-(2-(2-(2-oxo-6,8-dipropyl-4-(trifluoromethyl)-2H-chromen-7-yloxy)ethoxy)ethyl)-5-phenyl-5-p-tolylimidazolidin-2,4-dione |
| Example 254 | 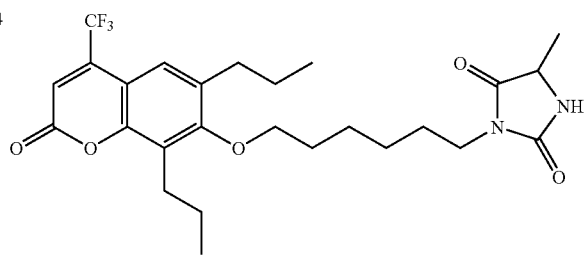 | 5-methyl-3-(6-(2-oxo-6,8-dipropyl-4-(trifluoromethyl)-2H-chromen-7-yloxy)hexyl)-imidazolidin-2,4-dione |
| Example 255 | 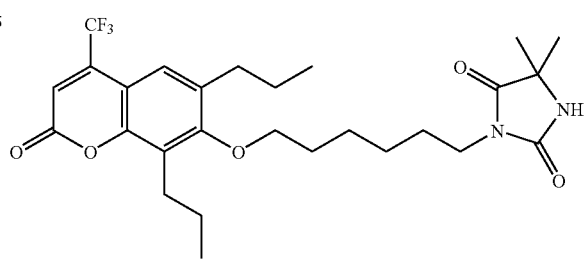 | 5,5-dimethyl-3-(6-(2-oxo-6,8-dipropyl-4-(trifluoromethyl)-2H-chromen-7-yloxy)hexyl)-imidazolidin-2,4-dione |

TABLE 1-31

Example 256 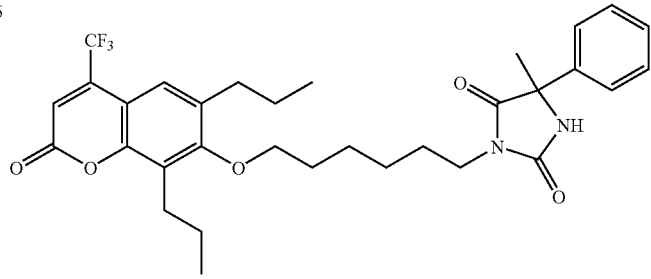 5-methyl-3-(6-(2-oxo-6,8-dipropyl-4-(trifluoromethyl)-2H-chromen-7-yloxy)hexyl)-5-phenylimidazolidin-2,4-dione Example 257 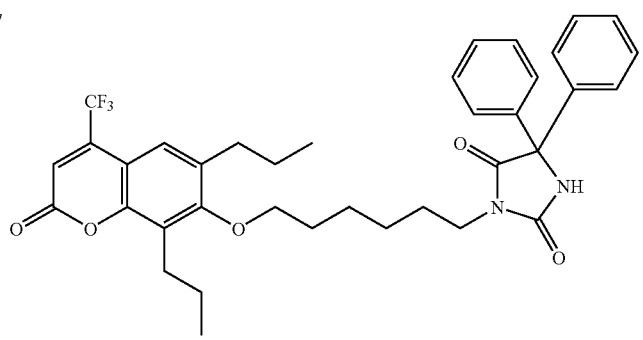 3-(6-(2-oxo-6,8-dipropyl-4-(trifluoromethyl)-2H-chromen-7-yloxy)hexyl)-5,5-diphenylimidazolidin-2,4-dione Example 258 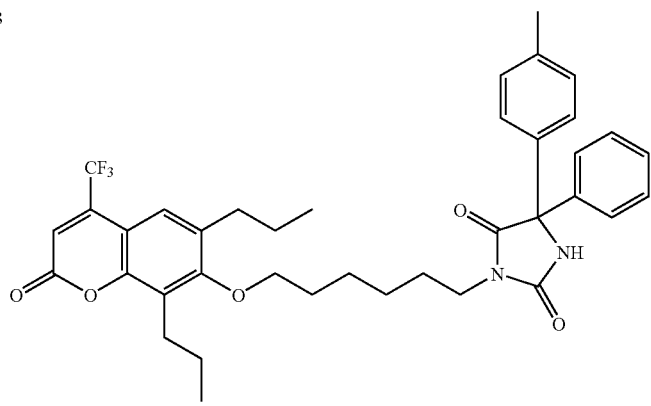 3-(6-(2-oxo-6,8-dipropyl-4-(trifluoromethyl)-2H-chromen-7-yloxy)hexyl)-5-phenyl-5-p-tolylimidazolidin-2,4-dione Example 259 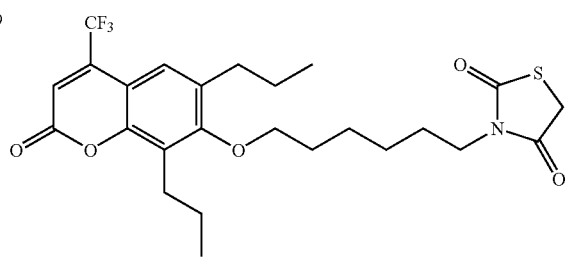 3-(6-(2-oxo-6,8-dipropyl-4-(trifluoromethyl)-2H-chromen-7-yloxy)hexyl)-thiazolidin-2,4-dione

TABLE 1-32

Example 260

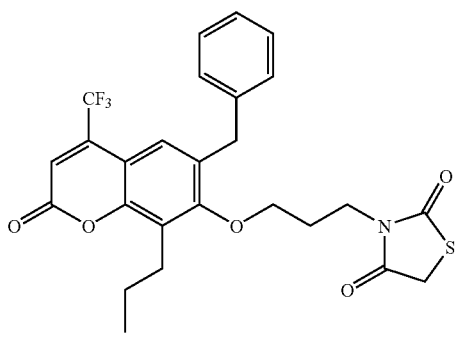

3-(3-(6-benzyl-2-oxo-8-propyl-4-(trifluoromethyl)-2H-chromen-7-yloxy)propyl)-thiazolidin-2,4-dione Example 261

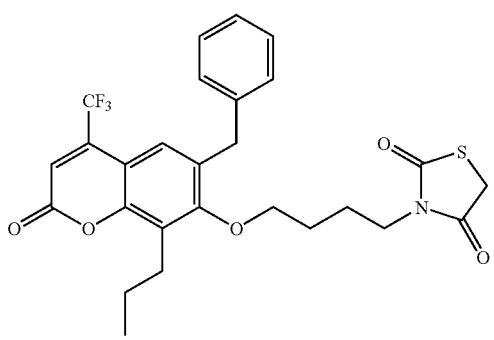

3-(4-(6-benzyl-2-oxo-8-propyl-4-(trifluoromethyl)-2H-chromen-7-yloxy)butyl)-thiazolidin-2,4-dione Example 262

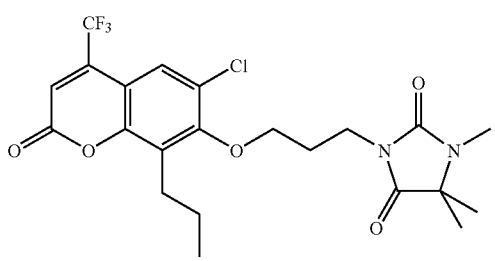

3-(3-(6-chloro-2-oxo-8-propyl-4-(trifluoromethyl)-2H-chromen-7-yloxy)propyl)-1,5,5-trimethylimidazolidin-2,4-dione Example 263

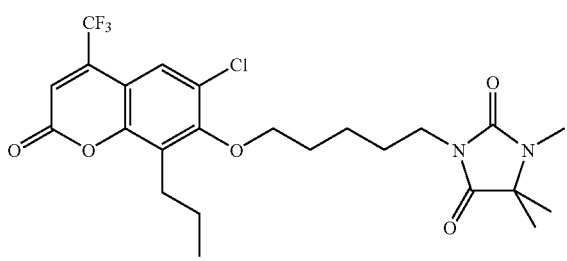

3-(5-(6-chloro-2-oxo-8-propyl-4-(trifluoromethyl)-2H-chromen-7-yloxy)pentyl)-1,5,5-trimethylimidazolidin-2,4-dione Example 264

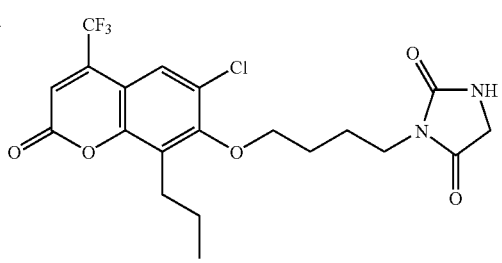

3-(4-(6-chloro-2-oxo-8-propyl-4-(trifluoromethyl)-2H-chromen-7-yloxy)butyl) imidazolidin-2,4-dione TABLE 1-32-continued

| Example 265 | 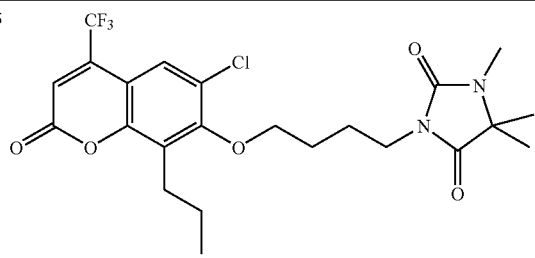 | 3-(4-(6-chloro-2-oxo-8-propyl-4-(trifluoromethyl)-2H-chromen-7-yloxy)butyl)-1,5,5-trimethylimidazolidin-2,4-dione |
| --- | --- | --- |
| Example 266 | 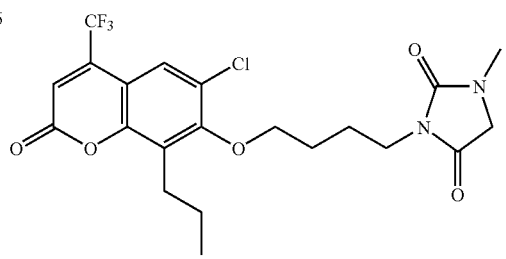 | 3-(4-(6-chloro-2-oxo-8-propyl-4-(trifluoromethyl)-2H-chromen-7-yloxy)butyl)-1-methylimidazolidin-2,4-dione |

TABLE 1-33

| Example 267 | 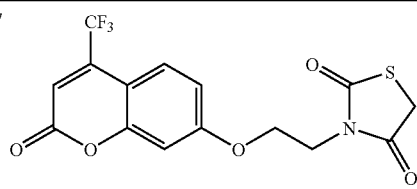 | 3-(2-(2-oxo-4-(trifluoromethyl)-2H-chromen-7-yloxy)ethyl)thiazolidin-2,4-dione |
| --- | --- | --- |
| Example 268 | 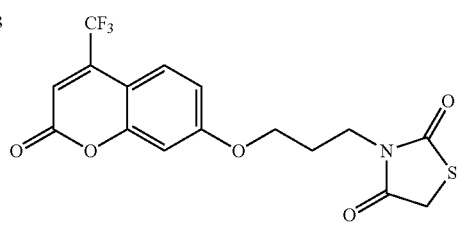 | 3-(3-(2-oxo-4-(trifluoromethyl)-2H-chromen-7-yloxy)propyl)thiazolidin-2,4-dione |
| Example 269 | 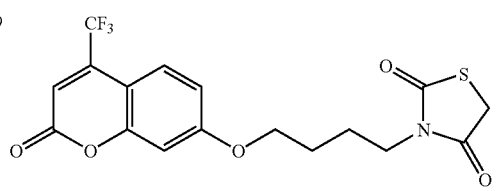 | 3-(4-(2-oxo-4-(trifluoromethyl)-2H-chromen-7-yloxy)butyl)thiazolidin-2,4-dione |
| Example 270 | 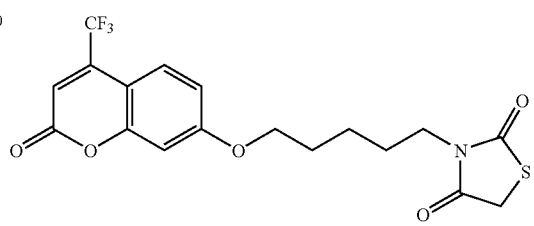 | 3-(5-(2-oxo-4-(trifluoromethyl)-2H-chromen-7-yloxy)pentyl)thiazolidin-2,4-dione |

TABLE 1-33-continued

| Example 271 | 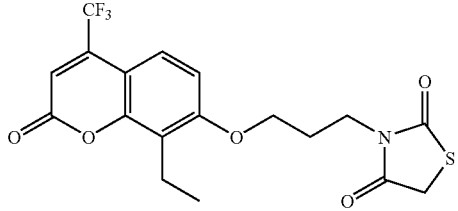 | 3-(3-(8-ethyl-2-oxo-4-(trifluoromethyl)-2H-chromen-7-yloxy)propyl)thiazolidin-2,4-dione |
| Example 272 | 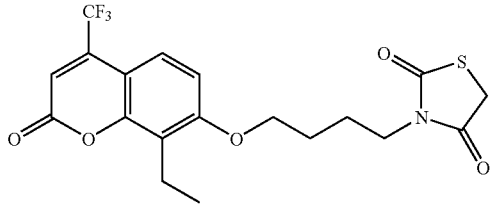 | 3-(4-(8-ethyl-2-oxo-4-(trifluoromethyl)-2H-chromen-7-yloxy)butyl)thiazolidin-2,4-dione |
| Example 273 | 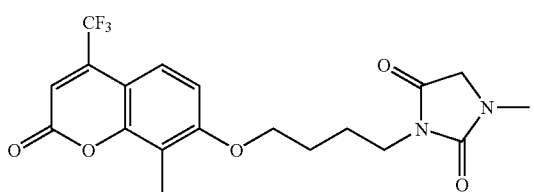 | 3-(4-(8-ethyl-2-oxo-4-(trifluoromethyl)-2H-chromen-7-yloxy)butyl)-1-methylimidazolidin-2,4-dione |
| Example 274 | 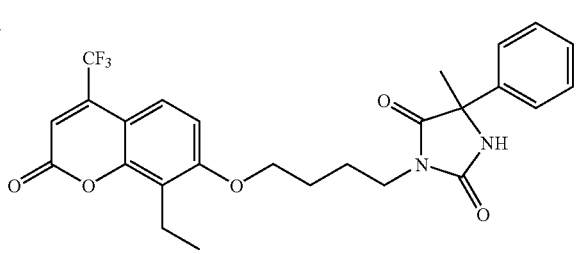 | 3-(4-(8-ethyl-2-oxo-4-(trifluoromethyl)-2H-chromen-7-yloxy)butyl)-5-methyl-5-phenylimidazolidin-2,4-dione |
| Example 275 | 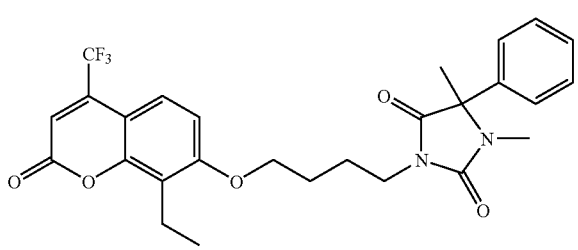 | 3-(4-(8-ethyl-2-oxo-4-(trifluoromethyl)-2H-chromen-7-yloxy)butyl)-1,5-dimethyl-5-phenylimidazolidin-2,4-dione |
| Example 276 | 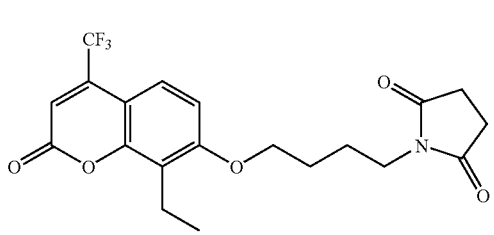 | 1-(4-(8-ethyl-2-oxo-4-(trifluoromethyl)-2H-chromen-7-yloxy)butyl)pyrrolidine-2,5-dione |

TABLE 1-34

| Example 277 | 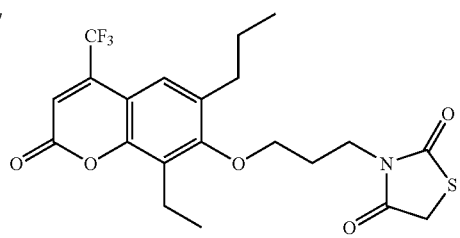 | 3-(3-(8-ethyl-2-oxo-6-propyl-4-(trifluoromethyl)-2H-chromen-7-yloxy)propyl)-thiazolidin-2,4-dione |
| Example 278 | 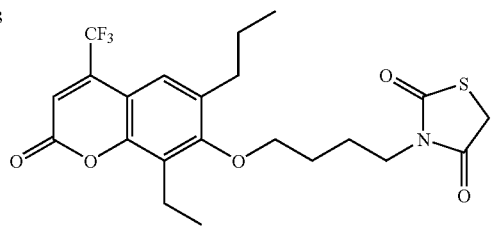 | 3-(4-(8-ethyl-2-oxo-6-propyl-4-(trifluoromethyl)-2H-chromen-7-yloxy)butyl) thiazolidin-2,4-dione |
| Example 279 | 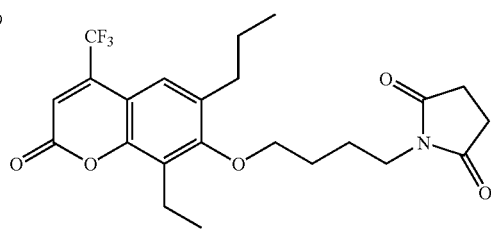 | 1-(4-(8-ethyl-2-oxo-6-propyl-4-(trifluoromethyl)-2H-chromen-7-yloxy)butyl)-pyrrolidine-2,5-dione |
| Example 280 | 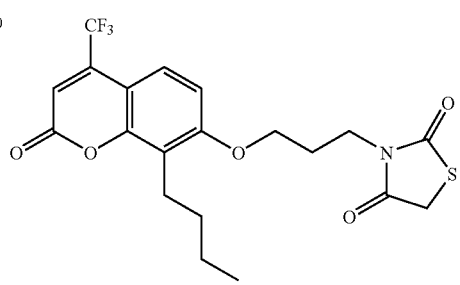 | 3-(3-(8-butyl-2-oxo-4-(trifluoromethyl)-2H-chromen-7-yloxy)propyl)thiazolidin-2,4-dione |
| Example 281 | 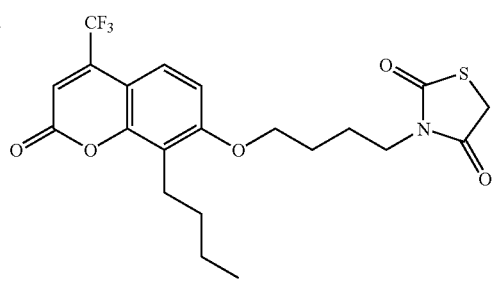 | 3-(4-(8-butyl-2-oxo-4-(trifluoromethyl)-2H-chromen-7-yloxy)butyl)thiazolidin-2,4-dione |
| Example 282 | 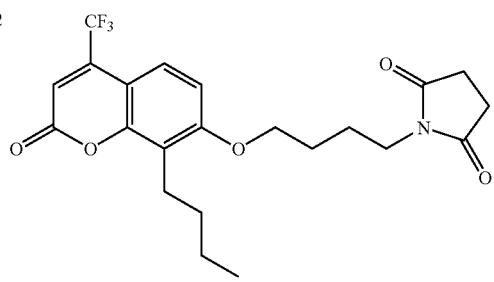 | 1-(4-(8-butyl-2-oxo-4-(trifluoromethyl)-2H-chromen-7-yloxy)butyl)pyrrolidine-2,5-dione |

TABLE 1-34-continued

Example 283
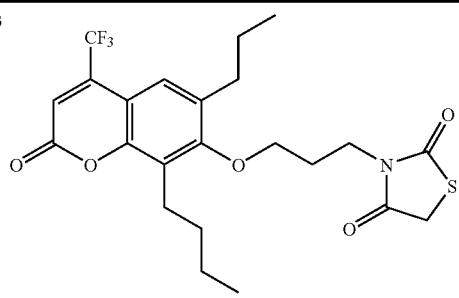
3-(3-(8-butyl-2-oxo-6-propyl-4-(trifluoromethyl)-2H-chromen-7-yloxy)propyl)-thiazolidin-2,4-dione Example 284
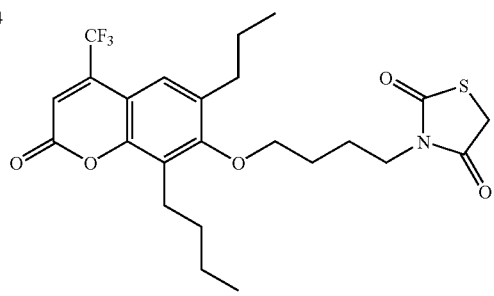
3-(4-(8-butyl-2-oxo-6-propyl-4-(trifluoromethyl)-2H-chromen-7-yloxy)butyl)thiazolidin-2,4-dione Example 285
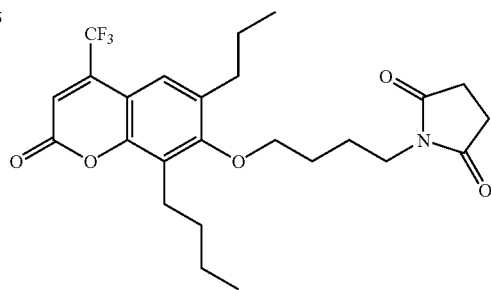
1-(4-(8-butyl-2-oxo-6-propyl-4-(trifluoromethyl)-2H-chromen-7-yloxy)butyl)-pyrrolidine-2,5-dione

TABLE 1-35

Example 286
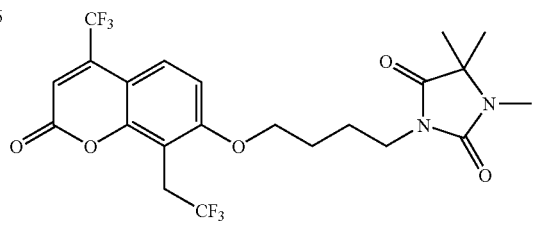
1,5,5-trimethyl-3-(4-(2-oxo-8-(2,2,2-trifluoroethyl)-4-(trifluoromethyl)-2H-chromen-7-yloxy)butyl)imidazolidin-2,4-dione Example 287
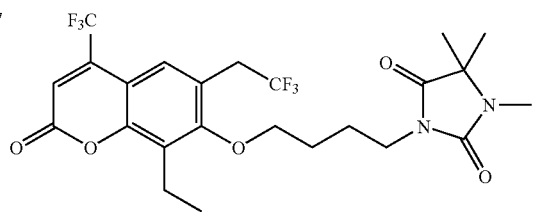
3-(4-(8-ethyl-2-oxo-6-(2,2,2-trifluoroethyl)-4-(trifluoromethyl)-2H-chromen-7-yloxy)-butyl)-1,5,5-trimethylimidazolidin-2,4-dione

TABLE 1-35-continued

| | | |
|---|---|---|
| Example 288 | 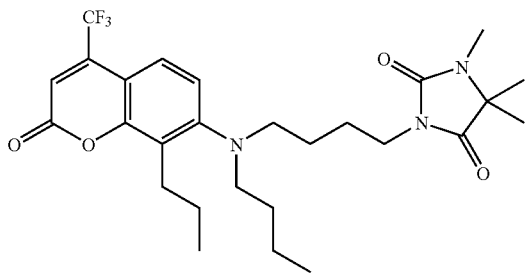 | 3-(4-(butyl(2-oxo-8-propyl-4-(trifluoromethyl)-2H-chromen-7-yl)amino)butyl)-1,5,5-trimethylimidazolidin-2,4-dione |
| Example 289 | 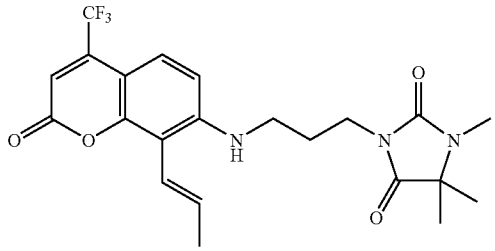 | (E)-1,5,5-trimethyl-3-(3-(2-oxo-8-(prop-1-enyl)-4-(trifluoromethyl)-2H-chromen-7-ylamino)propyl)imidazolidin-2,4-dione |
| Example 290 | 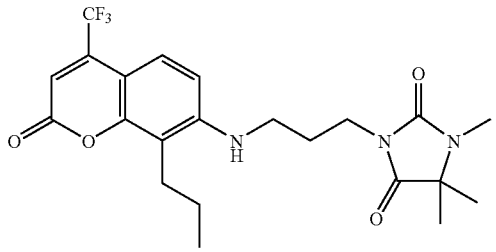 | 1,5,5-trimethyl-3-(3-(2-oxo-8-propyl-4-(trifluoromethyl)-2H-chromen-7-ylamino)propyl)-imidazolidin-2,4-dione |

TABLE 1-36

| | |
|---|---|
| Example 20 | $^1$H-NMR (CDCl$_3$) δ: 0.95 (3H, t, J = 7.3 Hz), 1.54-1.63 (2H, m), 1.77 (3H, s), 1.89-1.91 (4H, m), 2.88 (2H, t, J = 7.6 Hz), 3.67-3.69 (2H, m), 3.87 (3H, s), 4.09-4.15 (2H, m), 6.37 (1H, s), 6.60 (1H, s), 6.87 (1H, d, J = 9.0 Hz), 6.93-6.97 (2H, m), 7.32 (1H, m), 7.49-7.54 (2H, m). |
| Example 22 | $^1$H-NMR (CDCl$_3$) δ: 0.93 (3H, t, J = 7.3 Hz), 1.31 (6H, d, J = 6.1 Hz), 1.51-1.60 (2H, m), 1.81-1.85 (7H, m), 2.80 (2H, t, J = 7.6 Hz), 3.61 (2H, t, J = 6.2 Hz), 4.07 (2H, t, J = 5.4 Hz), 4.53 (1H, m), 6.25 (1H, s), 6.60 (1H, s), 6.84-6.89 (3H, m), 7.35-7.39 (2H, m), 7.52 (1H, m). |
| Example 24 | $^1$H-NMR (CDCl$_3$) δ: 0.93 (3H, t, J = 7.3 Hz), 1.00 (6H, d, J = 6.6 Hz), 1.51-1.64 (2H, m), 1.81-1.84 (7H, m), 2.06 (1H, m), 2.80 (2H, t, J = 7.7 Hz), 3.61 (2H, t, J = 6.2 Hz), 3.69 (2H, t, J = 6.6 Hz), 4.07 (2H, t, J = 5.3 Hz), 5.85 (1H, s), 6.60 (1H, s), 6.83-6.91 (3H, m), 7.36-7.39 (2H, m), 7.52 (1H, m). |
| Example 28 | $^1$H-NMR (CDCl$_3$) δ: 0.92 (3H, t, J = 7.4 Hz), 1.29 (9H, s), 1.51-1.60 (2H, m), 1.83-1.85 (7H, m), 2.81 (2H, t, J = 7.7 Hz), 3.74-3.75 (2H, m), 4.09-4.10 (2H, m), 6.50 (1H, s), 6.61 (1H, s), 6.85 (1H, d, J = 9.0 Hz), 7.39-7.44 (4H, m), 7.52 (1H, m). |
| Example 31 | $^1$H-NMR (CDCl$_3$) δ: 0.92 (3H, t, J = 7.3 Hz), 1.50-1.58 (2H, m), 1.82 (7H, m), 2.79 (2H, t, J = 7.6 Hz), 3.59-3.63 (2H, m), 4.06-4.09 (2H, m), 6.60 (1H, s), 6.83 (1H, d, J = 9.0 Hz), 6.90 (1H, s), 7.33-7.36 (2H, m), 7.45-7.66 (3H, m). |
| Example 32 | $^1$H-NMR (CDCl$_3$) δ: 0.92 (3H, t, J = 7.3 Hz), 1.48-1.61 (2H, m), 1.82 (7H, m), 2.79 (2H, t, J = 7.6 Hz), 3.59-3.61 (2H, m), 4.07-4.11 (2H, m), 6.61 (1H, s), 6.84 (1H, d, J = 9.2 Hz), 6.90 (1H, s), 7.39-7.55 (5H, m). |
| Example 33 | $^1$H-NMR (CDCl$_3$) δ: 0.92 (3H, t, J = 7.3 Hz), 1.50-1.59 (2H, m), 1.84-1.95 (7H, m), 2.79 (2H, t, J = 7.7 Hz), 3.64 (2H, t, J = 6.4 Hz), 4.08 (2H, t, J = 3.7 Hz), 6.61 (1H, s), 6.84 (1H, d, J = 9.0 Hz), 6.93 (1H, s), 7.52 (1H, d, J = 9.0 Hz), 7.52-7.79 (2H, m), 8.22-8.24 (2H, m). |
| Example 34 | $^1$H-NMR (CDCl$_3$) δ: 0.93 (3H, t, J = 7.4 Hz), 1.51-1.62 (2H, m), 1.79-2.09 (7H, m), 2.80 (2H, t, J = 7.6 Hz), 2.93 (6H, s), 3.58-3.60 (2H, m), 4.07-4.09 (2H, m), 6.31 (1H, s), 6.60 (1H, s), 6.68 (2H, d, J = 9.0 Hz), 6.84 (1H, d, J = 9.0 Hz), 7.27-7.32 (2H, m), 7.52 (1H, m). |
| Example 37 | $^1$H-NMR (CDCl$_3$) δ: 0.93 (3H, t, J = 7.3 Hz), 1.51-1.72 (6H, m), 1.80-1.84 (8H, m), 2.00 (1H, m), 2.80 (2H, t, J = 7.6 Hz), 3.55-3.60 (3H, m), 3.85 (1H, m), 4.08-4.09 (2H, m), 5.39 (1H, m), 6.60-6.70 (2H, m), 6.85 (1H, d, J = 9.0 Hz), 7.04 (2H, d, J = 8.8 Hz), 7.39 (2H, d, J = 8.8 Hz), 7.52 (1H, m). |
| Example 39 | $^1$H-NMR (CDCl$_3$) δ: 0.92 (3H, t, J = 7.3 Hz), 1.50-1.62 (2H, m), 1.82-1.89 (7H, m), 2.80 (2H, t, J = 7.6 Hz), 3.62-3.65 (2H, m), 4.06-4.09 (2H, m), 6.54-6.64 (2H, m), 6.84 (1H, d, J = 9.0 Hz), 7.51-7.59 (3H, m), 7.99-8.01 (2H, m). |
| Example 40 | $^1$H-NMR (CDCl$_3$) δ: 0.86-0.93 (3H, m), 1.49-1.58 (2H, m), 1.84-1.93 (7H, m), 2.78 (2H, t, J = 7.7 Hz), 3.64-3.69 (2H, m), 4.08 (2H, t, J = 5.5 Hz), 6.64 (1H, s), 6.86 (1H, d, J = 9.0 Hz), 7.54-7.56 (2H, m), 7.63 (2H, d, J = 8.6 Hz), 8.11 (2H, d, J = 8.5 Hz), 11.91 (1H, brs). |

TABLE 1-36-continued

| | |
|---|---|
| Example 42 | ¹H-NMR (CDCl₃) δ: 0.93 (3H, t, J = 7.3 Hz), 1.51-1.60 (2H, m), 1.82-1.98 (7H, m), 2.80 (2H, t, J = 7.6 Hz), 3.61 (2H, t, J = 6.2 Hz), 3.86 (3H, s), 3.89 (3H, s), 4.04-4.09 (2H, m), 6.24 (1H, s), 6.61 (1H, s), 6.83-6.86 (2H, m), 7.02-7.04 (2H, m), 7.52 (1H, m). |
| Example 46 | ¹H-NMR (CDCl₃) δ: 0.92 (3H, t, J = 7.4 Hz), 1.51-1.59 (2H, m), 1.73-1.82 (7H, m), 2.79 (2H, t, J = 7.6 Hz), 3.60-3.62 (2H, m), 4.08-4.11 (2H, m), 6.61 (1H, s), 6.84 (2H, d, J = 8.9 Hz), 7.37-7.63 (4H, m). |
| Example 52 | ¹H-NMR (CDCl₃) δ: 0.92 (3H, t, J = 7.3 Hz), 1.52-1.59 (2H, m), 1.90-1.97 (4H, m), 2.08 (3H, s), 2.81 (2H, t, J = 7.6 Hz), 3.64-3.79 (2H, m), 4.10-4.13 (2H, m), 6.36 (1H, s), 6.60 (1H, s), 6.85 (1H, d, J = 9.0 Hz), 7.39-7.53 (4H, m), 7.66 (1H, m), 7.83-7.93 (3H, m). |
| Example 58 | ¹H-NMR (CDCl₃) δ: 0.94 (3H, t, J = 7.4 Hz), 1.03 (9H, s), 1.50-1.63 (2H, m), 1.85-1.87 (4H, m), 2.81 (2H, t, J = 7.6 Hz), 3.63-3.64 (2H, m), 4.09-4.11 (2H, m), 6.61 (1H, s), 6.83 (1H, d, J = 8.9 Hz), 7.30-7.39 (3H, m), 7.51 (1H, m), 7.65-7.69 (2H, m), 8.26 (1H, s). |
| Example 60 | ¹H-NMR (CDCl₃) δ: 0.95 (3H, t, J = 7.5 Hz), 1.15 (3H, d, J = 7.6 Hz), 1.30 (3H, s), 1.53-1.65 (2H, m), 1.79-1.83 (4H, m), 2.56 (1H, q, J = 7.5 Hz), 2.82 (2H, t, J = 7.6 Hz), 3.58 (2H, t, J = 6.5 Hz), 4.10 (2H, t, J = 5.5 Hz), 6.61 (1H, s), 6.87 (1H, d, J = 9.0 Hz), 7.53 (1H, dd, J = 2.0, 9.0 Hz). |
| Example 65 | ¹H-NMR (CDCl₃) δ: 0.94 (3H, t, J = 7.3 Hz), 1.53-1.62 (2H, m), 1.73 (3H, s), 1.85-1.87 (4H, m), 2.82 (2H, t, J = 7.7 Hz), 2.86 (1H, d, J = 18.0 Hz), 3.13 (1H, d, J = 18.3 Hz), 3.67-3.69 (2H, m), 4.10-4.13 (2H, m), 6.61 (1H, s), 6.85 (1H, d, J = 9.0 Hz), 7.27-7.39 (5H, m), 7.53 (1H, dd, J = 2.0, 9.0 Hz). |
| Example 67 | ¹H-NMR (CDCl₃) δ: 0.96 (3H, t, J = 7.4 Hz), 1.43 (3H, d, J = 7.3 Hz), 1.54-1.64 (2H, m), 1.85-1.87 (4H, m), 2.83 (2H, t, J = 7.6 Hz), 2.96 (3H, s), 3.58-3.60 (2H, m), 3.87 (1H, q, J = 5.9 Hz), 4.10-4.12 (2H, m), 6.61 (1H, s), 6.87 (1H, d, J = 9.0 Hz), 7.53 (1H, dd, J = 2.0, 9.0 Hz). |

TABLE 1-37

| | |
|---|---|
| Example 73 | ¹H-NMR (CDCl₃) δ: 0.93 (3H, t, J = 7.3 Hz), 1.53-1.57 (5H, m), 1.85 (4H, s), 2.81 (2H, t, J = 7.6 Hz), 2.90 (3H, s), 3.63-3.65 (2H, m), 4.09-4.10 (2H, m), 6.61 (1H, s), 6.85 (1H, d, J = 9.0 Hz), 7.35 (1H, m), 7.53 (1H, d, J = 6.8 Hz), 7.64 (1H, m), 8.57 (1H, d, J = 2.2 Hz), 8.62 (1H, d, J = 3.2 Hz). |
| Example 75 | ¹H-NMR (CDCl₃) δ: 0.93 (3H, t, J = 7.3 Hz), 1.52-1.61 (2H, m), 1.84-1.89 (7H, m), 2.81 (2H, t, J = 7.6 Hz), 2.91 (3H, s), 3.62-3.69 (2H, m), 4.08-4.13 (2H, m), 6.61 (1H, s), 6.85 (1H, d, J = 9.0 Hz), 7.00-7.03 (2H, m), 7.31 (1H, m), 7.52 (1H, m). |
| Example 78 | ¹H-NMR (CDCl₃) δ: 0.94 (3H, t, J = 7.4 Hz), 1.50-1.64 (2H, m), 1.83-1.93 (4H, m), 2.81 (2H, t, J = 7.7 Hz), 2.96 (3H, s), 3.71 (2H, t, J = 6.6 Hz), 4.10 (2H, t, J = 5.5 Hz), 6.61 (1H, s), 6.86 (1H, d, J = 8.9 Hz), 7.40-7.55 (6H, m). |
| Example 118 | ¹H-NMR (CDCl₃) δ: 0.97 (3H, t, J = 7.3 Hz), 1.52-1.64 (4H, m), 1.74-1.83 (2H, m), 1.89-1.95 (2H, m), 2.84 (2H, t, J = 7.6 Hz), 3.66 (2H, t, J = 7.3 Hz), 4.08 (2H, t, J = 6.3 Hz), 4.23 (2H, s), 6.60 (1H, s), 6.87 (1H, d, J = 8.9 Hz), 7.39 (1H, d, J = 7.6 Hz), 7.52-7.59 (2H, m), 7.67 (1H, t, J = 7.6 Hz), 7.78 (1H, d, J = 7.9 Hz). |
| Example 125 | ¹H-NMR (CDCl₃) δ: 0.95 (3H, t, J = 7.6 Hz), 1.52-1.64 (4H, m), 1.76-1.96 (4H, m), 2.82 (2H, t, J = 7.6 Hz), 3.68 (2H, t, J = 7.3 Hz), 4.05-4.13 (2H, m), 4.37 (2H, s), 6.60 (1H, s), 6.87 (1H, d, J = 8.9 Hz), 7.52-7.62 (2H, m), 8.02 (2H, d, J = 8.2 Hz), 8.41 (1H, s). |
| Example 152 | ¹H-NMR (CDCl₃) δ: 0.96 (3H, t, J = 7.6 Hz), 1.41 (6H, s), 1.54-1.64 (2H, m), 2.83 (2H, t, J = 7.8 Hz), 3.72-3.80 (4H, m), 3.88 (2H, t, J = 4.6 Hz), 4.21 (2H, t, J = 4.6 Hz), 5.49 (1H, s), 6.62 (1H, s), 6.90 (1H, d, J = 9.0 Hz), 7.55 (1H, dd, J = 1.7, 9.0 Hz). |
| Example 154 | ¹H-NMR (CDCl₃) δ: 0.94 (3H, t, J = 7.6 Hz), 1.52-1.62 (2H, m), 1.81 (3H, s), 2.81 (2H, t, J = 7.8 Hz), 3.70-3.78 (4H, m), 3.82 (2H, t, J = 4.9 Hz), 4.11 (2H, t, J = 4.9 Hz), 6.28 (1H, s), 6.61 (1H, s), 6.83 (1H, d, J = 9.0 Hz), 7.26-7.39 (3H, m), 7.47-7.54 (3H, m). |
| Example 157 | ¹H-NMR (CDCl₃) δ: 0.93 (3H, t, J = 7.6 Hz), 1.51-1.60 (2H, m), 2.30 (3H, s), 2.80 (2H, t, J = 7.6 Hz), 3.78-3.82 (4H, m), 3.85 (2H, t, J = 5.1 Hz), 4.09-4.15 (2H, m), 6.27 (1H, s), 6.61 (1H, s), 6.84 (1H, d, J = 9.0 Hz), 7.10 (2H, d, J = 7.8 Hz), 7.21 (2H, d, J = 7.8 Hz), 7.29-7.37 (5H, m), 7.52 (1H, dd, J = 2.0, 9.0 Hz). |
| Example 165 | ¹H-NMR (CDCl₃) δ: 0.97-1.03 (6H, m), 1.60-1.70 (4H, m), 2.18-2.29 (2H, m), 2.65 (2H, t, J = 7.8 Hz), 2.79-2.83 (2H, m), 3.90-3.96 (4H, m), 4.56 (2H, s), 6.69 (1H, s), 7.07 (1H, m), 7.38 (1H, s), 7.74 (1H, m), 8.25 (1H, d, J = 8.5 Hz), 8.33 (1H, m). |
| Example 181 | ¹H-NMR (CDCl₃) δ: 0.93-0.99 (9H, m), 1.42-1.52 (3H, m), 1.57-1.91 (13H, m), 2.60 (2H, t, J = 7.7 Hz), 2.76 (2H, t, J = 7.8 Hz), 3.63 (2H, t, J = 6.8 Hz), 3.81 (2H, t, J = 5.9 Hz), 3.94 (2H, t, J = 6.5 Hz), 6.14 (1H, s), 6.68 (1H, s), 6.88-6.91 (2H, m), 7.37-7.40 (3H, m). |
| Example 187 | ¹H-NMR (CDCl₃) δ: 0.92-0.98 (6H, m), 1.57-1.67 (4H, m), 1.80-1.90 (7H, m), 2.59 (2H, t, J = 7.7 Hz), 2.76 (2H, t, J = 7.8 Hz), 3.64 (2H, t, J = 7.0 Hz), 3.81 (2H, t, J = 5.9 Hz), 6.63 (1H, s), 6.69 (1H, s), 7.37 (1H, s), 7.64-7.71 (4H, m). |
| Example 188 | ¹H-NMR (CDCl₃) δ: 0.93-0.98 (6H, m), 1.57-1.67 (4H, m), 1.80-1.89 (7H, m), 2.60 (2H, t, J = 7.8 Hz), 2.74-2.78 (2H, m), 3.63 (2H, t, J = 7.0 Hz), 3.81 (2H, t, J = 6.0 Hz), 6.38 (1H, s), 6.69 (1H, s), 7.04-7.09 (2H, m), 7.37 (1H, s), 7.48-7.52 (2H, m). |
| Example 193 | ¹H-NMR (CDCl₃) δ: 0.94-1.00 (6H, m), 1.12-1.55 (6H, m), 1.58-1.68 (4H, m), 1.79-1.96 (7H, m), 2.61 (2H, t, J = 7.8 Hz), 2.75-2.79 (2H, m), 3.33 (4H, q, J = 7.1 Hz), 3.62 (2H, t, J = 6.7 Hz), 3.82 (2H, t, J = 5.9 Hz), 6.01 (1H, s), 6.63 (2H, d, J = 9.0 Hz), 6.68 (1H, s), 7.27 (2H, d, J = 9.0 Hz), 7.37 (1H, s). |
| Example 195 | ¹H-NMR (CDCl₃) δ: 0.87-0.97 (6H, m), 1.53-1.67 (4H, m), 1.81-1.88 (7H, m), 2.60 (2H, t, J = 7.7 Hz), 2.71 (2H, t, J = 7.8 Hz), 3.63 (2H, t, J = 6.8 Hz), 3.80-3.86 (2H, m), 4.91 (1H, s), 6.41 (1H, s), 6.69 (1H, s), 6.78-6.80 (2H, m), 7.28-7.31 (2H, m), 7.37 (1H, s). |
| Example 196 | ¹H-NMR (CDCl₃) δ: 0.86-0.98 (6H, m), 1.57-1.67 (4H, m), 1.80-1.89 (7H, m), 2.60 (2H, t, J = 7.8 Hz), 2.74-2.78 (2H, m), 3.64 (2H, t, J = 7.0 Hz), 3.81 (2H, t, J = 5.9 Hz), 6.53 (1H, s), 6.69 (1H, s), 7.37 (1H, s), 7.70 (4H, s). |
| Example 200 | ¹H-NMR (CDCl₃) δ: 0.93-0.99 (6H, m), 1.58-1.67 (4H, m), 1.83-2.00 (7H, m), 2.61 (2H, t, J = 7.8 Hz), 2.77 (2H, t, J = 7.8 Hz), 3.62-3.69 (2H, m), 3.74-3.83 (5H, m), 3.84 (6H, s), 6.48 (1H, s), 6.69 (1H, s), 6.74 (2H, s), 7.37 (1H, s). |

TABLE 1-37-continued

| | |
|---|---|
| Example 202 | $^1$H-NMR (CDCl$_3$) δ: 0.87-0.98 (6H, m), 1.57-1.67 (4H, m), 1.83-1.92 (7H, m), 2.60 (2H, t, J = 7.7 Hz), 2.74-2.78 (2H, m), 3.64 (2H, t, J = 6.8 Hz), 3.82 (2H, t, J = 5.8 Hz), 6.69 (1H, s), 6.83 (1H, s), 7.17 (1H, m), 7.28 (1H, m), 7.37-7.43 (2H, m). |
| Example 204 | $^1$H-NMR (CDCl$_3$) δ: 0.96-1.01 (6H, m), 1.60-1.70 (4H, m), 1.87-2.00 (7H, m), 2.63 (2H, t, J = 7.8 Hz), 2.77-2.81 (2H, m), 3.71 (2H, t, J = 7.0 Hz), 3.85 (2H, t, J = 6.0 Hz), 6.30 (1H, s), 6.69 (1H, s), 7.38-7.46 (2H, m), 7.51 (1H, d, J = 8.6 Hz). |

TABLE 1-38

| | |
|---|---|
| Example 205 | $^1$H-NMR (CDCl$_3$) δ: 0.91-0.99 (6H, m), 1.55-1.64 (4H, m), 1.79-1.95 (7H, m), 2.59 (2H, t, J = 7.6 Hz), 2.75 (2H, d, J = 7.7 Hz), 3.66 (2H, t, J = 6.6 Hz), 3.81 (2H, t, J = 5.4 Hz), 6.29 (1H, s), 6.67 (1H, s), 7.35-7.63 (10H, m). |
| Example 209 | $^1$H-NMR (CDCl$_3$) δ: 0.95-1.01 (6H, m), 1.59-1.69 (4H, m), 1.71-1.97 (7H, m), 2.63 (2H, t, J = 7.7 Hz), 2.77-2.81 (2H, m), 3.67 (2H, t, J = 6.8 Hz), 3.85 (2H, t, J = 6.0 Hz), 6.08 (1H, s), 6.35-6.39 (2H, m), 6.69 (1H, s), 7.37-7.38 (2H, m). |
| Example 212 | $^1$H-NMR (CDCl$_3$) δ: 0.25-0.37 (2H, m), 0.45 (1H, m), 0.59 (1H, m), 0.96-1.04 (6H, m), 1.25 (1H, m), 1.51 (3H, s), 1.60-1.71 (4H, m), 1.85-1.90 (4H, m), 2.63 (2H, t, J = 7.8 Hz), 2.77-2.81 (2H, m), 3.61 (2H, t, J = 6.5 Hz), 3.85 (2H, t, J = 5.7 Hz), 5.82 (1H, s), 6.69 (1H, s), 7.38 (1H, m). |
| Example 213 | $^1$H-NMR (CDCl$_3$) δ: 0.95-1.01 (6H, m), 1.34 (3H, s), 1.59-1.93 (14H, m), 2.62 (2H, t, J= 7.7 Hz), 2.73-2.80 (3H, m), 3.61-3.65 (2H, m), 3.83 (2H, t, J = 5.7 Hz), 6.13 (1H, s), 6.69 (1H, s), 7.37 (1H, s). |
| Example 214 | $^1$H-NMR (CDCl$_3$) δ: 0.92-0.99 (6H, m), 1.58-1.97 (8H, m), 2.60 (2H, t, J = 7.7 Hz), 2.76 (2H, t, J = 7.8 Hz), 3.70 (2H, t, J = 6.5 Hz), 3.82 (2H, t, J = 5.7 Hz), 6.70 (1H, s), 7.32-7.77 (7H, m). |
| Example 215 | $^1$H-NMR (CDCl$_3$) δ: 0.91-0.98 (9H, m), 1.57-1.67 (4H, m), 1.81-1.92 (4H, m), 2.09 (1H, m), 2.41 (1H, m), 2.60 (2H, t, J = 7.8 Hz), 2.74-2.77 (2H, m), 3.62 (2H, t, J = 6.8 Hz), 3.75-3.82 (5H, m), 6.69 (1H, s), 6.77 (1H, s), 6.80-6.92 (2H, m), 7.37 (1H, s), 7.44-7.47 (2H, m). |
| Example 236 | $^1$H-NMR (CDCl$_3$) δ: 0.91-1.01 (9H, m), 1.17-1.38 (4H, m), 1.47-1.71 (7H, m), 1.83-1.85 (4H, m), 2.44 (1H, d, J = 18.3 Hz), 2.63 (2H, t, J = 7.7 Hz), 2.66 (1H, d, J = 18.3 Hz), 2.79 (2H, t, J = 7.8 Hz), 3.59-3.62 (2H, m), 3.83-3.85 (2H, m), 6.69 (1H, s), 7.53 (1H, s). |
| Example 249 | $^1$H-NMR (CDCl$_3$) δ: 0.95-1.04 (6H, m), 1.46 (3H, d, J = 7.1 Hz), 1.59-1.71 (4H, m), 2.67 (2H, t, J = 7.8 Hz), 2.80-2.85 (2H, m), 3.76-3.80 (4H, m), 3.83-3.86 (2H, m), 3.95-3.98 (2H, m), 4.07-4.14 (1H, m), 5.68 (1H, s), 6.69 (1H, s), 7.38 (1H, d, J = 1.7 Hz). |
| Example 257 | $^1$H-NMR (CDCl$_3$) δ: 0.95-1.01 (6H, m), 1.36-1.44 (2H, m), 1.51-1.74 (8H, m), 1.75-1.84 (2H, m), 2.62 (2H, t, J = 7.6 Hz), 2.76-2.80 (2H, m), 3.61 (2H, t, J = 7.3 Hz), 3.78 (2H, t, J = 6.6 Hz), 6.62 (1H, s), 6.68 (1H, s), 7.31-7.38 (11H, m). |
| Example 277 | $^1$H-NMR (CDCl$_3$) δ: 1.00 (3H, t, J = 7.5 Hz), 1.25 (3H, t, J = 7.6 Hz), 1.61-1.70 (2H, m), 2.15-2.21 (2H, m), 2.64 (2H, t, J = 7.8 Hz), 2.85 (2H, q, J = 5.1 Hz), 3.85-3.93 (4H, m), 3.98 (2H, s), 6.73 (1H, s), 7.38 (1H, s). |
| Example 281 | $^1$H-NMR (CDCl$_3$) δ: 0.94 (3H, t, J = 7.3 Hz), 1.27-1.78 (4H, m), 1.86-1.88 (4H, m), 2.84 (2H, t, J = 7.6 Hz), 3.73 (2H, t, J = 6.8 Hz), 3.98 (2H, s), 4.11 (2H, t, J = 5.7 Hz), 6.61 (1H, s), 6.87 (1H, d, J = 8.9 Hz), 7.54 (1H, m). |
| Example 283 | $^1$H-NMR (CDCl$_3$) δ: 0.95-1.02 (6H, m), 1.40-1.49 (2H, m), 1.56-1.71 (4H, m), 2.15-2.21 (2H, m), 2.64 (2H, t, J = 7.7 Hz), 2.82 (2H, t, J = 7.8 Hz), 3.89-3.99 (4H, m), 4.02 (2H, s), 6.73 (1H, s), 7.39(1H, s). |
| Example 286 | $^1$H-NMR (CDCl$_3$) δ: 1.39 (6H, s), 1.84-1.86 (4H, m), 2.90 (3H, s), 3.59-3.60 (2H, m), 3.74 (2H, q, J = 10.3 Hz), 4.13-4.19 (2H, m), 6.65 (1H, s), 6.95 (1H, d, J = 8.9 Hz), 7.70 (1H, m). |
| Example 287 | $^1$H-NMR (CDCl$_3$) δ: 1.23-1.39 (9H, m), 1.79-1.88 (4H, m), 2.87-2.96 (5H, m), 3.47-3.62 (4H, m), 3.86-3.90 (2H, m), 6.74 (1H, s), 7.57 (1H, s). |

Test Example 1

Transactivation Assay

<Construction of Plasmid>

The ligand-binding domain (LBD) of a human LXRα and LXRβ cDNA was inserted adjacent to an yeast GAL4-transcription factor DNA-binding domain (DBD) of a mammal expression vector pBIND (Promega) to prepare an expression construct, thereby to produce pBIND-LXRα/GAL4 and pBIND-LXRβ/GAL4, respectively. PG5luc, a GAL4-responsive reporter construct, is a known vector that is available from Promega, and contains 5 copies of GAL4-response element located adjacent to the promoter as well as a luciferase reporter gene.

<Assay>

An LXRα/GAL4 or LXRβ/GAL4 hybrid and GAL4-responsive reporter vector pG5luc-stable-expression CHOK-1 cells were seeded under 5% $CO_2$ wet atmosphere at 37° C., at 20,000 cells/well on a 96-well plate containing HAM-F12 medium containing 10% immobilized bovine fetal serum, 100 units/ml of penicillin G, and 100 μg/ml of streptomycin sulfate. 24 hours later, the medium with a test compound dissolved therein over the test concentration range (0.01 μM, 0.1 μM, 1 μM, 10 μM) was added and incubated with the cells for 24 hours. By using Bright-Glo (Promega) as a luciferase assay substrate, and measuring the luminescence intensity with luminometer LB960 (Berthold Technologies), the effect of the test compound on the activation of luciferase transcription via the LXRα- or LXRβ-LBD was measured. T0901317 (the compound of Example 12 of WO2000/54759) was assessed at the same time as a comparative compound. The luciferase activity results are shown in Tables 2-1 to 2-3 as activity values (% eff) at the respective concentration of the test compound, relative to the T0901317 luminescence intensity of 100 at 10 μM.

<Results>

As shown in Tables 2-1 to 2-3, it was confirmed experimentally that the 2-oxochromene derivative of the present invention is an LXR agonist having a higher selectivity to LXRβ than T0901317 which is a control agent.

TABLE 2-1
| Example | Structure |
| --- | --- |
| T0901317 | 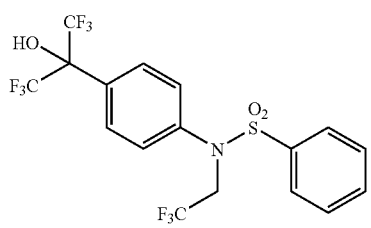 |
| Example 1 | 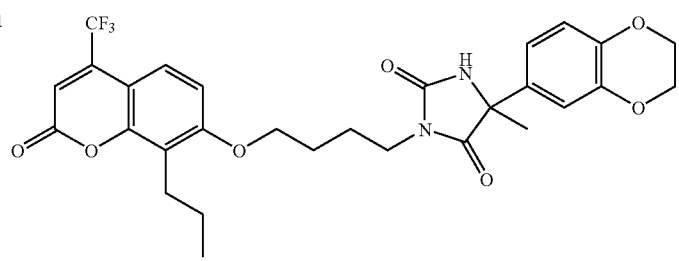 |
| Example 2 | 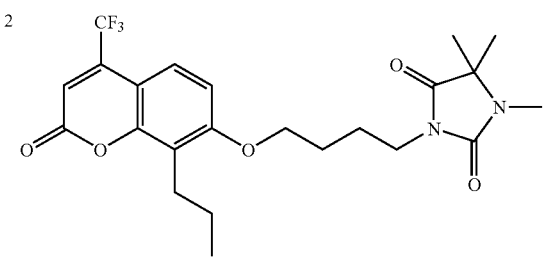 |
| Example 3 | 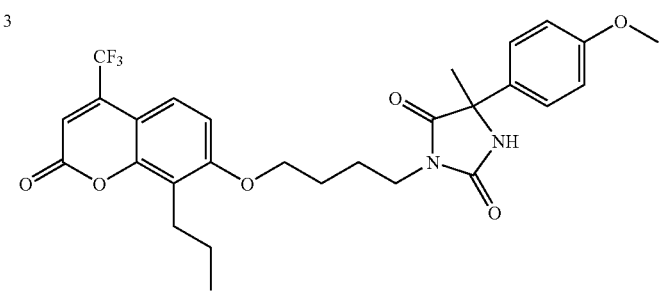 |
| Example 4 | 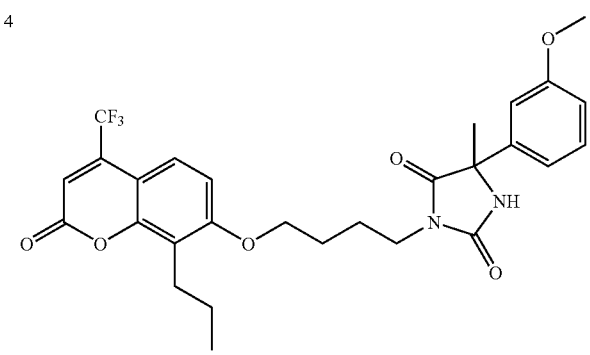 |

TABLE 2-1-continued
| Example 5 | 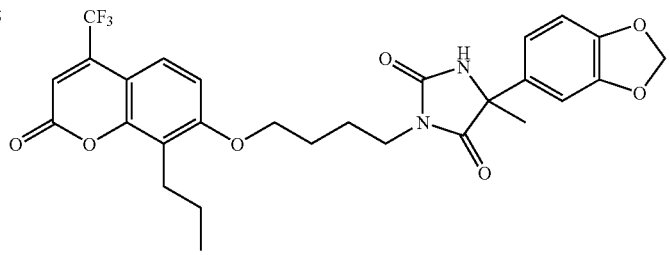 |
| Example | Activity |
|---|---|
| T0901317 | 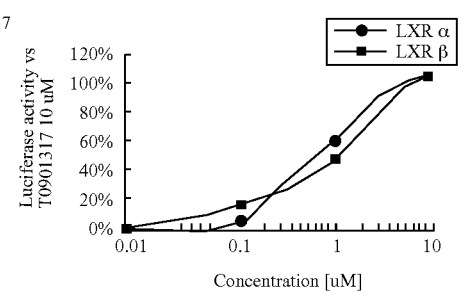 |
| Example 1 | 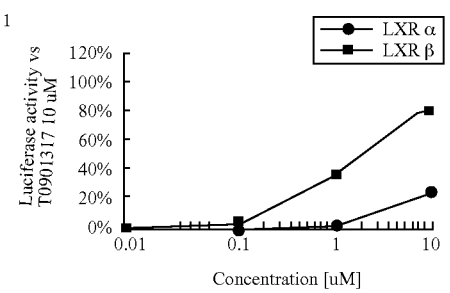 |
| Example 2 | 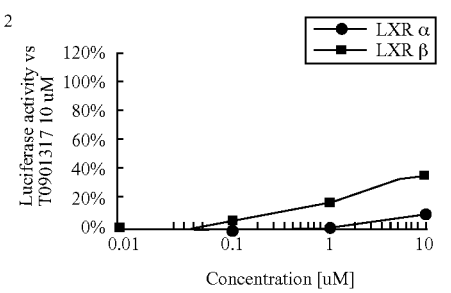 |
| Example 3 | 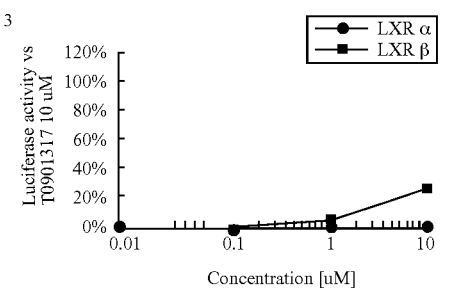 |

TABLE 2-1-continued
Example 4
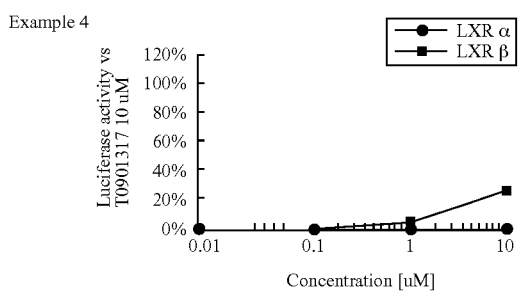
Example 5
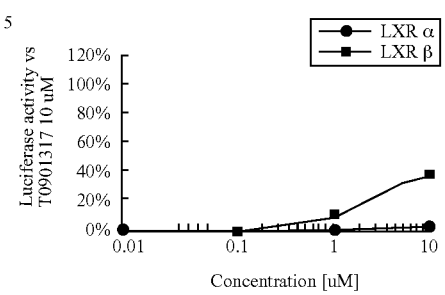
TABLE 2-2
| Example | Structure |
|---|---|
| T0901317 | 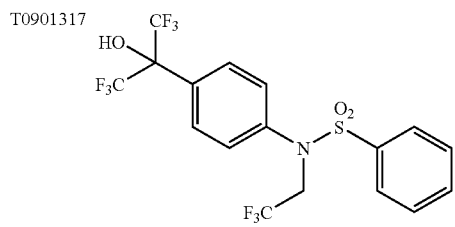 |
| Example 6 | 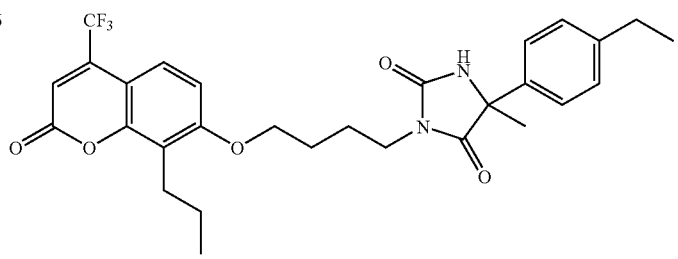 |
| Example 7 | 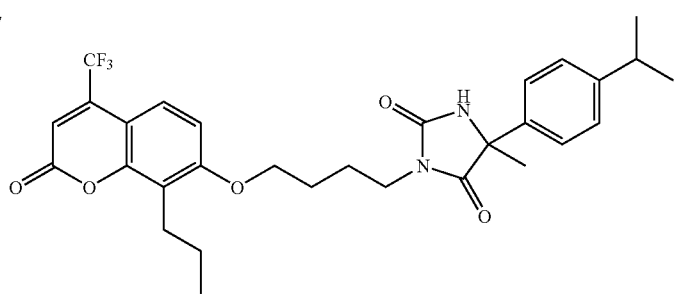 |

TABLE 2-2-continued
Example 8
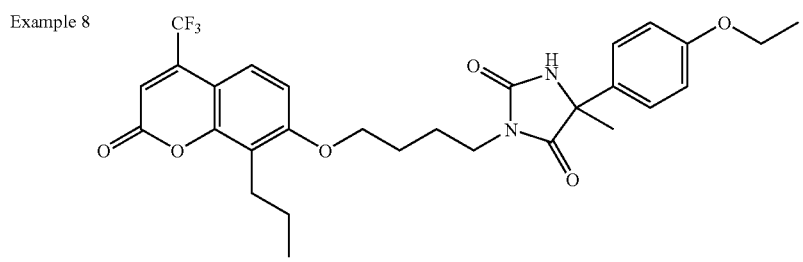
Example 9
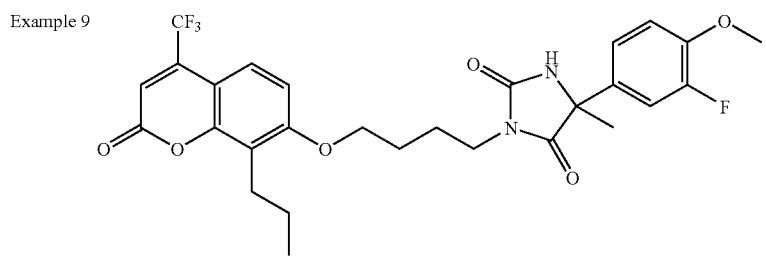
Example 10
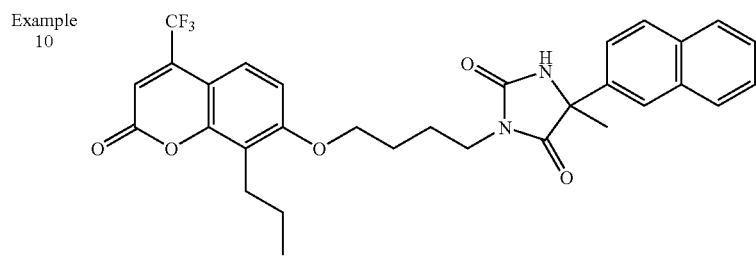
| Example | Activity |
|---|---|
T0901317
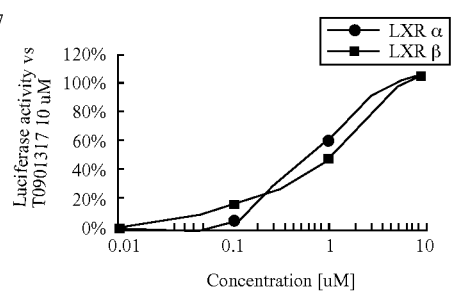
Example 6
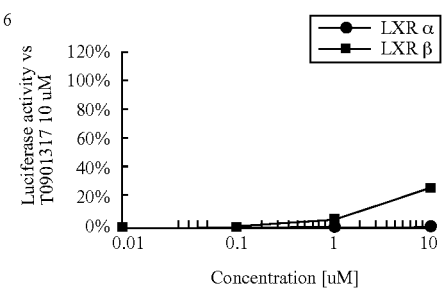

TABLE 2-2-continued
Example 7
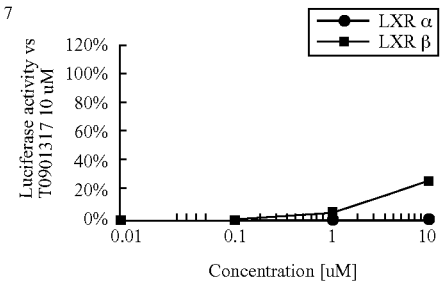
Example 8
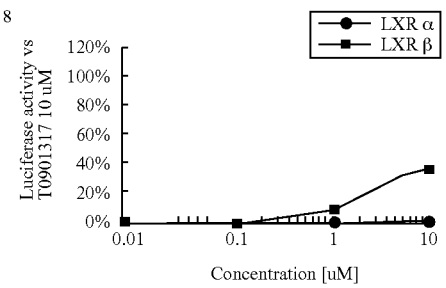
Example 9
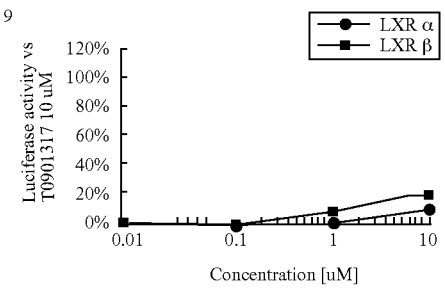
Example 10
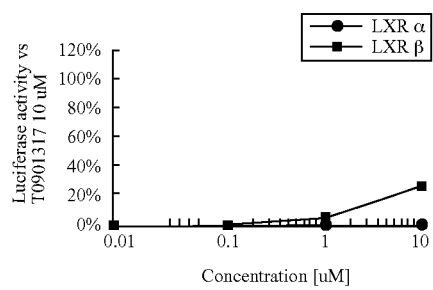
TABLE 2-3
| Example | Structure |
|---|---|
| T0901317 | 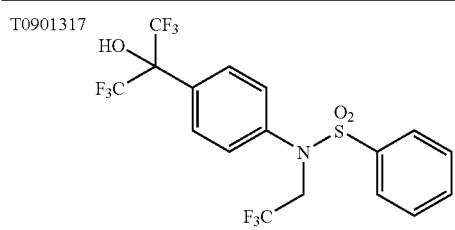 |

TABLE 2-3-continued
Example 11
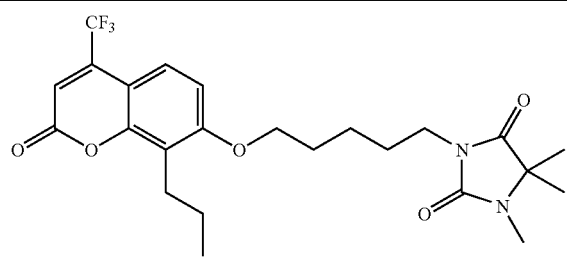
Example 12
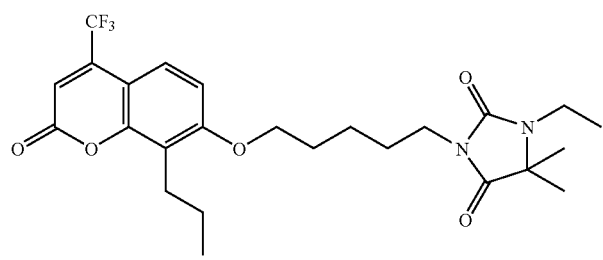
Example 13
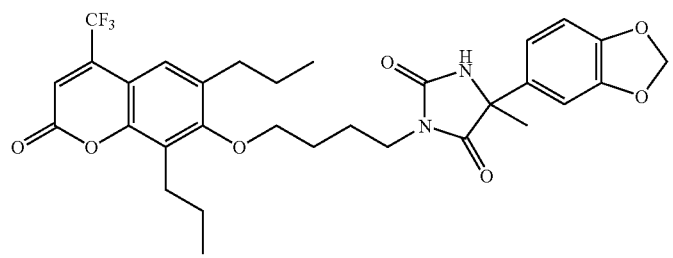
Example 14
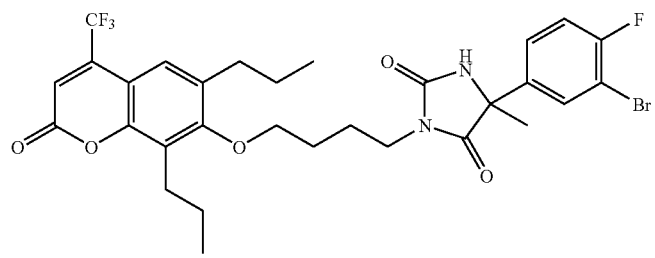
Example 15
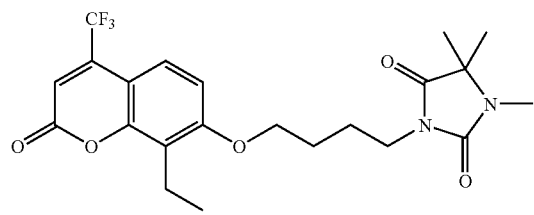
| Example | Activity |
|---|---|
T0901317
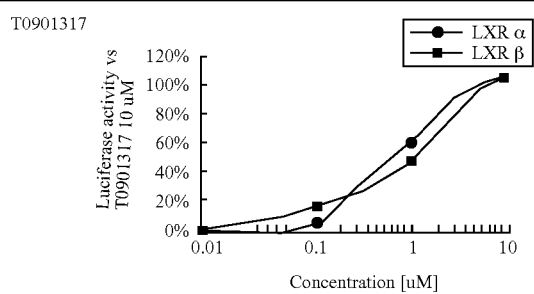

TABLE 2-3-continued
Example 11
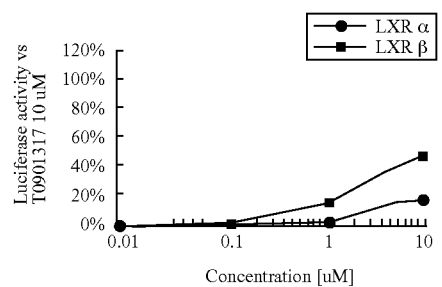
Example 12
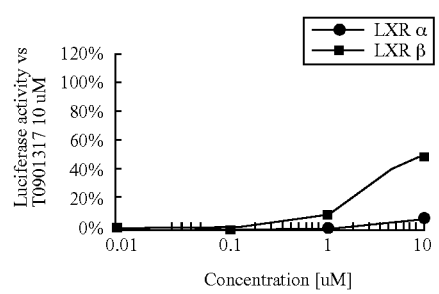
Example 13
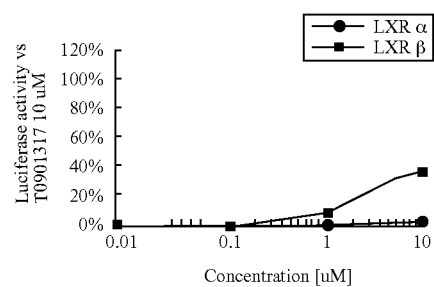
Example 14
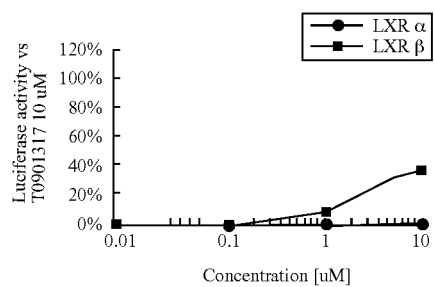
Example 15
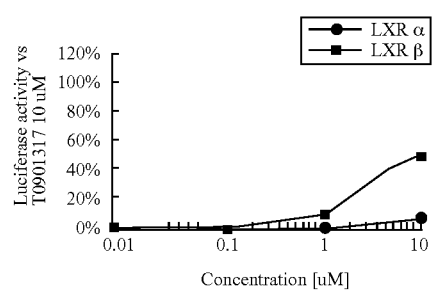

What is claimed is:

1. A 2-oxochromene derivative represented by the following general formula (1) or salt thereof:

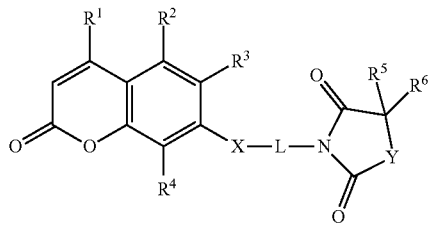

(wherein $R^1$ represents a halo $C_{1-8}$ alkyl group; $R^2$, $R^3$, and $R^4$ are either same or different and represent a hydrogen atom, halogen atom, $C_{1-8}$ alkyl group, halo $C_{1-8}$ alkyl group, $C_{2-8}$ alkenyl group, $C_{2-8}$ alkynyl group, $C_{1-8}$ alkoxy group $C_{1-8}$ acyl group, nitro group, cyano group, carboxyl group, carbamoyl group, or $C_{6-10}$ aryl $C_{1-8}$ alkyl group, wherein the $C_{6-10}$ aryl may have 1 to 3 substituents selected from the following group A; $R^5$ and $R^6$ are either same or different and represent a hydrogen atom, $C_{1-8}$ alkyl group, $C_{3-8}$ cycloalkyl group, halo $C_{1-8}$ alkyl group, $C_{6-10}$ aryl group or 5- to 11-membered heterocyclic group, wherein the $C_{6-10}$ aryl group and 5- to 11-membered heterocyclic group may have 1 to 3 substituents selected from the following group A, and $R^5$ and $R^6$ may together form a $C_{3-8}$ cycloalkyl ring; L represents a $C_{2-10}$ alkyl chain, $C_{2-10}$ alkenyl chain, or $C_{2-6}$ alkyl-O—$C_{2-6}$ alkyl chain; X represents —O— or —N($R^7$)—; $R^7$ represents a hydrogen atom or $C_{1-8}$ alkyl group; Y represents an O, S, —CH($R^8$)—, —CH$_2$CH ($R^9$)—, —CH$_2$O—, or) —N($R^{10}$)—; $R^8$ and $R^9$ are either same or different and represent a hydrogen atom or $C_{1-8}$ alkyl group; $R^{10}$ represents a hydrogen atom, $C_{1-8}$ alkyl group that may be substituted with a $C_{1-8}$ alkoxycarbonyl group, halo $C_{1-8}$ alkyl group, $C_{6-10}$ aryl group, or 5- to 11-membered heterocyclic group, wherein the $C_{6-10}$ aryl group and 5- to 11-membered heterocyclic group may have 1 to 3 substituents selected from the following group A), [Group A: halogen atom, $C_{1-8}$ alkyl group, halo $C_{1-8}$ alkyl group, $C_{2-8}$ alkenyl group, $C_{2-8}$ alkynyl group, $C_{3-8}$ cycloalkyl group, $C_{1-8}$ alkoxy group, halo $C_{1-8}$ alkoxy group, $C_{1-8}$ acyl group, nitro group, amino group, mono $C_{1-6}$ alkylamino group, di $C_{1-6}$ alkylamino group, cyano group, hydroxy group, carboxyl group, $C_{1-8}$ alkoxycarbonyl group, carbamoyl group, $C_{6-10}$ aryl group, 5- to 11-membered heterocyclic group, $C_{1-6}$ alkylthio group, $C_{1-6}$ alkylsulfonyl group, $C_{6-10}$ arylthio group, $C_{6-10}$ arylsulfonyl group, tetrahydropyranyloxy group, and $C_{1-6}$ alkylenedioxy group].

2. A medicine composition comprising a therapeutically effective amount of the 2-oxochromene derivative or salt thereof according to claim 1 as an active ingredient.

3. The medicine composition according to claim 2, which is a therapeutic agent for atherosclerosis, arteriosclerosis resulting from diabetes, dyslipidemia, hypercholesterolemia, diabetes, or Alzheimer's disease.

4. An LXR regulator containing the 2-oxochromene derivative or salt thereof according to claim 1 as an active ingredient.

5. A pharmaceutical composition comprising the 2-oxochromene derivative or salt thereof according to claim 1 and a pharmaceutically acceptable carrier.

6. A method for treating atherosclerosis, arteriosclerosis resulting from diabetes, dyslipidemia, hypercholesterolemia, diabetes, or Alzheimer's disease, in a subject in need thereof, comprising administering to said subject a therapeutically effective amount of the 2-oxochromene derivative or salt thereof according to claim 1.

7. The medicine composition according to claim 2 wherein the medicine composition is administered in the form of an oral preparation, injection, suppository, ointment, inhalation, eye-drops, nasal preparation, or adhesive patch.

8. The LXR regulator according to claim 4, wherein said LXR regulator has a higher selectivity for activating LXRβ expression than a LXRα expression.

* * * * *